United States Patent
Skokos et al.

(10) Patent No.: US 12,415,856 B2
(45) Date of Patent: Sep. 16, 2025

(54) EGFR X CD28 MULTISPECIFIC ANTIBODIES

(71) Applicant: Regeneron Pharmaceuticals, Inc., Tarrytown, NY (US)

(72) Inventors: Dimitris Skokos, New York, NY (US); Andrew J. Murphy, Tarrytown, NY (US); George D. Yancopoulos, Yorktown Heights, NY (US); Chia-yang Lin, Scarsdale, NY (US); Lauric Haber, Rye Brook, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 68 days.

(21) Appl. No.: 18/165,515

(22) Filed: Feb. 7, 2023

(65) Prior Publication Data

US 2023/0322927 A1 Oct. 12, 2023

Related U.S. Application Data

(63) Continuation of application No. 16/825,179, filed on Mar. 20, 2020, now Pat. No. 11,912,767.

(60) Provisional application No. 62/822,124, filed on Mar. 22, 2019.

(51) Int. Cl.
| | |
|---|---|
| C07K 16/28 | (2006.01) |
| A61K 9/00 | (2006.01) |
| A61K 39/00 | (2006.01) |
| A61K 39/395 | (2006.01) |
| A61K 45/06 | (2006.01) |
| A61P 35/00 | (2006.01) |
| C12N 5/071 | (2010.01) |

(52) U.S. Cl.
CPC ........ *C07K 16/2818* (2013.01); *A61K 9/0019* (2013.01); *A61K 39/3955* (2013.01); *A61K 45/06* (2013.01); *A61P 35/00* (2018.01); *C07K 16/2863* (2013.01); *C12N 5/0682* (2013.01); *A61K 2039/505* (2013.01); *C07K 2317/31* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 10,179,819 B2 | 1/2019 | Kirshner et al. | |
| 11,912,767 B2* | 2/2024 | Skokos .............. | C07K 16/3069 |
| 2005/0136050 A1 | 6/2005 | Kufer et al. | |
| 2014/0243504 A1 | 8/2014 | Davis et al. | |
| 2020/0239576 A1 | 7/2020 | Murphy et al. | |
| 2020/0299388 A1 | 9/2020 | Skokos et al. | |

FOREIGN PATENT DOCUMENTS

| | | |
|---|---|---|
| CN | 104411722 A | 3/2015 |
| CN | 104558190 A | 4/2015 |
| CN | 106632681 A | 5/2017 |
| JP | 2015-502373 A | 1/2015 |
| WO | 2007/042261 A2 | 4/2007 |
| WO | 2013/092001 A1 | 6/2013 |
| WO | 2014/004427 A2 | 1/2014 |

OTHER PUBLICATIONS

Che et al., Preparation and Preliminary Investigation of Function of Anti-EGFR/CD3 Bispecific Antibody. J Fujian Med Univ. Dec. 28, 2017;51(6):369-74.
Jung et al., Local immunotherapy of glioma patients with a combination of 2 bispecific antibody fragments and resting autologous lymphocytes: evidence for in situ t-cell activation and therapeutic efficacy. Int J Cancer. Jan. 15, 2001;91 (2):225-30.
Kussie et al., A single engineered amino acid substitution changes antibody fine specificity. J Immunol. Jan. 1, 1994;152(1):146-52.
Li et al., Advances in the Study of Bispecific Antibody and Its Application in Tumor Diagnosis and Treatment. J Med Molec Bio. May 30, 2005;3:233-5.
Lum et al., Development and prospects for bispecific antibody-based therapeutics in cancer and other applications. Expert Opin Drug Discov. Sep. 2008;3(9):1081-97.
Morris, Epitope Mapping of Protein Antigens by Competition ELISA. The Protein Protocols Handbook. Humana Press, Jan. 1, 1996; 595-600.
Panka et al., Variable region framework differences result in decreased or increased affinity of variant anti-digoxin antibodies. Proc Natl Acad Sci U S A. May 1988;85(9):3080-4.
Pfosser et al., Role of target antigen in bispecific-antibody-mediated killing of human glioblastoma cells: a pre-clinical study. Int J Cancer. Feb. 9, 1999;80(4):612-6.

(Continued)

*Primary Examiner* — Marianne P Allen
(74) *Attorney, Agent, or Firm* — McCarter & English, LLP; Marcie B. Clarke, Esq.

(57) ABSTRACT

The present invention provides multispecific antibodies that bind to EGFR and CD28 (EGFR×CD28) as well as anti-EGFR antibodies. Such antibodies may be combined with a further therapeutic agent such as an anti-PD1 antibody. Methods for treating cancers (e.g., EGFR-expressing cancer) by administering the antibodies (e.g., and combinations thereof with anti-PD1) are also provided. The EGFR×CD28 antibodies of the present invention embody a tumor-targeted immunotherapeutic modality combined with PD-1 inhibition. These bispecific antibodies bind a tumor-specific antigen (TSA) (EGFR) with one arm and the co-stimulatory receptor, CD28, on T-cells with the other arm. Combination therapy with PD-1 inhibitors specifically potentiated intratumoral T cell activation, promoting an effector memory-like T cell phenotype without systemic cytokine secretion in a variety of syngeneic and human tumor xenograft models. Combining this class of CD28-co-stimulatory bispecific antibodies with the clinically validated anti-PD-1 treatment provides a well-tolerated antibody therapy with markedly enhanced anti-tumor efficacy.

10 Claims, 29 Drawing Sheets
Specification includes a Sequence Listing.

(56) References Cited

OTHER PUBLICATIONS

Rudikoff et al., Single amino acid substitution altering antigen-binding specificity. Proc Natl Acad Sci U S A. Mar. 1982;79(6):1979-83.
International Search Report and Written Opinion for Application No. PCT/US2020/023857, dated Jul. 3, 2020, 10 pages.
Beyersdorf et al., Superagonistic anti-CD28 antibodies: potent activators of regulatory T cells for the therapy of autoimmune diseases. Ann Rheum Dis. Nov. 2005;64 Suppl 4(Suppl 4):iv91-5.
Bostrom et al., Improving antibody binding affinity and specificity for therapeutic development. Methods Mol Biol. 2009;525:353-76, xiii.
Dondelinger et al., Understanding the Significance and Implications of Antibody Numbering and Antigen-Binding Surface/Residue Definition. Front Immunol. Oct. 16, 2018;9:2278, 15 pages.
Gonzales et al., Minimizing the immunogenicity of antibodies for clinical application. Tumour Biol. Jan.-Feb. 2005;26 (1):31-43.
Hunig et al., The rise and fall of the CD28 superagonist TGN1412 and its return as TAB08: a personal account. Febs J. Sep. 2016;283(18):3325-34.
Kunik et al., Structural consensus among antibodies defines the antigen binding site. PLoS Comput Biol. 2012;8(2): e1002388, 12 pages.
O'Neil et al., An Unbiased Oncology Compound Screen to Identify Novel Combination Strategies. Mol Cancer Ther. Jun. 2016;15(6):1155-62.
Vajdos et al., Comprehensive functional maps of the antigen-binding site of an anti-ErbB2 antibody obtained with shotgun scanning mutagenesis. J Mol Biol. Jul. 5, 2002;320(2):415-28.
Wark et al., Latest technologies for the enhancement of antibody affinity. Adv Drug Deliv Rev. Aug. 7, 2006;58 (5-6):657-70.

\* cited by examiner

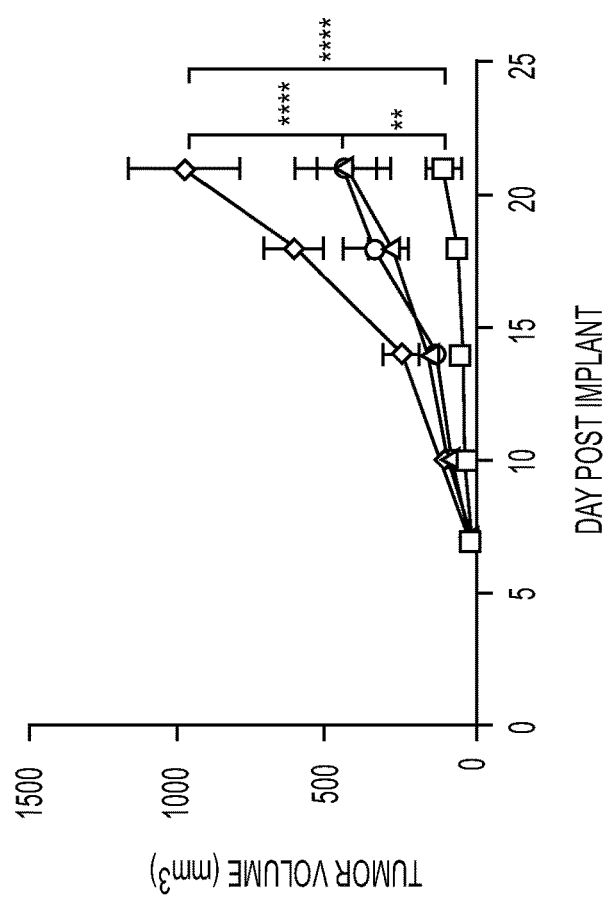
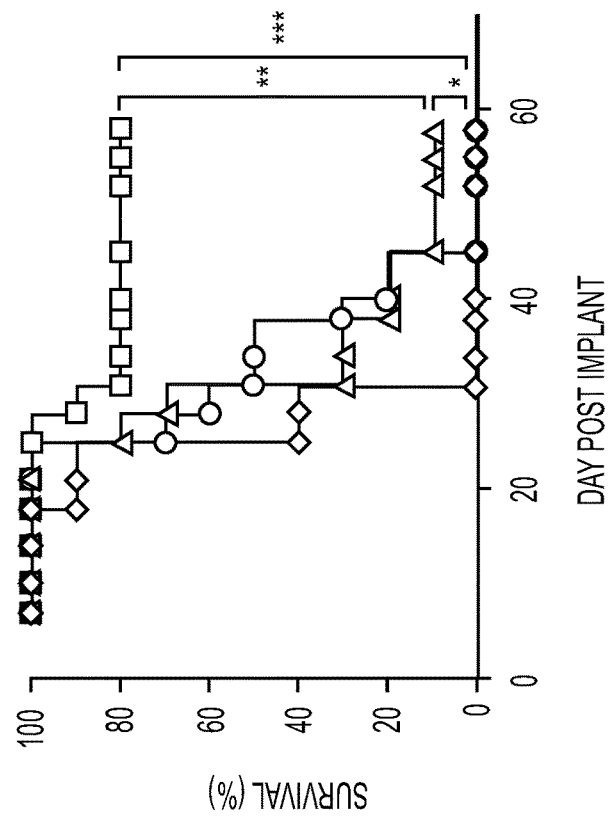
FIG. 2A
FIG. 2B

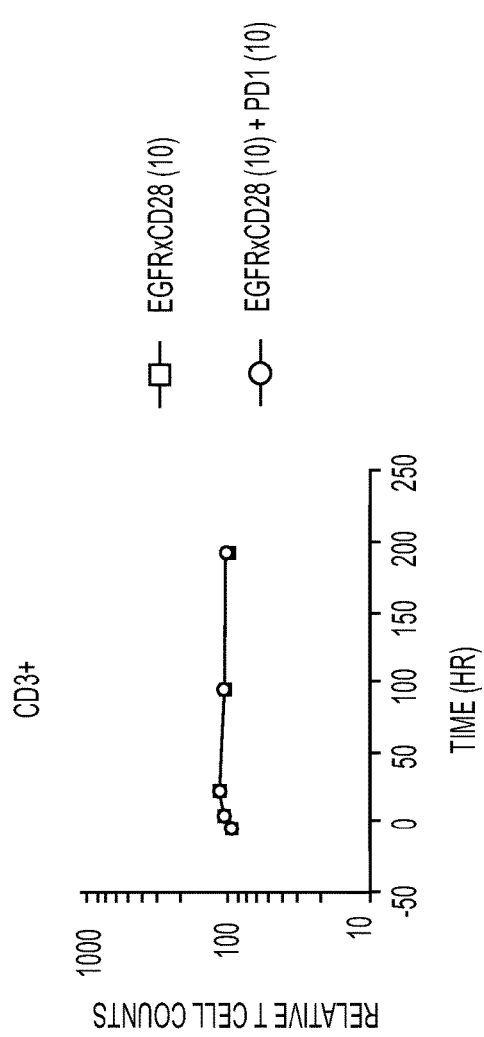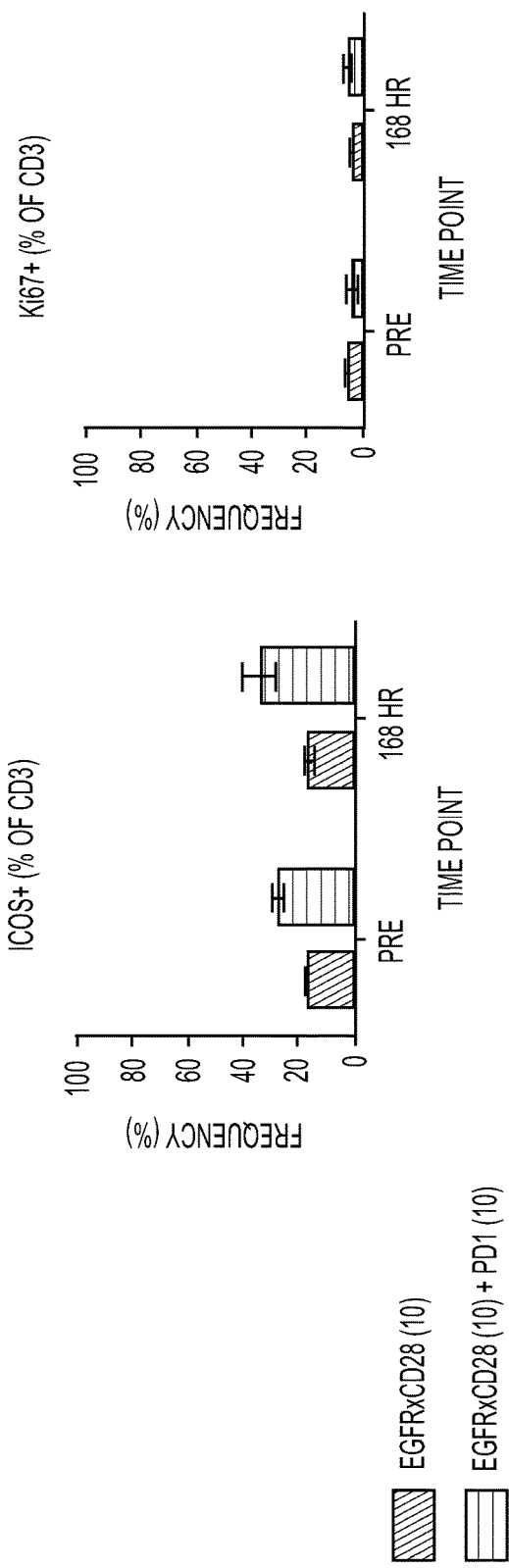
FIG. 10B
FIG. 10C

```
                        SEQUENCE LISTING

Sequence total quantity: 72
SEQ ID NO: 1           moltype = DNA  length = 363
FEATURE                Location/Qualifiers
misc_feature           1..363
                       note = Description of Artificial Sequence:
                       Syntheticpolynucleotide
source                 1..363
                       mol_type = other DNA
                       organism = synthetic construct
SEQUENCE: 1
caggtgcagc tgcaggagtc gggcccagga ctggtgaagc cttcggagac cctgtccctc   60
acctgcactg tctctggtga ctccatcatt actttctact ggagctggat ccggcagccc  120
ccaggagggg gactggagtg gattgggtat atctattaca gtgggatcac caactacaat  180
ccctccctca agagtcgagt caccatatca gtagacacgt ccaagaacca ggtctccctg  240
aaactgagtt ctgtgaccgc tgcggacacg gccgtgtatt attgtgcgag agtgtccgag  300
gattcctact tcactacggg gatggacgtc tggggccaag ggaccacggt caccgtctcc  360
tca                                                                363

SEQ ID NO: 2           moltype = AA  length = 121
FEATURE                Location/Qualifiers
REGION                 1..121
                       note = Description of Artificial Sequence:
                       Syntheticpolypeptide
source                 1..121
                       mol_type = protein
                       organism = synthetic construct
SEQUENCE: 2
QVQLQESGPG LVKPSETLSL TCTVSGDSII TFYWSWIRQP PGRGLEWIGY IYYSGITNYN   60
PSLKSRVTIS VDTSKNQVSL KLSSVTAADT AVYYCARVSE DSYFHYGMDV WGQGTTVTVS  120
S                                                                  121

SEQ ID NO: 3           moltype = DNA  length = 24
FEATURE                Location/Qualifiers
misc_feature           1..24
                       note = Description of Artificial Sequence:
                       Syntheticoligonucleotide
source                 1..24
                       mol_type = other DNA
                       organism = synthetic construct
SEQUENCE: 3
ggtgactcca tcattacttt ctac                                          24

SEQ ID NO: 4           moltype = AA  length = 8
FEATURE                Location/Qualifiers
REGION                 1..8
                       note = Description of Artificial Sequence: Syntheticpeptide
source                 1..8
                       mol_type = protein
                       organism = synthetic construct
SEQUENCE: 4
GDSIITFY                                                            8

SEQ ID NO: 5           moltype = DNA  length = 21
```

```
FEATURE                 Location/Qualifiers
misc_feature            1..21
                        note = Description of Artificial Sequence:
                        Syntheticoligonucleotide
source                  1..21
                        mol_type = other DNA
                        organism = synthetic construct
SEQUENCE: 5
atctattaca gtgggatcac c                                              21

SEQ ID NO: 6            moltype = AA   length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 6
IYYSGIT                                                               7

SEQ ID NO: 7            moltype = DNA   length = 45
FEATURE                 Location/Qualifiers
misc_feature            1..45
                        note = Description of Artificial Sequence:
                        Syntheticoligonucleotide
source                  1..45
                        mol_type = other DNA
                        organism = synthetic construct
SEQUENCE: 7
gcgagagtgt ccgaggattc ctactttcac tacgggatgg acgtc                    45

SEQ ID NO: 8            moltype = AA   length = 15
FEATURE                 Location/Qualifiers
REGION                  1..15
                        note = Description of Artificial Sequence: Syntheticpeptide
source                  1..15
                        mol_type = protein
                        organism = synthetic construct
SEQUENCE: 8
ARVSEDSYFH YGMDV                                                     15

SEQ ID NO: 9            moltype = DNA   length = 366
FEATURE                 Location/Qualifiers
misc_feature            1..366
                        note = Description of Artificial Sequence:
                        Syntheticpolynucleotide
source                  1..366
                        mol_type = other DNA
                        organism = synthetic construct
SEQUENCE: 9
caggtgcagc tgcaggagtc gggcccagga ctggtgaagc cttcggagac cctgtccctc    60
acctgcactg tctctggtgg ctccatcagt agttactact ggagctggat ccggcagccc   120
ccagggaagg gactgagtg gattgggtat atctattaca gtgggatcac ccactacaac    180
ccctccctca agagtcgagt caccatatca gtagacacgt ccaagatcca gttccctg     240
aagctgagtt ctgtgaccgc tgcggacacg gccgtgtatt actgtgcgag atgggggtt    300
cggagggact actactacta cggtatggac gtctggggc aagggaccac ggtcaccgtc    360
tcctca                                                              366

SEQ ID NO: 10           moltype = AA   length = 122
FEATURE                 Location/Qualifiers
REGION                  1..122
                        note = Description of Artificial Sequence:
                        Syntheticpolypeptide
source                  1..122
                        mol_type = protein
                        organism = synthetic construct
SEQUENCE: 10
QVQLQESGPG LVKPSETLSL TCTVSGGSIS SYYWSWIRQP PGKGLEWIGY IYYSGITHYN    60
PSLKSRVTIS VDTSKIQFSL KLSSVTAADT AVYYCARWGV RRDYYYYGMD VWGQGTTVTV   120
SS                                                                  122

SEQ ID NO: 11           moltype = DNA   length = 24
FEATURE                 Location/Qualifiers
misc_feature            1..24
                        note = Description of Artificial Sequence:
                        Syntheticoligonucleotide
source                  1..24
                        mol_type = other DNA
                        organism = synthetic construct
```

```
SEQUENCE: 11
ggtggctcca tcagtagtta ctac                                              24

SEQ ID NO: 12           moltype = AA  length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 12
GGSISSYY                                                                8

SEQ ID NO: 13           moltype = DNA  length = 48
FEATURE                 Location/Qualifiers
misc_feature            1..48
                        note = Description of Artificial Sequence:
                         Syntheticoligonucleotide
source                  1..48
                        mol_type = other DNA
                        organism = synthetic construct
SEQUENCE: 13
gcgagatggg gggttcggag ggactactac tactacggta tggacgtc                    48

SEQ ID NO: 14           moltype = AA  length = 16
FEATURE                 Location/Qualifiers
REGION                  1..16
                        note = Description of Artificial Sequence: Syntheticpeptide
source                  1..16
                        mol_type = protein
                        organism = synthetic construct
SEQUENCE: 14
ARWGVRRDYY YYGMDV                                                       16

SEQ ID NO: 15           moltype = DNA  length = 324
FEATURE                 Location/Qualifiers
misc_feature            1..324
                        note = Description of Artificial Sequence:
                         Syntheticpolynucleotide
source                  1..324
                        mol_type = other DNA
                        organism = synthetic construct
SEQUENCE: 15
gaaatagttt tgacacagag tcccggcaca ctgtcactct ctcccgggga aagagccacc       60
ttgtcatgta gagcaagtca gtcagtctct agctcttatc tcgcctggta ccagcagaag      120
ccgggacagg cccctagact gctgatctac ggggcaagtt ccagggccac cggaatcccc      180
gaccggttca gtgaagcgg aagcggaacc gattttactt tgacgatttc tagactggag       240
ccagaggatt tcgccgttta ctattgtcaa cagtacggaa gcagccgtg gacgtttggc       300
cagggcacga aggtagaaat caag                                             324

SEQ ID NO: 16           moltype = AA  length = 108
FEATURE                 Location/Qualifiers
REGION                  1..108
                        note = Description of Artificial Sequence:
                         Syntheticpolypeptide
source                  1..108
                        mol_type = protein
                        organism = synthetic construct
SEQUENCE: 16
EIVLTQSPGT LSLSPGERAT LSCRASQSVS SSYLAWYQQK PGQAPRLLIY GASSRATGIP       60
DRFSGSGSGT DFTLTISRLE PEDFAVYYCQ QYGSSPWTFG QGTKVEIK                   108

SEQ ID NO: 17           moltype = DNA  length = 21
FEATURE                 Location/Qualifiers
misc_feature            1..21
                        note = Description of Artificial Sequence:
                         Syntheticoligonucleotide
source                  1..21
                        mol_type = other DNA
                        organism = synthetic construct
SEQUENCE: 17
cagtcagtct ctagctctta t                                                 21

SEQ ID NO: 18           moltype = AA  length = 7
FEATURE                 Location/Qualifiers
REGION                  1..7
                        note = Description of Artificial Sequence: Syntheticpeptide
source                  1..7
                        mol_type = protein
```

```
                           organism = synthetic construct
SEQUENCE: 18
QSVSSSY                                                                       7

SEQ ID NO: 19              moltype =    length =
SEQUENCE: 19
000

SEQ ID NO: 20              moltype =    length =
SEQUENCE: 20
000

SEQ ID NO: 21              moltype = DNA  length = 27
FEATURE                    Location/Qualifiers
misc_feature               1..27
                           note = Description of Artificial Sequence:
                           Syntheticoligonucleotide
source                     1..27
                           mol_type = other DNA
                           organism = synthetic construct
SEQUENCE: 21
caacagtacg gaagcagccc gtggacg                                                27

SEQ ID NO: 22              moltype = AA  length = 9
FEATURE                    Location/Qualifiers
REGION                     1..9
                           note = Description of Artificial Sequence: Syntheticpeptide
source                     1..9
                           mol_type = protein
                           organism = synthetic construct
SEQUENCE: 22
QQYGSSPWT                                                                     9

SEQ ID NO: 23              moltype = DNA  length = 1344
FEATURE                    Location/Qualifiers
misc_feature               1..1344
                           note = Description of Artificial Sequence:
                           Syntheticpolynucleotide
source                     1..1344
                           mol_type = other DNA
                           organism = synthetic construct
SEQUENCE: 23
caggtgcagc tgcaggagtc gggcccagga ctggtgaagc cttcggagac cctgtccctc      60
acctgcactg tctctggtga ctccatcatt actttctact ggagctggat ccggcagccc     120
ccagggaggg gactggagtg gattgggtat atctattaca gtgggatcac caactacaat     180
ccctccctca gagtcgagt caccatatca gtagacacgt ccaagaacca ggtctccctg     240
aaactgagtt ctgtgaccgc tgcggacacg gccgtgtatt attgtgcgag agtgtccgag     300
gattcctact ttcactacgg gatgacgtc tggggccaag gaccacggt caccgtctcc     360
tcagcctcca ccaagggccc atcggtcttc cccctggcgc cctgctccag gagcacctcc     420
gagagcacag ccgccctggg ctgcctggtc aaggactact ccccgaacc ggtgacggtg     480
tcgtggaact caggcgccct gaccagcggc gtgcacacct tcccggctgt cctacagtcc     540
tcaggactct actccctcag cagcgtggtg accgtgccct ccagcagctt gggcacgaag     600
acctacacct gcaacgtaga tcacaagccc agcaacacca aggtggacaa gagagttgag     660
tccaaatatg gtcccccatg cccaccgtgc ccagcaccac ctgtggcagg accatcagtc     720
ttcctgttcc cccaaaaacc caaggacact ctcatgatct cccggacccc tgaggtcacg     780
tgcgtggtgg tggacgtgag ccaggaagac cccgaggtcc agttcaactg gtacgtggat     840
ggcgtggagg tgcataatgc caagacaaag ccgcgggagg agcagttcaa cagcacgtac     900
cgtgtggtca gcgtcctcac cgtcctgcac caggactggc tgaacggcaa ggagtacaag     960
tgcaaggtct ccaacaaagg cctcccgtcc tccatcgaga aaaccatctc caaagccaaa     1020
gggcagcccc gagagccaca ggtgtacacc ctgcccccat cccaggagga tgatgaccaag     1080
aaccaggtca gcctgacctg cctggtcaaa ggcttctacc ccagcgacat cgccgtggag     1140
tgggagagca atgggcagcc ggagaacaac tacaagacca cgcctcccgt gctggactcc     1200
gacggctcct tcttcctcta cagcaggctc accgtggaca agagcaggtg gcaggagggg     1260
aatgtcttct catgctccgt gatgcatgag gctctgcaca accactacac acagaagtcc     1320
ctctccctgt ctctgggtaa atga                                            1344

SEQ ID NO: 24              moltype = AA  length = 447
FEATURE                    Location/Qualifiers
REGION                     1..447
                           note = Description of Artificial Sequence:
                           Syntheticpolypeptide
source                     1..447
                           mol_type = protein
                           organism = synthetic construct
SEQUENCE: 24
QVQLQESGPG LVKPSETLSL TCTVSGDSII TFYWSWIRQP PGRGLEWIGY IYYSGITNYN      60
PSLKSRVTIS VDTSKNQVSL KLSSVTAADT AVYYCARVSE DSYFHYGMDV WGQGTTVTVS     120
SASTKGPSVF PLAPCSRSTS ESTAALGCLV KDYFPEPVTV SWNSGALTSG VHTFPAVLQS     180
SGLYSLSSVV TVPSSSLGTK TYTCNVDHKP SNTKVDKRVE SKYGPPCPPC PAPPVAGPSV     240
```

```
FLFPPKPKDT LMISRTPEVT CVVVDVSQED PEVQFNWYVD GEVEHNAKTK PREEQFNSTY   300
RVVSVLTVLH QDWLNGKEYK CKVSNKGLPS SIEKTISKAK GQPREPQVYT LPPSQEEMTK   360
NQVSLTCLVK GFYPSDIAVE WESNGQPENN YKTTPPVLDS DGSFFLYSRL TVDKSRWQEG   420
NVFSCSVMHE ALHNHYTQKS LSLSLGK                                      447

SEQ ID NO: 25          moltype = DNA   length = 1347
FEATURE                Location/Qualifiers
misc_feature           1..1347
                       note = Description of Artificial Sequence:
                         Syntheticpolynucleotide
source                 1..1347
                       mol_type = other DNA
                       organism = synthetic construct
SEQUENCE: 25
caggtgcagc tgcaggagtc gggcccagga ctggtgaagc cttcggagac cctgtccctc    60
acctgcactg tctctggtgg ctccatcagt agttactact ggagctggat ccggcagccc   120
ccagggaagg gactggagtg gattgggtat atctattaca gtgggatcac ccactacaac   180
ccctccctca agagtcgagt caccatatca gtagacacgt ccaagatcca gttctccctg   240
aagctgagtt ctgtgaccgc tgcggacacg gccgtgtatt actgtgcgag atggggggtt   300
cggagggact actactacta cggtatggac gtctggggcc aagggaccac ggtcaccgtc   360
tcctcagcct ctacaaaggg accttctgtg tttcctctgg ctccttgttc tagatctaca   420
tctgaatcta cagctgctct gggatgtctg gtgaaggatt attttcctga acctgtgaca   480
gtgtcttgga attctggagc tctgacatct ggagtgcata catttcctgc tgtgctgcag   540
tcttctggac tgtattctct gtcttctgtg gtgacagtgc cttcttcttc tctgggaaca   600
aagacatata catgtaatgt ggatcataag ccttctaata caaaggtgga taagagagtg   660
gaatctaagt atggaccctc ttgtcctcct tgtcctgctc ctcctgtgtg tggaccttct   720
gtgtttctgt ttcctcctaa gcctaaggat acactgatga tctctagaac acctgaagtg   780
acatgtgtgg tggtggatgt gtctcaggaa gatcctgaag tgcagtttaa ttggtatgtg   840
gatggagtgg aagtgcataa tgctaagaca agcctagag aagaacagtt taattctaca   900
tatagatggt tgtctgtgct gacagtgctg catcaggatt ggctgaatgg aaaggaattac 960
aagtgtaagg tgtctaataa gggactgcct tcttctatcg aaaagacaat ctctaaggct   1020
aagggacagc ctagagaacc tcaggtgtat acactgcctc cttctcagga gaaaatgaca   1080
aagaatcagg tgtctctgac atgtctggtg aagggatttt atccttctga tatcgctgtg   1140
gaatgggaat ctaatggaca gcctgaaaat aattataaga caacacctcc tgtgctggat   1200
tctgatggat ctttttttct gtattctaga ctgacagtgg ataagtctag atggcaggaa   1260
ggaaatgtgt tttcttgttc tgtgatgcat gaagctctgc ataatagatt tacacagaag   1320
tctctgtctc tgtctcctgg aaagtag                                      1347

SEQ ID NO: 26          moltype = AA   length = 448
FEATURE                Location/Qualifiers
REGION                 1..448
                       note = Description of Artificial Sequence:
                         Syntheticpolypeptide
source                 1..448
                       mol_type = protein
                       organism = synthetic construct
SEQUENCE: 26
QVQLQESGPG LVKPSETLSL TCTVSGGSIS SYYWSWIRQP PGKGLEWIGY IYYSGITHYN    60
PSLKSRVTIS VDTSKIQFSL KLSSVTAADT AVYYCARWGV RRDYYYYGMD VWGQGTTVTV   120
SSASTKGPSV FPLAPCSRST SESTAALGCL VKDYFPEPVT VSWNSGALTS GVHTFPAVLQ   180
SSGLYSLSSV VTVPSSSLGT KTYTCNVDHK PSNTKVDKRV ESKYGPPCPP CPAPPVAGPS   240
VFLFPPKPKD TLMISRTPEV TCVVVDVSQE DPEVQFNWYV DGVEVHNAKT KPREEQFNST   300
YRVVSVLTVL HQDWLNGKEY KCKVSNKGLP SSIEKTISKA KGQPREPQVY TLPPSQEEMT   360
KNQVSLTCLV KGFYPSDIAV EWESNGQPEN NYKTTPPVLD SDGSFFLYSR LTVDKSRWQE   420
GNVFSCSVMH EALHNRFTQK SLSLSPGK                                     448

SEQ ID NO: 27          moltype = DNA   length = 648
FEATURE                Location/Qualifiers
misc_feature           1..648
                       note = Description of Artificial Sequence:
                         Syntheticpolynucleotide
source                 1..648
                       mol_type = other DNA
                       organism = synthetic construct
SEQUENCE: 27
gaaatagttt tgacacagag tcccggcaca ctgtcactct ctcccgggga aagagccacc    60
ttgtcatgta gagcaagtca gtcagtctct agctcttatc tcgcctggta ccagcagaag   120
ccgggacagg cccctagact gctgatctac ggggcaagtt ccaggccac cggaatcccc    180
gaccggttca gtggaagcgg aagcggaacc gattttactt ctgacatttc tagactgag    240
ccagaggatt tcgccgttta ctattgtcaa cagtacggaa gcagcccgtg gacgtttggc   300
cagggcacga aggtagaaat caagcgaact gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacaggacaa ggacagcaag gacagcctca acagcaccctg   540
acgctgagca agcagactca gagaaacac aaagtctacg cctgcgaagt cacccatcag   600
ggcctgagct cgcccgtcac aaagagcttc aacaggggag agtgttag                648

SEQ ID NO: 28          moltype = AA   length = 215
FEATURE                Location/Qualifiers
```

```
REGION                  1..215
                        note = Description of Artificial Sequence:
                          Syntheticpolypeptide
source                  1..215
                        mol_type = protein
                        organism = synthetic construct
SEQUENCE: 28
EIVLTQSPGT LSLSPGERAT LSCRASQSVS SSYLAWYQQK PGQAPRLLIY GASSRATGIP    60
DRFSGSGSGT DFTLTISRLE PEDFAVYYCQ QYGSSPWTFG QGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215

SEQ ID NO: 29           moltype = DNA  length = 366
FEATURE                 Location/Qualifiers
misc_feature            1..366
                        note = Description of Artificial Sequence:
                          Syntheticpolynucleotide
source                  1..366
                        mol_type = other DNA
                        organism = synthetic construct
SEQUENCE: 29
gaggtgcagc tggtggagtc tgggggaggc ttggtccggc ctggggggtc cctgagactc    60
tcctgtacag cctctggatt cacccttcagt acctttatta tgttctgggt ccgccaggct   120
ccagggaagg gactggaata tgtttcatcc attagtagta atgggggtac catatattat   180
gcagactctg tgaagggcag attcaccatc tccagagaca attccaagaa cactctatat   240
cttcaaatgg gcagcctgag agctgaggac atggctgtat attattgtac gagaggggc    300
gattttggga gtggttatta tcctttgac tactggggcc agggaaccct ggtcaccgtc    360
tcctca                                                              366

SEQ ID NO: 30           moltype = AA  length = 122
FEATURE                 Location/Qualifiers
REGION                  1..122
                        note = Description of Artificial Sequence:
                          Syntheticpolypeptide
source                  1..122
                        mol_type = protein
                        organism = synthetic construct
SEQUENCE: 30
EVQLVESGGG LVRPGGSLRL SCTASGFTFS TFIMFWVRQA PGKGLEYVSS ISSNGGTIYY    60
ADSVKGRFTI SRDNSKNTLY LQMGSLRAED MAVYYCTRGG DFWSGYYPFD YWGQGTLVTV   120
SS                                                                  122

SEQ ID NO: 31           moltype = DNA  length = 24
FEATURE                 Location/Qualifiers
misc_feature            1..24
                        note = Description of Artificial Sequence:
                          Syntheticoligonucleotide
source                  1..24
                        mol_type = other DNA
                        organism = synthetic construct
SEQUENCE: 31
ggattcacct tcagtacctt tatt                                           24

SEQ ID NO: 32           moltype = AA  length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 32
GFTFSTFI                                                              8

SEQ ID NO: 33           moltype = DNA  length = 24
FEATURE                 Location/Qualifiers
misc_feature            1..24
                        note = Description of Artificial Sequence:
                          Syntheticoligonucleotide
source                  1..24
                        mol_type = other DNA
                        organism = synthetic construct
SEQUENCE: 33
attagtagta atgggggtac cata                                           24

SEQ ID NO: 34           moltype = AA  length = 8
FEATURE                 Location/Qualifiers
REGION                  1..8
                        note = Description of Artificial Sequence: Syntheticpeptide
source                  1..8
```

```
                        mol_type = protein
                        organism = synthetic construct
SEQUENCE: 34
ISSNGGTI                                                                  8

SEQ ID NO: 35           moltype = DNA   length = 45
FEATURE                 Location/Qualifiers
misc_feature            1..45
                        note = Description of Artificial Sequence:
                        Syntheticoligonucleotide
source                  1..45
                        mol_type = other DNA
                        organism = synthetic construct
SEQUENCE: 35
acgagagggg gcgattttg gagtggttat tatccttttg actac              45

SEQ ID NO: 36           moltype = AA    length = 15
FEATURE                 Location/Qualifiers
REGION                  1..15
                        note = Description of Artificial Sequence: Syntheticpeptide
source                  1..15
                        mol_type = protein
                        organism = synthetic construct
SEQUENCE: 36
TRGGDFWSGY YPFDY                                                         15

SEQ ID NO: 37           moltype = DNA   length = 1347
FEATURE                 Location/Qualifiers
misc_feature            1..1347
                        note = Description of Artificial Sequence:
                        Syntheticpolynucleotide
source                  1..1347
                        mol_type = other DNA
                        organism = synthetic construct
SEQUENCE: 37
gaggtgcagc tggtggagtc tgggggaggc ttggtccggc ctggggggtc cctgagactc   60
tcctgtacag cctctggatt caccttcagt acctttatta tgttctgggt ccgccaggct  120
ccagggaagg gactggaata tgtttcatcc attagtagta tgggggtac catatattat  180
gcagactctg tgaagggcag attcaccatc tccagagaca attccaagaa cactctatat  240
cttcaaatgg gcagcctgag agctgaggac atggctgtat attattgtac gagagggggc  300
gattttttgga gtggttatta tccttttgac tactggggcc agggaaccct ggtcaccgtc  360
tcctcagcct ccaccaaggg cccatcggtc ttccccctgg cgccctgctc caggagcacc  420
tccgagagca gcgccctggg ctgcctg gtcaaggact acttccccga accggtgacg  480
gtgtcgtgga actcaggcgc cctgaccagc ggcgtgcaca ccttcccggc tgtcctacag  540
tcctcaggac tctactccct cagcagcgtg gtgaccgtgc cctccagcag cttgggcacg  600
aagacctaca cctgcaacgt agatcacaag cccagcaaca ccaaggtgga caagagagtt  660
gagtccaaat atggtccccc atgcccaccg tgcccagcac ctgtgcc aggaccatca  720
gtcttcctgt tccccccaaa acccaaggac actctcatga tctcccggac ccctgaggtc  780
acgtgcgtgg tggtggacgt gagccaggaa gaccccgagg tccagttcaa ctggtacgtg  840
gatggcgtgg aggtgcataa tgccaagaca aagccgcggg aggagcagtt caacagcacg  900
taccgtgtgg tcagcgtcct caccgtcctg caccaggact ggctgaacgg caaggagtac  960
aagtgcaagg tctccaacaa aggcctcccg tcctccatcg agaaaaccat ctccaaagcc  1020
aaagggcagc cccgagagcc acaggtgtac accctgcccc catcccagga ggagatgacc  1080
aagaaccagg tcagcctgac ctgcctggtc aaaggcttct accccagcga catcgccgtg  1140
gagtgggaga gcaatgggca gccggagaac aactacaaga ccacgcctcc cgtgctggac  1200
tccgacggct ccttcttcct ctacagcagg ctcaccgtgg acaagagcag gtggcaggaa  1260
gggaatgtct tctcatgctc cgtgatgcat gaggctctgc acaaccacta cacacagaag  1320
tccctctccc tgtctctggg taaatga                                      1347

SEQ ID NO: 38           moltype = AA    length = 448
FEATURE                 Location/Qualifiers
REGION                  1..448
                        note = Description of Artificial Sequence:
                        Syntheticpolypeptide
source                  1..448
                        mol_type = protein
                        organism = synthetic construct
SEQUENCE: 38
EVQLVESGGG LVRPGGSLRL SCTASGFTFS TFIMFWVRQA PGKGLEYVSS ISSNGGTIYY    60
ADSVKGRFTI SRDNSKNTLY LQMGSLRAED MAVYYCTRGG DFWSGYYPFD YWGQGTLVTV   120
SSASTKGPSV FPLAPCSRST SESTAALGCL VKDYFPEPVT VSWNSGALTS GVHTFPAVLQ   180
SSGLYSLSSV VTVPSSSLGT KTYTCNVDHK PSNTKVDKRV ESKYGPPCPP CPAPPVAGPS   240
VFLFPPKPKD TLMISRTPEV TCVVVDVSQE DPEVQFNWYV DGVEVHNAKT KPREEQFNST   300
YRVVSVLTVL HQDWLNGKEY KCKVSNKGLP SSIEKTISKA KGQPREPQVY TLPPSQEEMT   360
KNQVSLTCLV KGFYPSDIAV EWESNGQPEN NYKTTPPVLD SDGSFFLYSR LTVDKSRWQE   420
GNVFSCSVMH EALHNHYTQK SLSLSLGK                                     448

SEQ ID NO: 39           moltype = DNA   length = 378
FEATURE                 Location/Qualifiers
```

-continued

```
misc_feature         1..378
                     note = Description of Artificial Sequence:
                       Syntheticpolynucleotide
source               1..378
                     mol_type = other DNA
                     organism = synthetic construct
SEQUENCE: 39
gaggtgcagc tggtggagtc tgggggaggc ttggtaaagc ctgggggtc ccttagactc    60
tcctgtacag cctccggatt ctccttcaga gacgcctgga tgacctgggt ccgccaggtt  120
ccagggaagg ggctggagtg ggttggccgt attaggaaca aaattgatgg tgggacgaca  180
gactacaata cacccgtgaa agacagattc accatctcaa gagatgattc aaaaaacacg  240
ctgtatctgc aaatgaacag cctgaaaacc gaggacacag ccgtgtatta ttgtaccaca  300
gatatttgga actacgttct cttctactac tacggtttgg acgtctgggg ccaagggacc  360
acggtcaccg tctcctca                                                 378

SEQ ID NO: 40        moltype = AA   length = 126
FEATURE              Location/Qualifiers
REGION               1..126
                     note = Description of Artificial Sequence:
                       Syntheticpolypeptide
source               1..126
                     mol_type = protein
                     organism = synthetic construct
SEQUENCE: 40
EVQLVESGGG LVKPGGSLRL SCTASGFSFR DAWMTWVRQV PGKGLEWVGR IRNKIDGGTT    60
DYNTPVKDRF TISRDDSKNT LYLQMNSLKT EDTAVYYCTT DIWNYVLFYY YGLDVWGQGT   120
TVTVSS                                                               126

SEQ ID NO: 41        moltype = DNA   length = 24
FEATURE              Location/Qualifiers
misc_feature         1..24
                     note = Description of Artificial Sequence:
                       Syntheticoligonucleotide
source               1..24
                     mol_type = other DNA
                     organism = synthetic construct
SEQUENCE: 41
ggattctcct tcagagacgc ctgg                                            24

SEQ ID NO: 42        moltype = AA   length = 8
FEATURE              Location/Qualifiers
REGION               1..8
                     note = Description of Artificial Sequence: Syntheticpeptide
source               1..8
                     mol_type = protein
                     organism = synthetic construct
SEQUENCE: 42
GFSFRDAW                                                               8

SEQ ID NO: 43        moltype = DNA   length = 30
FEATURE              Location/Qualifiers
misc_feature         1..30
                     note = Description of Artificial Sequence:
                       Syntheticoligonucleotide
source               1..30
                     mol_type = other DNA
                     organism = synthetic construct
SEQUENCE: 43
attaggaaca aaattgatgg tgggacgaca                                      30

SEQ ID NO: 44        moltype = AA   length = 10
FEATURE              Location/Qualifiers
REGION               1..10
                     note = Description of Artificial Sequence: Syntheticpeptide
source               1..10
                     mol_type = protein
                     organism = synthetic construct
SEQUENCE: 44
IRNKIDGGTT                                                            10

SEQ ID NO: 45        moltype = DNA   length = 51
FEATURE              Location/Qualifiers
misc_feature         1..51
                     note = Description of Artificial Sequence:
                       Syntheticoligonucleotide
source               1..51
                     mol_type = other DNA
                     organism = synthetic construct
SEQUENCE: 45
```

```
accacagata tttggaacta cgttctcttc tactactacg gtttggacgt c                51

SEQ ID NO: 46           moltype = AA  length = 17
FEATURE                 Location/Qualifiers
REGION                  1..17
                        note = Description of Artificial Sequence: Syntheticpeptide
source                  1..17
                        mol_type = protein
                        organism = synthetic construct
SEQUENCE: 46
TTDIWNYVLF YYYGLDV                                                      17

SEQ ID NO: 47           moltype = DNA  length = 1359
FEATURE                 Location/Qualifiers
misc_feature            1..1359
                        note = Description of Artificial Sequence:
                        Syntheticpolynucleotide
source                  1..1359
                        mol_type = other DNA
                        organism = synthetic construct
SEQUENCE: 47
gaggtgcagc tggtggagtc tgggggaggc ttggtaaagc ctggggggtc ccttagactc        60
tcctgtacag cctccggatt ctccttcaga gacgcctgga tgacctgggt ccgccaggtt       120
ccagggaagg ggctggagtg ggttggccgt attaggaaca aaattgatgg tgggacgaca       180
gactacaata cacccgtgaa agacagattc accatctcaa gagatgattc aaaaaacacg       240
ctgtatctgc aaatgaacag cctgaaaacc gaggacacgc ccgtgtatta ttgtaccaca       300
gatatttgga actacgttct cttctactac tacggtttgg acgtctgggg ccaagggacc       360
acggtcaccg tctcctcagc ctccaccaag ggcccatcgg tcttcccccct ggcgccctgc     420
tccaggagca cctccgagag cacagccgcc ctgggctgcc tggtcaagga ctacttcccc       480
gaaccggtga cggtgtcgtg gaactcaggc gccctgacca gcggcgtgca caccttcccg       540
gctgtcctac agtcctcagg actctactcc ctcagcagcg tggtgaccgt gccctccagc       600
agcttgggca cgaagaccta cacctgcaac gtagatcaca agcccagcaa caccaaggtg       660
gacaagagag ttgagtccaa atatggtccc ccatgcccac cgtgcccagc accacctgtg       720
gcaggaccat cagtcttcct gttccccccca aaacccaagg acactctcat gatctcccgg     780
acccctgagg tcacgtgcgt ggtggtggac gtgagccacg aagaccccga ggtccagttc       840
aactggtacg tggatggcgt ggaggtgcat aatgccaaga caaagccgcg ggaggagcag       900
ttcaacagca cgtaccgtgt ggtcagcgtc ctcaccgtcc tgcaccagga ctggctgaac       960
ggcaaggagt acaagtgcaa ggtctccaac aaaggcctcc cgtcctccat cgagaaaacc      1020
atctccaaag ccaaagggca gccccgagag ccacaggtgt acaccctgcc cccatcccag      1080
gaggagatga ccaagaacca ggtcagcctg acctgcctgg tcaaaggctt ctaccccagc      1140
gacatcgccg tggagtggga gagcaatggg cagccggaga acaactacaa gaccacgcct      1200
cccgtgctgg actccgacgg ctccttcttc ctctacagca ggctcaccgt ggacaagagc      1260
aggtggcagg aggggaatgt cttctcatgc tccgtgatgc atgaggctct gcacaaccac      1320
tacacacaga agtccctctc cctgtctctg ggtaaatga                             1359

SEQ ID NO: 48           moltype = AA  length = 452
FEATURE                 Location/Qualifiers
REGION                  1..452
                        note = Description of Artificial Sequence:
                        Syntheticpolypeptide
source                  1..452
                        mol_type = protein
                        organism = synthetic construct
SEQUENCE: 48
EVQLVESGGG LVKPGGSLRL SCTASGFSFR DAWMTWVRQV PGKGLEWVGR IRNKIDGGTT        60
DYNTPVKDRF TISRDDSKNT LYLQMNSLKT EDTAVYYCTT DIWNYVLFYY YGLDVWGQGT       120
TVTVSSASTK GPSVFPLAPC SRSTSESTAA LGCLVKDYFP EPVTVSWNSG ALTSGVHTFP       180
AVLQSSGLYS LSSVVTVPSS SLGTKTYTCN VDHKPSNTKV DKRVESKYGP PCPPCPAPPV       240
AGPSVFLFPP KPKDTLMISR TPEVTCVVVD VSQEDPEVQF NWYVDGVEVH NAKTKPREEQ       300
FNSTYRVVSV LTVLHQDWLN GKEYKCKVSN KGLPSSIEKT ISKAKGQPRE PQVYTLPPSQ       360
EEMTKNQVSL TCLVKGFYPS DIAVEWESNG QPENNYKTTP PVLDSDGSFF LYSRLTVDKS       420
RWQEGNVFSC SVMHEALHNH YTQKSLSLSL GK                                    452

SEQ ID NO: 49           moltype = DNA  length = 363
FEATURE                 Location/Qualifiers
misc_feature            1..363
                        note = Description of Artificial Sequence:
                        Syntheticpolynucleotide
source                  1..363
                        mol_type = other DNA
                        organism = synthetic construct
SEQUENCE: 49
caggtgcagc tgcaggagtc gggcccagga ctggtgaagc cttcggagac cctgtccctc        60
acctgcactg tctctgatga ctccatcatt agttactact ggagctggat ccggcagccc       120
ccagggaagg gactgaatg gattggatat atctattaca gtgggcgcac caactacaac        180
ccctccctca agagtcgagt caccatatca gtagacacgt ccaagaacca ggtctcactg       240
aagctgaact ctgtgattgc tgcggacacg gccgtgtatt actgtgcgag agtgtccgag       300
gattcctact accactacgg tatggacgtc tggggccaag gaccacggt caccgtctcc       360
tca                                                                    363
```

```
SEQ ID NO: 50            moltype = AA   length = 121
FEATURE                  Location/Qualifiers
REGION                   1..121
                         note = Description of Artificial Sequence:
                          Syntheticpolypeptide
source                   1..121
                         mol_type = protein
                         organism = synthetic construct
SEQUENCE: 50
QVQLQESGPG LVKPSETLSL TCTVSDDSII SYYWSWIRQP PGKGLEWIGY IYYSGRTNYN    60
PSLKSRVTIS VDTSKNQVSL KLNSVIAADT AVYYCARVSE DSYYHYGMDV WGQGTTVTVS   120
S                                                                  121

SEQ ID NO: 51            moltype = DNA   length = 24
FEATURE                  Location/Qualifiers
misc_feature             1..24
                         note = Description of Artificial Sequence:
                          Syntheticoligonucleotide
source                   1..24
                         mol_type = other DNA
                         organism = synthetic construct
SEQUENCE: 51
gatgactcca tcattagtta ctac                                          24

SEQ ID NO: 52            moltype = AA   length = 8
FEATURE                  Location/Qualifiers
REGION                   1..8
                         note = Description of Artificial Sequence: Syntheticpeptide
source                   1..8
                         mol_type = protein
                         organism = synthetic construct
SEQUENCE: 52
DDSIISYY                                                            8

SEQ ID NO: 53            moltype = DNA   length = 21
FEATURE                  Location/Qualifiers
misc_feature             1..21
                         note = Description of Artificial Sequence:
                          Syntheticoligonucleotide
source                   1..21
                         mol_type = other DNA
                         organism = synthetic construct
SEQUENCE: 53
atctattaca gtgggcgcac c                                             21

SEQ ID NO: 54            moltype = AA   length = 7
FEATURE                  Location/Qualifiers
REGION                   1..7
                         note = Description of Artificial Sequence: Syntheticpeptide
source                   1..7
                         mol_type = protein
                         organism = synthetic construct
SEQUENCE: 54
IYYSGRT                                                             7

SEQ ID NO: 55            moltype = DNA   length = 45
FEATURE                  Location/Qualifiers
misc_feature             1..45
                         note = Description of Artificial Sequence:
                          Syntheticoligonucleotide
source                   1..45
                         mol_type = other DNA
                         organism = synthetic construct
SEQUENCE: 55
gcgagagtgt ccgaggattc ctactaccac tacggtatgg acgtc                   45

SEQ ID NO: 56            moltype = AA   length = 15
FEATURE                  Location/Qualifiers
REGION                   1..15
                         note = Description of Artificial Sequence: Syntheticpeptide
source                   1..15
                         mol_type = protein
                         organism = synthetic construct
SEQUENCE: 56
ARVSEDSYYH YGMDV                                                    15

SEQ ID NO: 57            moltype = DNA   length = 1344
FEATURE                  Location/Qualifiers
```

```
misc_feature            1..1344
                        note = Description of Artificial Sequence:
                          Syntheticpolynucleotide
source                  1..1344
                        mol_type = other DNA
                        organism = synthetic construct
SEQUENCE: 57
caggtgcagc tgcaggagtc gggcccagga ctggtgaagc cttcggagac cctgtccctc    60
acctgcactg tctctgatga ctccatcatt agttactact ggagctggat ccggcagccc   120
ccagggaagg gactggaatg gattggatat atctattaca gtgggcgcac caactacaac   180
ccctccctca agagtcgagt caccatatca gtagacacgt ccaagaacca ggtctcactg   240
aagctgaact ctgtgattgc tgcggacacg gccgtgtatt actgtgcgag agtgtccgag   300
gattcctact accactacgg tatggacgtc tggggccaag gcaccacggt caccgtctcc   360
tcagcctcca ccaagggccc atcggtcttc cccctggcgc cctgctccag gagcacctcc   420
gagagcacag ccgccctggg ctgcctggtc aaggactact tccccgaacc ggtgacggtg   480
tcgtggaact caggcgccct gaccagcggc gtgcacacct tcccggctgt cctacagtcc   540
tcaggactct actccctcag cagcgtggtg accgtgccct ccagcagctt gggcacgaag   600
acctacacct gcaacgtaga tcacaagccc agcaacacca aggtggacaa gagagttgag   660
tccaaatatg gtccccccatg cccaccgtgc ccagcaccac ctgtggcagg accatcagtc   720
ttcctgttcc ccccaaaacc caaggacact ctcatgatct cccggacccc tgaggtcacg   780
tgcgtggtgg tggacgtgag ccaggaagac cccgaggtcc agttcaactg gtacgtggat   840
ggcgtggagg tgcataatgc caagacaaag ccgcgggagg agcagttcaa cagcacgtac   900
cgtgtggtca gcgtcctcac cgtcctgcac caggactggc tgaacggcaa ggagtacaag   960
tgcaaggtct ccaacaaagg cctcccgtcc tccatcgaga aaaccatctc caaagccaaa  1020
gggcagcccc gagagccaca ggtgtacacc ctgcccccat cccaggagga gatgaccaag  1080
aaccaggtca gcctgacctg cctggtcaaa ggcttctacc ccagcgacat cgccgtggag  1140
tgggagagca atgggcagcc ggagaacaac tacaagacca cgcctcccgt gctggactcc  1200
gacggctcct tcttcctcta cagcaggctc accgtggaca agagcaggtg gcaggagggg  1260
aatgtcttct catgctccgt gatgcatgag gctctgcaca accactacac acagaagtcc  1320
ctctccctgt ctctgggtaa atga                                         1344

SEQ ID NO: 58           moltype = AA  length = 447
FEATURE                 Location/Qualifiers
REGION                  1..447
                        note = Description of Artificial Sequence:
                          Syntheticpolypeptide
source                  1..447
                        mol_type = protein
                        organism = synthetic construct
SEQUENCE: 58
QVQLQESGPG LVKPSETLSL TCTVSDDSII SYYWSWIRQP PGKGLEWIGY IYYSGRTNYN    60
PSLKSRVTIS VDTSKNQVSL KLNSVIAADT AVYYCARVSE DSYYHYGMDV WGQGTTVTVS   120
SASTKGPSVF PLAPCSRSTS ESTAALGCLV KDYFPEPVTV SWNSGALTSG VHTFPAVLQS   180
SGLYSLSSVV TVPSSSLGTK TYTCNVDHKP SNTKVDKRVE SKYGPPCPPC PAPPVAGPSV   240
FLFPPKPKDT LMISRTPEVT CVVVDVSQED PEVQFNWYVD GVEVHNAKTK PREEQFNSTY   300
RVVSVLTVLH QDWLNGKEYK CKVSNKGLPS SIEKTISKAK GQPREPQVYT LPPSQEEMTK   360
NQVSLTCLVK GFYPSDIAVE WESNGQPENN YKTTPPVLDS DGSFFLYSRL TVDKSRWQEG   420
NVFSCSVMHE ALHNHYTQKS LSLSLGK                                      447

SEQ ID NO: 59           moltype = AA  length = 124
FEATURE                 Location/Qualifiers
REGION                  1..124
                        note = Description of Artificial Sequence:
                          Syntheticpolypeptide
source                  1..124
                        mol_type = protein
                        organism = synthetic construct
SEQUENCE: 59
QVQLVESGGG VVQPGRSLRL SCAASGFTFS SYGMHWVRQA PGKGLEWVAV ISYAGNNKYY    60
ADSVKGRFTV SRDNSKKTLY LQMNSLRSED TAVYYCAKDS YYDFLTDPDV LDIWGQGTMV   120
TVSS                                                                124

SEQ ID NO: 60           moltype = AA  length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 60
GFTFSSYG                                                             8

SEQ ID NO: 61           moltype = AA  length = 8
FEATURE                 Location/Qualifiers
REGION                  1..8
                        note = Description of Artificial Sequence: Syntheticpeptide
source                  1..8
                        mol_type = protein
                        organism = synthetic construct
```

```
SEQUENCE: 61
ISYAGNNK                                                                    8

SEQ ID NO: 62           moltype = AA  length = 17
FEATURE                 Location/Qualifiers
REGION                  1..17
                        note = Description of Artificial Sequence: Syntheticpeptide
source                  1..17
                        mol_type = protein
                        organism = synthetic construct
SEQUENCE: 62
AKDSYYDFLT DPDVLDI                                                         17

SEQ ID NO: 63           moltype = AA  length = 118
FEATURE                 Location/Qualifiers
REGION                  1..118
                        note = Description of Artificial Sequence:
                        Syntheticpolypeptide
source                  1..118
                        mol_type = protein
                        organism = synthetic construct
SEQUENCE: 63
EVQLVESGGG LVQPGGSLRL SCAASGFTFS RNNMHWVRQA PGKGLEYVSG ISSNGGRTYY           60
ADSVKGRFTI SRDNSKNTLY LQMGGLRAAD MAVYFCTRDD ELLSFDYWGQ GTLVTVSS           118

SEQ ID NO: 64           moltype = AA  length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 64
GFTFSRNN                                                                    8

SEQ ID NO: 65           moltype = AA  length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 65
ISSNGGRT                                                                    8

SEQ ID NO: 66           moltype = AA  length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 66
TRDDELLSFD Y                                                               11

SEQ ID NO: 67           moltype = AA  length = 108
FEATURE                 Location/Qualifiers
REGION                  1..108
                        note = Description of Artificial Sequence:
                        Syntheticpolypeptide
source                  1..108
                        mol_type = protein
                        organism = synthetic construct
SEQUENCE: 67
DIQMTQSPSS LSASVGDRVT ITCRASQSIS SYLNWYQQKP GKAPKLLIYA ASSLQSGVPS           60
RFSGSGSGTD FTLTISSLQP EDFATYYCQQ SYSTPPITFG QGTRLEIK                      108

SEQ ID NO: 68           moltype = AA  length = 6
FEATURE                 Location/Qualifiers
REGION                  1..6
                        note = Description of Artificial Sequence: Synthetic6xHis
                        tag
source                  1..6
                        mol_type = protein
                        organism = synthetic construct
SEQUENCE: 68
HHHHHH                                                                      6

SEQ ID NO: 69           moltype = AA  length = 660
```

```
FEATURE                 Location/Qualifiers
REGION                  1..660
                        note = Description of Artificial Sequence:
                        Syntheticpolypeptide
source                  1..660
                        mol_type = protein
                        organism = synthetic construct
SEQUENCE: 69
LEEKKVCQGT SNKLTQLGTF EDHFLSLQRM FNNCEVVLGN LEITYVQRNY DLSFLKTIQE    60
VAGYVLIALN TVERIPLENL QIIRGNMYYE NSYALAVLSN YDANKTGLKE LPMRNLQEIL   120
HGAVRFSNNP ALCNVESIQW RDIVSSDFLS NMSMDFQNHL GSCQKCDPSC PNGSCWGAGE   180
ENCQKLTKII CAQQCSGRCR GKSPSDCCHN QCAAGCTGPR ESDCLVCRKF RDEATCKDTC   240
PPLMLYNPTT YQMDVNPEGK YSFGATCVKK CPRNYVVTDH GSCVRACGAD SYEMEEDGVR   300
KCKKCEGPCR KVCNGIGIGE FKDSLSINAT NIKHFKNCTS ISGDLHILPV AFRGDSFTHT   360
PPLDPQELDI LKTVKEITGF LLIQAWPENR TDLHAFENLE IIRGRTKQHG QFSLAVVSLN   420
ITSLGLRSLK EISDGDVIIS GNKNLCYANT INWKKLFGTS GQKTKIISNR GENSCKATGQ   480
VCHALCSPEG CWGPEPRDCV SCRNVSRGRE CVDKCNLLEG EPREFVENSE CIQCHPECLP   540
QAMNITCTGR GPDNCIQCAH YIDGPHCVKT CPAGVMGENN TLVWKYADAG HVCHLCHPNC   600
TYGCTGPGLE GCPTNGPKIP SIACPGGEQK LISEEDLGGE QKLISEEDLS GHHHHHHSSG   660

SEQ ID NO: 70           moltype = AA  length = 24
FEATURE                 Location/Qualifiers
REGION                  1..24
                        note = Description of Artificial Sequence:
                        Syntheticpolypeptide
source                  1..24
                        mol_type = protein
                        organism = synthetic construct
SEQUENCE: 70
LHILPVAFRG DSFTHTPPLD PQEL                                           24

SEQ ID NO: 71           moltype = AA  length = 18
FEATURE                 Location/Qualifiers
REGION                  1..18
                        note = Description of Artificial Sequence:
                        Syntheticpolypeptide
source                  1..18
                        mol_type = protein
                        organism = synthetic construct
SEQUENCE: 71
LEIIRGRTKQ HGQFSLAV                                                  18

SEQ ID NO: 72           moltype = AA  length = 22
FEATURE                 Location/Qualifiers
REGION                  1..22
                        note = Description of Artificial Sequence:
                        Syntheticpolypeptide
source                  1..22
                        mol_type = protein
                        organism = synthetic construct
SEQUENCE: 72
CNVESIQWRD IVSSDFLSNM SM                                             22
```

EGFR X CD28 MULTISPECIFIC ANTIBODIES

RELATED APPLICATIONS

This application is a continuation of U.S. patent application Ser. No. 16/825,179, filed on Mar. 20, 2020, which is related to and claims priority of U.S. Provisional Application No. 62/822,124, filed on Mar. 22, 2019. The entire contents of each of the foregoing applications, including drawings and sequence listings, are expressly incorporated herein by reference.

FIELD OF THE INVENTION

The present invention relates to antibodies that bind to EGF receptor and CD28 and methods of use thereof, e.g., for treating or preventing cancer.

SEQUENCE LISTING

The instant application contains a Sequence Listing XML which has been submitted electronically in XML format and is hereby incorporated by reference in its entirety. Said XML copy, created on Feb. 6, 2023, is named 118003-10603.xml and is 105,147 bytes in size.

BACKGROUND OF THE INVENTION

The ability of T-cells to recognize and kill their cellular targets—such as virally-infected cells or tumor cells—depends on a coordinated set of interactions. Foremost among these is the recognition and binding of the target cell by the T-cell Receptor (TCR) complex (which includes the associated CD3 γ, δ, ε and ζ chains), and this interaction has been referred to as "signal 1" for T-cell activation. The TCR recognizes a viral or tumor peptide presented on the groove of an MHC protein expressed on the surface of the target cell. Because such binding is generally of low-affinity, successful triggering of "signal 1" requires clustering of many TCR complexes along the interface between the T-cell and its target cell; this interface has been referred to as the "immune synapse". T-cell activation can be further promoted by additional interactions. For example, T-cells have a molecule referred to as CD28 on their surface, which can provide a co-stimulatory "signal 2" to augment the activation via the TCR complex. When a T-cell recognizes its target cell via its TCR complex, and then also engages "signal 2" via CD28 binding to its cognate ligand(s) on the target cell, T-cell activation is enhanced; as with "signal 1", CD28-mediated "signal 2" is thought to occur via co-clustering at the immune synapse.

Agonistic anti-CD28 mAbs can be applied in sustained ex vivo expansion of cultured T-cells; however, the use of antibodies against CD28 has been discouraged as a result of a series of acute and serious adverse events in a phase I clinical trial where super agonist anti-CD28 mAb was tested systemically (Hünig, Nature Reviews Immunology. 2012; 12:317-318). Localized or targeted use of anti-CD28 mAb can be used with less risk for promotion of antitumor immunity. Jung et al., Int J Cancer. 2001 Jan. 15; 91(2):225-30.

Different families of growth factors and growth factor receptors have been shown to be involved in the autonomous growth of cancer cells. Among these, the epidermal growth factor receptor (EGFR) and the EGF-family of peptide growth factor have a central role in the pathogenesis and progression of different carcinoma types. EGFR belongs to a family of receptors that encompasses three additional proteins, ErbB-2, ErbB-3 and ErbB-4. These proteins and the growth factors of the EGF family form an integrated system in which a signal that hits an individual receptor type is often transmitted to other receptors of the same family.

Monoclonal antibodies (mAbs) aimed at enhancing T-cell activation are under clinical development as anti-tumor therapeutics. The majority of current treatments, however, have a difficult time overcoming the inhibitory nature of the tumor microenvironment, thus failing to generate efficient tumor-specific T-cell activation and subsequent tumor cell killing. Several blocking mAbs directed against checkpoint inhibitors such as CTLA-4 (cytotoxic T lymphocyte-associated protein) and programmed cell death 1(PD-1)/programmed cell death ligand 1 (PD-L1) have been clinically approved for melanoma, renal cell carcinoma, non-small lung cancer and advanced metastatic cutaneous squamous cell carcinoma. Blocking PD-1 releases the break on T-cell activation, but its efficacy as a single agent often it is not sufficient to get tumor clearance and durable anti-tumor responses.

SUMMARY OF THE INVENTION

The present invention provides an immunotherapeutic modality using bi-specific antibodies targeted against Cluster of Differentiation 28 (CD28) and Epidermal Growth Factor Receptor (EGFR×CD28 or CD28×EGFR) that, when combined with a PD-1 blocking antibody, induce long lived anti-tumor immunity and promote robust intra-tumoral T-cell activation with no signs of systemic cytokine secretion, in both syngeneic and human tumor xenograft models. Toxicology studies in genetically-humanized immunocompetent mice and in cynomolgus monkeys demonstrate that these bi-specifics exhibited some single agent activity and no toxicity on their own or in combination with anti-PD-1 antibody. Collectively, these data suggest that combining this class of CD28-based bi-specifics with PD-1 inhibition may provide safe, biologics solutions with strikingly enhanced, specific and synergistic anti-tumor activity.

In one aspect, the present invention provides an isolated bispecific antigen binding molecule comprising a first antigen-binding domain that binds human CD28 with a $K_D$ of less than about $10^{-6}$M as measured by surface plasmon resonance at 25° C.; and a second antigen-binding domain that specifically binds a human epidermal growth factor receptor (EGFR) on a target tumor cell, with a $K_D$ of less than about $10^{-9}$M as measured by surface plasmon resonance at 25° C.

In another aspect, the isolated bispecific antigen binding molecule demonstrates a costimulatory effect when used in conjunction with an anti-Mucine 16 (MUC16)×CD3 bispecific antibody and tested on target cells expressing EGFR. In one embodiment, the costimulatory effect is shown by one or more of the following: (a) the ability to activate and direct human T cells to kill a target cell expressing EGFR; (b) the ability to upregulate PD-1 on T cells; (c) the ability to increase the release of the cytokines IFN gamma and TNF from PBMC; (d) the ability to deplete tumor cells; or (f) the ability to enhance tumor clearance. In another embodiment, the costimulatory effect is further shown by one or more of the following: (g) activation of NFκB activity in a T cell/APC luciferase-based reporter assay; or (h) measurement of IL-2 cytokine production using a primary CD4⁺ T cell/APC functional assay.

The present invention provides a multispecific (e.g., bi-specific) antigen-binding protein (e.g., antibody or antigen-binding fragment thereof) that binds EGFR and CD28 comprising: (1) an EGFR binding arm comprising: (a) an immunoglobulin chain comprising the HCDRs of a heavy chain variable region that comprises an amino acid sequence set forth in a member selected from the group consisting of SEQ ID NOs: 2, 30, 40 and 50, or a variant thereof; and/or (b) an immunoglobulin chain comprising the LCDRs of a light chain variable region that comprises an amino acid sequence set forth in SEQ ID NO: 16, or a variant thereof; and a CD28 binding arm; or (2) a CD28 binding arm comprising: (c) an immunoglobulin chain comprising the HCDRs of a heavy chain variable region that comprises an amino acid sequence set forth in a member selected from the group consisting of SEQ ID NOs: 10, 59 and 63, or a variant thereof; and/or (d) an immunoglobulin chain comprising the LCDRs of a light chain variable region that comprises an amino acid sequence set forth in a member selected from the group consisting of SEQ ID NOs: 16 and 67, or a variant thereof; and an EGFR binding arm.

For example, in an embodiment of the invention, the multispecific (e.g., bi-specific) antigen-binding protein (e.g., antibody or antigen-binding fragment thereof) that binds EGFR and CD28 includes: (1) an EGFR binding arm comprising: (a) a heavy chain immunoglobulin or variable region thereof comprising an amino acid sequence having at least 90% amino acid sequence identity to the amino acid sequence set forth in SEQ ID NOs: 2, 24, 30, 40 and 50, or a variant thereof; and/or (b) a light chain immunoglobulin or variable region thereof comprising an amino acid sequence having at least 90% amino acid sequence identity to the amino acid sequence set forth in SEQ ID NOs: 16 and 28, or a variant thereof; and a CD28 binding arm; or (2) a CD28 binding arm comprising: (c) a heavy chain immunoglobulin or variable region thereof comprising an amino acid sequence having at least 90% amino acid sequence identity to the amino acid sequence set forth in SEQ ID NOs: 10, 26, 59 and 63, or a variant thereof; and/or (d) a light chain immunoglobulin or variable region thereof comprising an amino acid sequence having at least 90% amino acid sequence identity to the amino acid sequence set forth in SEQ ID NOs: 16, 28, and 67, or a variant thereof; and an EGFR binding arm.

In an embodiment of the invention, the multispecific antigen-binding protein (e.g., antibody or antigen-binding fragment thereof) that binds EGFR and CD28 includes: (1) an EGFR binding arm comprising: (a) a heavy chain immunoglobulin or variable region thereof comprising the HCDR1, HCDR2 and HCDR3 of a heavy chain variable region comprising an amino acid sequence set forth in SEQ ID NO: 2, 30, 40 or 50, and at least 90% amino acid sequence identity to the amino acid sequence set forth in SEQ ID NO: 2, 30, 40 or 50, respectively; and/or a light chain immunoglobulin or variable region thereof comprising the LCDR1, LCDR2 and LCDR3 of a light chain variable region comprising an amino acid sequence set forth in SEQ ID NO: 16, and at least 90% amino acid sequence identity to the amino acid sequence set forth in SEQ ID NO: 16, respectively; and a CD28 binding arm; or (2) a CD28 binding arm comprising: (c) a heavy chain immunoglobulin or variable region thereof comprising the HCDR1, HCDR2 and HCDR3 of a heavy chain variable region comprising an amino acid sequence set forth in SEQ ID NO: 10, 59 or 63, and at least 90% amino acid sequence identity to the amino acid sequence set forth in SEQ ID NO: 10, 59 or 63, respectively; and/or (d) a light chain immunoglobulin or variable region thereof comprising the LCDR1, LCDR2 and LCDR3 of a light chain variable region comprising an amino acid sequence set forth in SEQ ID NO: 16, or 67, and at least 90% amino acid sequence identity to the amino acid sequence set forth in SEQ ID NO: 16, or 67, respectively; and an EGFR binding arm.

In an embodiment of the invention, the multispecific (e.g., bi-specific) antigen-binding protein (e.g., antibody or antigen-binding fragment thereof) that binds EGFR and CD28 includes:

(1)
an EGFR binding arm that comprises: a CDR-H1 that comprises the amino acid sequence: GDSIITFY (SEQ ID NO: 4; or a variant thereof); a CDR-H2 that comprises the amino acid sequence: IYYSGIT (SEQ ID NO: 6; or a variant thereof); and a CDR-H3 that comprises the amino acid sequence: ARVSEDSYFHYGMDV (SEQ ID NO: 8; or a variant thereof); and a CDR-L1 that comprises the amino acid sequence: QSVSSSY (SEQ ID NO: 18; or a variant thereof); a CDR-L2 that comprises the amino acid sequence: GAS (or a variant thereof); and a CDR-L3 that comprises the amino acid sequence: QQYGSSPWT (SEQ ID NO: 22; or a variant thereof); and a CD28 binding arm that comprises:
a CDR-H1 that comprises the amino acid sequence: GGSISSYY (SEQ ID NO: 12; or a variant thereof); a CDR-H2 that comprises the amino acid sequence: IYYSGIT (SEQ ID NO: 6; or a variant thereof); and a CDR-H3 that comprises the amino acid sequence: ARWGVRRDYYYYGMDV (SEQ ID NO: 14; or a variant thereof); and a CDR-L1 that comprises the amino acid sequence: QSVSSSY (SEQ ID NO: 18; or a variant thereof);
a CDR-L2 that comprises the amino acid sequence: GAS (or a variant thereof); a CDR-L3 that comprises the amino acid sequence: QQYGSSPWT (SEQ ID NO: 22; or a variant thereof);

(2)
an EGFR binding arm that comprises: a CDR-H1 that comprises the amino acid sequence: GFTFSTFI (SEQ ID NO: 32; or a variant thereof); a CDR-H2 that comprises the amino acid sequence: ISSNGGTI (SEQ ID NO: 34; or a variant thereof); and a CDR-H3 that comprises the amino acid sequence: TRGGDFWSGYYPFDY (SEQ ID NO: 36; or a variant thereof); a CDR-L1 that comprises the amino acid sequence: QSVSSSY (SEQ ID NO: 18; or a variant thereof);
a CDR-L2 that comprises the amino acid sequence: GAS (or a variant thereof); and a CDR-L3 that comprises the amino acid sequence: QQYGSSPWT (SEQ ID NO: 22; or a variant thereof); and a CD28 binding arm that comprises: a CDR-H1 that comprises the amino acid sequence: GGSISSYY (SEQ ID NO: 12; or a variant thereof); a CDR-H2 that comprises the amino acid sequence: IYYSGIT (SEQ ID NO: 6; or a variant thereof); a CDR-H3 that comprises the amino acid sequence: ARWGVRRDYYYYGMDV (SEQ ID NO: 14; or a variant thereof);
and a CDR-L1 that comprises the amino acid sequence: QSVSSSY (SEQ ID NO: 18; or a variant thereof); a CDR-L2 that comprises the amino acid sequence: GAS (or a variant thereof); and a CDR-L3 that comprises the amino acid sequence: QQYGSSPWT (SEQ ID NO: 22; or a variant thereof);

(3)
an EGFR binding arm that comprises: a CDR-H1 that comprises the amino acid sequence: GFSFRDAW (SEQ ID NO: 42; or a variant thereof); a CDR-H2 that comprises the amino acid sequence: IRNKIDGGTT (SEQ ID NO: 44; or a variant thereof); and a CDR-H3 that comprises the amino acid sequence: TTDIWNYVLFYYYGLDV (SEQ ID NO: 46; or a variant thereof); and a CDR-L1 that comprises the amino acid sequence: QSVSSSY (SEQ ID NO: 18; or a variant thereof); a CDR-L2 that comprises the amino acid sequence: GAS (or a variant thereof); and a CDR-L3 that comprises the amino acid sequence: QQYGSSPWT (SEQ ID NO: 22; or a variant thereof) and a CD28 binding arm that comprises: a CDR-H1 that comprises the amino acid sequence: GGSISSYY (SEQ ID NO: 12; or a variant thereof); a CDR-H2 that comprises the amino acid sequence: IYYSGIT (SEQ ID NO: 6; or a variant thereof); and a CDR-H3 that comprises the amino acid sequence: ARWGVRRDYYYYGMDV (SEQ ID NO: 14; or a variant thereof); and a CDR-L1 that comprises the amino acid sequence: QSVSSSY (SEQ ID NO: 18; or a variant thereof); a CDR-L2 that comprises the amino acid sequence: GAS (or a variant thereof); and a CDR-L3 that comprises the amino acid sequence: QQYGSSPWT (SEQ ID NO: 22; or a variant thereof);

(4)
an EGFR binding arm that comprises: a CDR-H1 that comprises the amino acid sequence: DDSIISYY (SEQ ID NO: 52; or a variant thereof); a CDR-H2 that comprises the amino acid sequence: IYYSGRT (SEQ ID NO: 54; or a variant thereof); and a CDR-H3 that comprises the amino acid sequence: ARVSEDSYY-HYGMDV (SEQ ID NO: 56; or a variant thereof); and a CDR-L1 that comprises the amino acid sequence: QSVSSSY (SEQ ID NO: 18; or a variant thereof); a CDR-L2 that comprises the amino acid sequence: GAS (or a variant thereof); and a CDR-L3 that comprises the amino acid sequence: QQYGSSPWT (SEQ ID NO: 22; or a variant thereof); and a CD28 binding arm that comprises: a CDR-H1 that comprises the amino acid sequence: GGSISSYY (SEQ ID NO: 12; or a variant thereof); a CDR-H2 that comprises the amino acid sequence: IYYSGIT (SEQ ID NO: 6; or a variant thereof); and a CDR-H3 that comprises the amino acid sequence: ARWGVRRDYYYYGMDV (SEQ ID NO: 14; or a variant thereof); and a CDR-L1 that comprises the amino acid sequence: QSVSSSY (SEQ ID NO: 18; or a variant thereof); a CDR-L2 that comprises the amino acid sequence: GAS (or a variant thereof); and a CDR-L3 that comprises the amino acid sequence: QQYGSSPWT (SEQ ID NO: 22; or a variant thereof).

In an embodiment of the invention, the multispecific (e.g., bi-specific) antigen-binding protein (e.g., antibody or antigen-binding fragment thereof) that binds EGFR and CD28 includes:

(1)
an EGFR binding arm that comprises: a heavy chain variable region that comprises the amino acid sequence set forth in SEQ ID NO: 2 (or a variant thereof); and a light chain variable region that comprises the amino acid sequence set forth in SEQ ID NO: 16 (or a variant thereof); and a CD28 binding arm that comprises: a heavy chain variable region that comprises the amino acid sequence set forth in SEQ ID NO: 10 (or a variant thereof); and a light chain variable region that comprises the amino acid sequence set forth in SEQ ID NO: 16 (or a variant thereof);

(2)
an EGFR binding arm that comprises: a heavy chain variable region that comprises the amino acid sequence set forth in SEQ ID NO: 30 (or a variant thereof); and a light chain variable region that comprises the amino acid sequence set forth in SEQ ID NO: 16 (or a variant thereof); and a CD28 binding arm that comprises: a heavy chain variable region that comprises the amino acid sequence set forth in SEQ ID NO: 10 (or a variant thereof); and a light chain variable region that comprises the amino acid sequence set forth in SEQ ID NO: 16 (or a variant thereof);

(3)
an EGFR binding arm that comprises: a heavy chain variable region that comprises the amino acid sequence set forth in SEQ ID NO: 40 (or a variant thereof); and a light chain variable region that comprises the amino acid sequence set forth in SEQ ID NO: 16 (or a variant thereof); and a CD28 binding arm that comprises: a heavy chain variable region that comprises the amino acid sequence set forth in SEQ ID NO: 10 (or a variant thereof); and a light chain variable region that comprises the amino acid sequence set forth in SEQ ID NO: 16 (or a variant thereof);

(4)
an EGFR binding arm that comprises: a heavy chain variable region that comprises the amino acid sequence set forth in SEQ ID NO: 50 (or a variant thereof); and a light chain variable region that comprises the amino acid sequence set forth in SEQ ID NO: 16 (or a variant thereof); and a CD28 binding arm that comprises: a heavy chain variable region that comprises the amino acid sequence set forth in SEQ ID NO: 10 (or a variant thereof); and a light chain variable region that comprises the amino acid sequence set forth in SEQ ID NO: 16 (or a variant thereof).

In an embodiment of the invention, the multispecific (e.g., bi-specific) antigen-binding protein (e.g., antibody or antigen-binding fragment thereof) that binds EGFR and CD28 includes:

(1)
an EGFR binding arm that comprises: a heavy chain that comprises the amino acid sequence set forth in SEQ ID NO: 24 (or a variant thereof); and a light chain that comprises the amino acid sequence set forth in SEQ ID NO: 28 (or a variant thereof); and a CD28 binding arm that comprises: a heavy chain that comprises the amino acid sequence set forth in SEQ ID NO: 26 (or a variant thereof); and a light chain that comprises the amino acid sequence set forth in SEQ ID NO: 28 (or a variant thereof);

(2)
an EGFR binding arm that comprises: a heavy chain that comprises the amino acid sequence set forth in SEQ ID NO: 38 (or a variant thereof); and a light chain that comprises the amino acid sequence set forth in SEQ ID NO: 28 (or a variant thereof); and a CD28 binding arm that comprises: a heavy chain that comprises the amino acid sequence set forth in SEQ ID NO: 26 (or a variant thereof); and a light chain that comprises the amino acid sequence set forth in SEQ ID NO: 28 (or a variant thereof);

(3)
  an EGFR binding arm that comprises: a heavy chain that comprises the amino acid sequence set forth in SEQ ID NO: 48 (or a variant thereof); and a light chain that comprises the amino acid sequence set forth in SEQ ID NO: 28 (or a variant thereof);
  and
  a CD28 binding arm that comprises: a heavy chain that comprises the amino acid sequence set forth in SEQ ID NO: 26 (or a variant thereof); and a light chain that comprises the amino acid sequence set forth in SEQ ID NO: 28 (or a variant thereof);
(4)
  an EGFR binding arm that comprises: a heavy chain that comprises the amino acid sequence set forth in SEQ ID NO: 58 (or a variant thereof); and a light chain that comprises the amino acid sequence set forth in SEQ ID NO: 28 (or a variant thereof);
  and
  a CD28 binding arm that comprises: a heavy chain that comprises the amino acid sequence set forth in SEQ ID NO: 26 (or a variant thereof); and a light chain that comprises the amino acid sequence set forth in SEQ ID NO: 28 (or a variant thereof).

In an embodiment of the invention, the multispecific (e.g., bispecific) antigen-binding protein (e.g., an antibody or antigen-binding fragment thereof) is REGN7075 (also referred to herein as bsAb7075); REGN6321 (also referred to herein as bsAb6321); REGN6322 (also referred to herein as bsAb6322); REGN6323 (also referred to herein as bsAb6323). Other bispecific antibodies may be generated using the parental EGFR antibodies described herein in Tables 9A, 9B and 9C, whereby the sequences of the HCVR arms of the EGFR parental antibodies may be found in WO2014/004427 and the HCVR amino acid sequences of the parental CD28 antibodies may be found in Table 3 herein. Any EGFR HCVR arm may be paired with any of the CD28 HCVR arms described herein.

The present invention also provides an antigen-binding protein (e.g., antibody or antigen-binding fragment thereof) that specifically binds to epidermal growth factor receptor comprising: (i) a heavy chain immunoglobulin or variable region thereof that comprises HCDR1, HCDR2 and HCDR3 of a heavy chain immunoglobulin or variable region thereof that comprises the amino acid sequence set forth in SEQ ID NO: 2, 24, 30, 38, 40, 48, 50 or 58; or a variant thereof; and/or (ii) a light chain immunoglobulin or variable region thereof that comprises LCDR1, LCDR2 and LCDR3 of a light chain immunoglobulin or variable region thereof that comprises the amino acid sequence set forth in SEQ ID NO: 16 or 28; or a variant thereof. In an embodiment of the invention, the antigen-binding protein is multispecific (e.g., bispecific).

The present invention also provides a multispecific antigen-binding protein set forth herein bound to an EGFR polypeptide or an antigenic fragment thereof (e.g., on the surface of a tumor cell) and a CD28 polypeptide or an antigenic fragment thereof (e.g., on the surface of an immune cells such as a T-cell).

The present invention also provides a method for making a multispecific (e.g., bi-specific) antigen-binding protein set forth herein comprising: (a) introducing one or more polynucleotides encoding the immunoglobulin chains of said antigen-binding protein into a host cell (e.g., a CHO cell); (b) culturing the host cell under conditions favorable to expression of the polynucleotide; and (c) optionally, isolating the antigen-binding protein or immunoglobulin chain from the host cell and/or medium in which the host cell is grown. Any antigen-binding protein or immunoglobulin chain which is a product of such a method is part of the present invention.

The present invention also provides a polynucleotide encoding one or more of the immunoglobulin chains of a multispecific (e.g., bi-specific) antigen-binding protein of the present invention. Vectors comprising the polynucleotides of the present invention are also part of the present invention as well as host cells (e.g., CHO) comprising a polynucleotide, vector or antigen-binding protein of the present invention.

The present invention also provides a composition or kit comprising one or more of the multispecific antigen-binding proteins of the present invention in association with one or more other substances or items, optionally, in association with a further therapeutic agent (e.g., PD-1 inhibitor, an anti-PD-1 antibody or antigen-binding fragment thereof, a PD-L1 inhibitor, an anti-PD-L1 antibody or antigen-binding fragment thereof, a platinum anti-cancer chemotherapeutic agent, paclitaxel, docetaxel, vincristine, cisplatin, carboplatin, oxaliplatin, an anti-cancer antibody or antigen-binding fragment thereof, pembrolizumab, nivolumab, trastuzumab, cetuximab, bevacizumab and/or cemiplimab). Pharmaceutical formulations comprising the multispecific antigen-binding protein of the present invention and a pharmaceutically acceptable carrier or excipient and, optionally, a further therapeutic agent are also part of the present invention.

The present invention also provides vessels and injection devices (e.g., syringe, pre-filled syringe or autoinjector) including the multispecific antigen-binding proteins, compositions and/or formulations of the present invention.

The present invention also provides a method for administering a multispecific antigen-binding protein of the present invention, composition or formulation thereof to a subject (e.g. a human) comprising injecting said antigen-binding protein, composition or formulation into the body of the subject, e.g., with a syringe, pre-filled syringe or auto-injector. Optionally a further therapeutic agent (e.g., cemiplimab, pembrolizumab or nivolumab) is also administered to the subject.

The present invention also provides a method for treating or preventing a hyperproliferative disease (e.g., EGFR-expressing cancer), in a subject (e.g., a human) in need thereof, comprising administering (e.g., subcutaneously, intravenously or intramuscularly) an effective amount of multispecific antigen-binding protein or composition or formulation, optionally in association with a further therapeutic agent (e.g., cemiplimab, pembrolizumab or nivolumab). In an embodiment of the invention, the EGFR-expressing cancer is esophageal carcinoma, lung squamous cell carcinoma, lung adenocarcinoma, cervical squamous cell carcinoma, endometrial adenocarcinoma, bladder urothelial carcinoma, lung cancer, non-small cell lung cancer, colorectal cancer, rectal cancer, endometrial cancer, skin cancer, head & neck squamous cell carcinoma, brain cancer, glioblastoma multiforme, breast cancer, gastroesophageal cancer, gastroesophageal adenocarcinoma, prostate cancer or ovarian cancer.

BRIEF DESCRIPTION OF THE DRAWINGS

In FIGS. 1A and 1B, flow cytometry analysis shows that EGFR×CD28 bispecific antibody binds to CD28+ and EGFR+ cells. (FIG. 1A) Jurkat cells (CD28+ cells). (FIG. 1B) PEO1 cells (EGFR+ cells). In FIGS. 1C-1E, human T-cells were cultured with cancer target cells expressing endogenous MUC16 and EGFR (Ovarian cancer cell line PEO1) and the indicated bispecifics for 96 hours. (FIG. 1C) Tumor cell kill, % viable cells. (FIG. 1D) frequency of $CD25^+$ T cells (% of CD2). (FIG. 1E) Supernatants from cytotoxicity assay were analyzed using a Cytometric Bead Array (CBA) kit. IFNγ released is plotted as pg/ml FIGS. 2A, 2B, 2C, and 2D show that expression of a CD28 ligand (CD86) on tumor cells synergizes with anti-PD1 treatment to induce CD8 dependent anti-tumor immunity. MC38 tumor cells were transduced with the ligand for CD28, CD86 (MC38/CD86), or empty vector control (MC38/EV). WT C57BL6 mice were initially implanted with $1\times10^6$ tumor cells per mouse and treated with PD-1 mAb or rigG2a isotype control at 5 mg/kg on day 0, 3, 7, 10 and 14 post tumor implant. FIG. 2A. Average tumor volume over time. Error bars represent+/−SEM. Statistical significance was determined with two-way ANOVA and Tukey's multiple comparisons tests. FIG. 2B. Survival over time (percentage of mice with tumors<2000 $mm^3$). Statistical significance at day 60 post-implantation was determined with the Log-rank (Mantel-Cox) test. FIG. 2C. Mice were treated CD8 depleting antibody (CD8 depleted) or isotype control (no depletion). Average tumor volume over time with CD8 depletion (dotted lines) and no depletion (solid lines) is shown+/−SEM. Statistical significance was determined with two-way ANOVA and Tukey's multiple comparisons tests. FIG. 2D. Secondary tumor implant (re-challenge) of tumor free mice that were implanted with MC38/CD86 and treated with PD1 mAb. For FIGS. 2A to 2D, data are shown from 1 experiment with 10 mice per group. Data are representative of at least 4 separate experiments. Statistical significance is indicated (*p<0.05, p<0.01, *p<0.001, and ****p<0.0001).

FIG. 3A shows human CD45+ cell engraftment in peripheral blood, pre-treatment. FIG. 3B shows A431 FACS analysis. Marker of interest is indicated for each plot.

FIG. 4 specifically shows average A431 tumor volumes for each treatment group ($mm^3$±SEM) (isotype, anti-PD1 monotherapy (cemiplimab), EGFR×CD28 (REGN7075) monotherapy or EGFR×CD28 (REGN7075)+anti-PD1 combination therapy) plotted against days after tumor in VH mice engrafted with human CD34+ cells. Two-way ANONA, Tukey comparison:  P<0.01, ** P<0.0001.

FIG. 5 shows average A431 tumor volumes for control group ($mm^3$±SEM) (isotype, anti-PD1 monotherapy (cemiplimab), PSMA×CD28 monotherapy or PSMA×CD28+anti-PD1 combination therapy) plotted against days after tumor in VH mice engrafted with human CD34+ cells. Two-way ANONA, Tukey comparison:  P<0.01, ** P<0.0001.

(FIG. 9A) MFI of selected tumor CD8+ T-cell clusters identified by CITRUS (cluster identification, characterization, and regression) analysis; (FIG. 9B) Frequency of cells in each cluster from the indicated treatment groups; (FIG. 9C) MFI of selected tumor CD4+ T-cell clusters identified by CITRUS analysis; (FIG. 9D) Frequency of cells in each cluster from the indicated treatment groups. FIGS. 9B and 9D demonstrate that EGFR×CD28 synergizes with anti-PD1 treatment to induce anti-tumor immunity in VH mice engrafted with human fetal liver CD34+ cells.

FIGS. 10A, 10B, and 10C. EGFR×CD28 (REGN7075) alone or in combination with anti-PD1 (cemiplimab) therapy does not induce systemic T-cell activation in comparison to CD28 superagonist in cynomolgus monkeys. Cynomolgus monkeys were treated with a single dose of bi-specific antibodies at the indicated dose (mg/kg). Time is indicated post-dose (hr) (FIG. 10A) Serum cytokines (IFNgamma, IL-2, IL-6, IL-8 and IL-10) (FIG. 10B) Relative peripheral blood T-cell counts (FIG. 10C) Frequency of Ki67+ and ICOS+ T-cells (% of CD3). Values represent the average+/−SEM. N=3 animals per group. P values were calculated with 2way ANOVA with comparison to isotype control. (, p<0.01; *, p<0.001 and ****, p<0.0001).

Figure 13A:
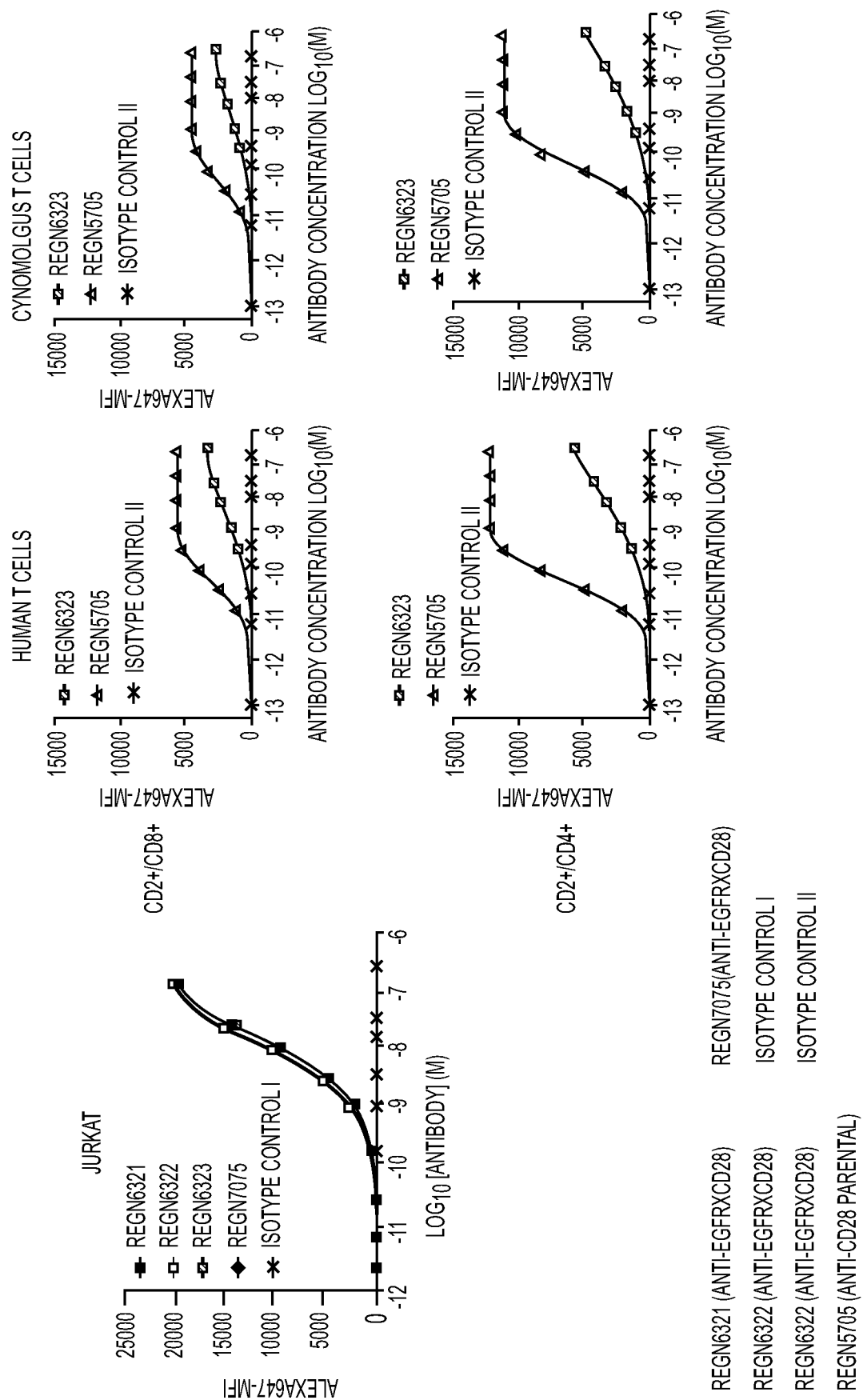
FIGS. 13A, 13B, and 13C describe the binding of various anti-EGFR×anti-CD28 antibodies to various cells, including human and cynomolgus T cells and Jurkat cells (CD28+ effector cells)(FIG. 13A); various other tumor target cells including A375 melanoma cells, 22RV1 prostate cells, PEO1 ovarian cells, CAPAN pancreatic cells, SW1990
Figure 13B:
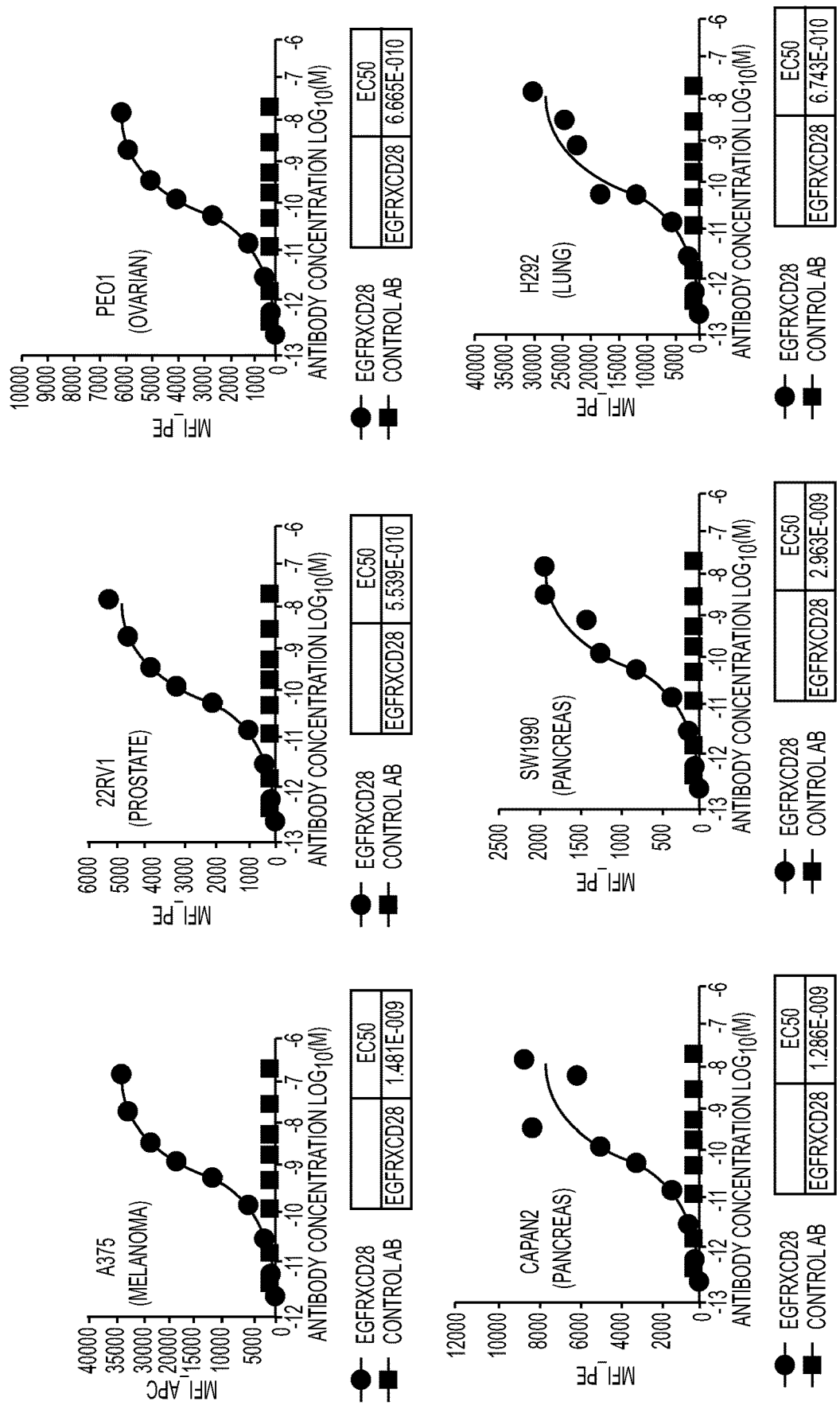
Figure 13C:
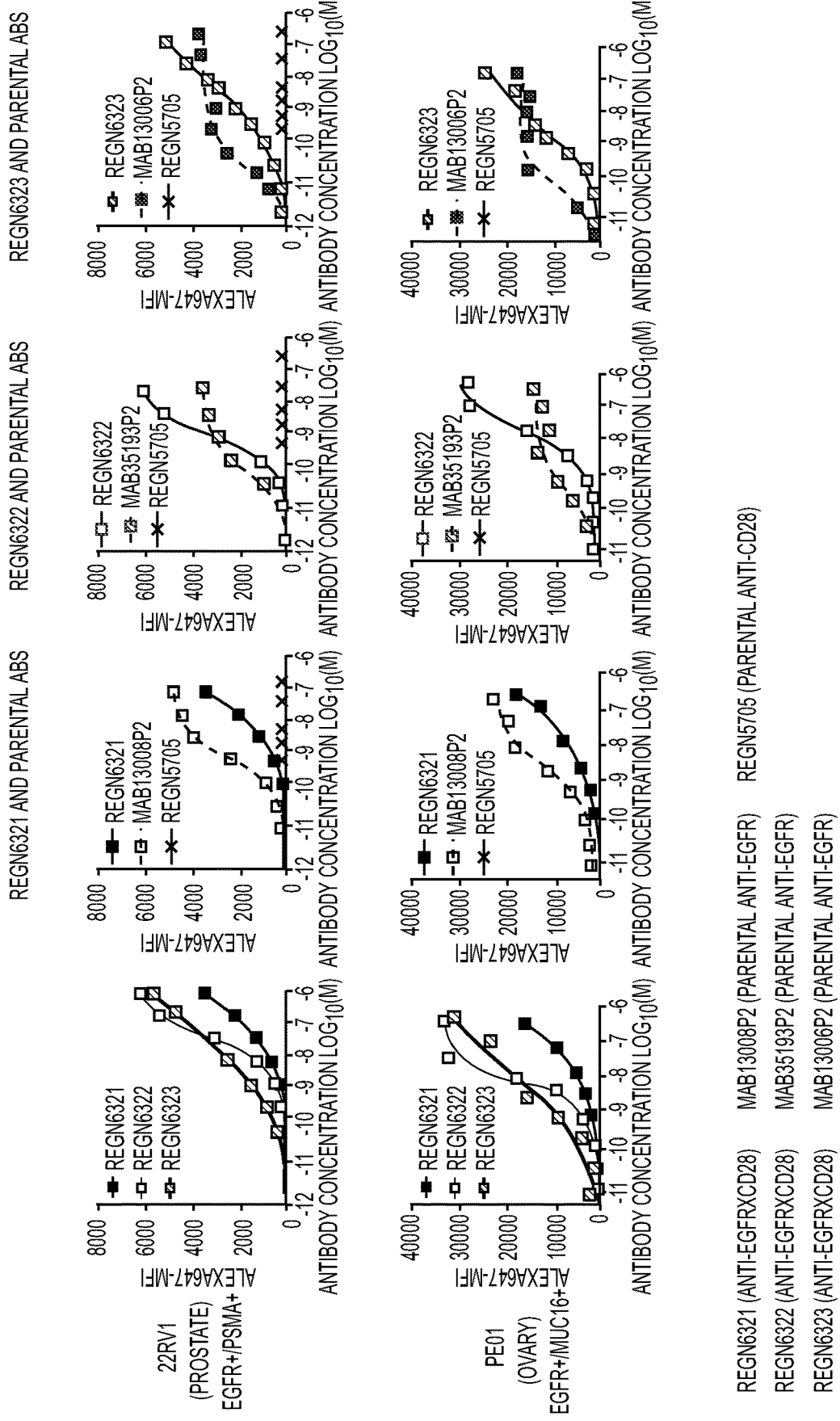

Pancreatic cells and H292 lung cells (FIGS. 13B and 13C). Isotype Control I and II are antibodies that bind to Mers and EGFRvIII, respectively.

Figure 14A:
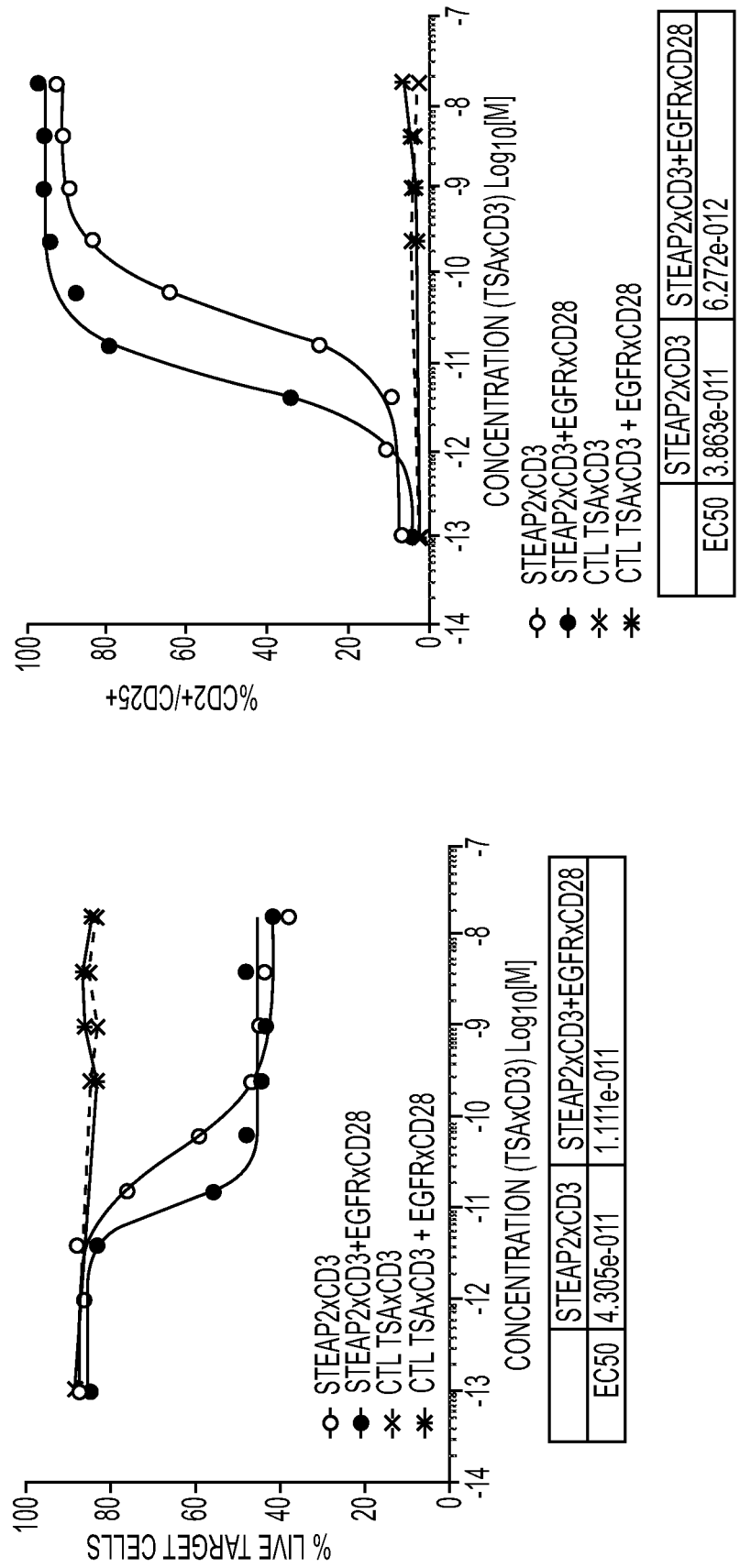
Figure 14B:
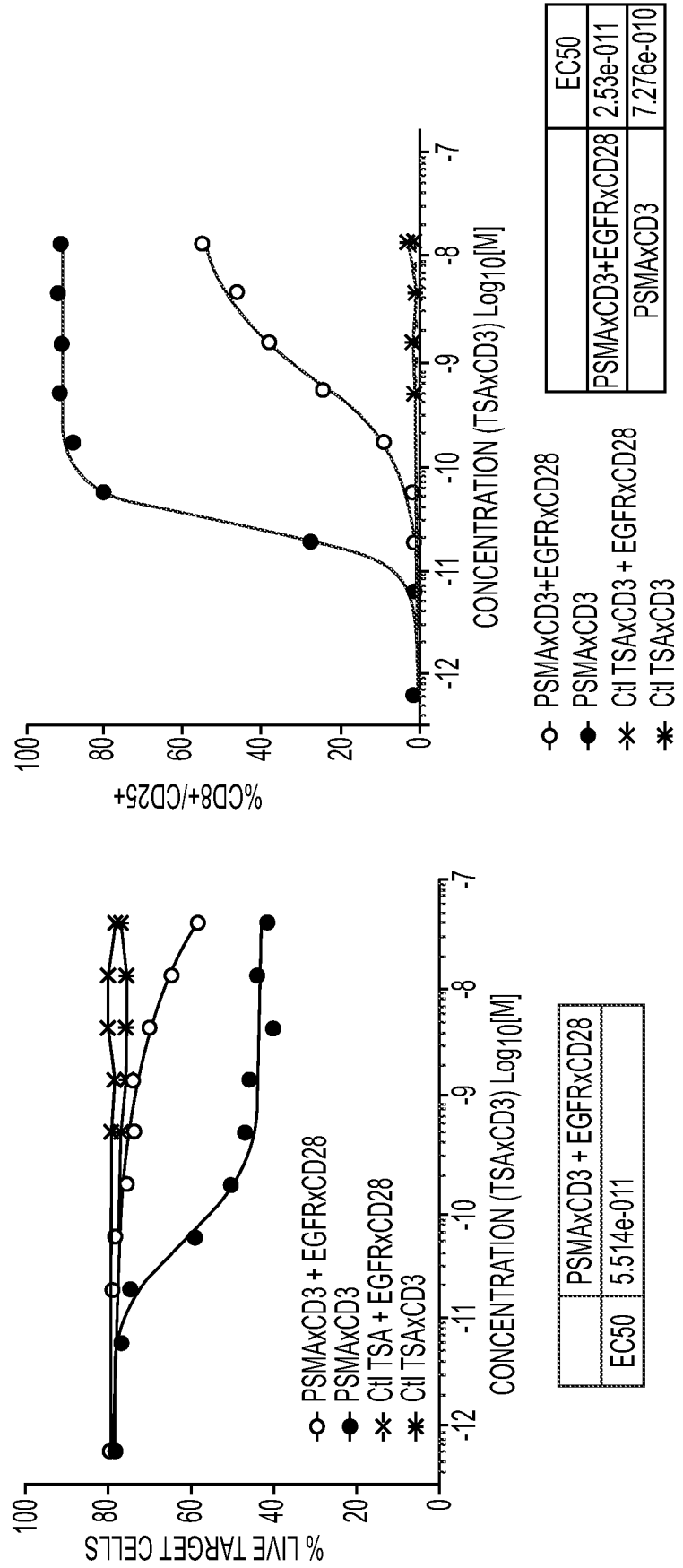

FIGS. 14A and 14B show that an anti-EGFR×anti-CD28 bispecific antibody enhances the cytotoxic potency of an anti-tumor specific antigen (TSA)×anti-CD3 bispecific antibody. The study included an anti-EGFR× anti-CD28 antibody combined with either an anti-STEAP2× anti-CD3 bispecific antibody (FIG. 14A) or an anti-PSMA× anti-CD3 bispecific antibody (FIG. 14B). The anti-STEAP2×anti-CD3 antibody was described in WO2018/058001A. The anti-PSMA×anti-CD3 antibody was described in WO2017/053856A1.

Figure 15A:
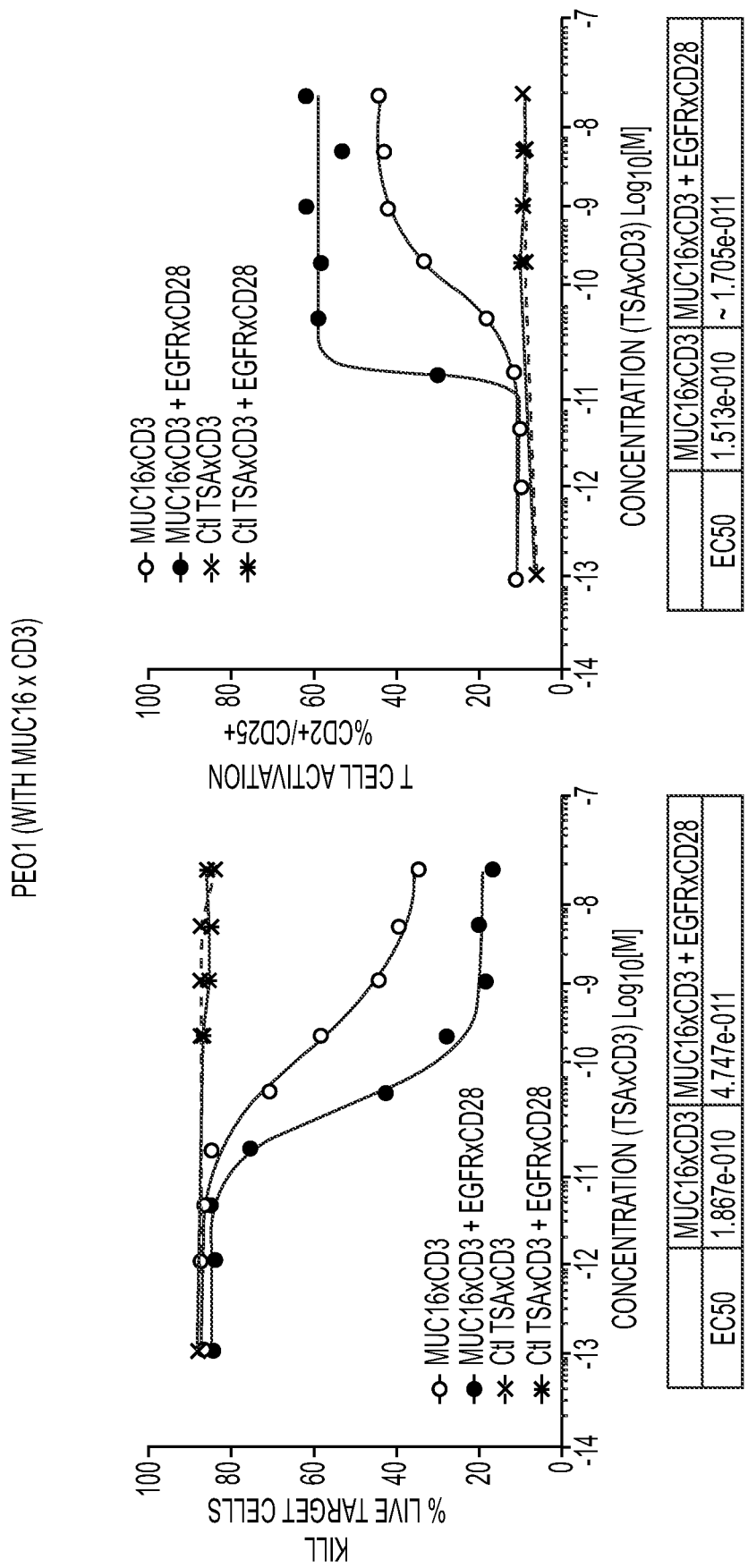
Figure 15B:
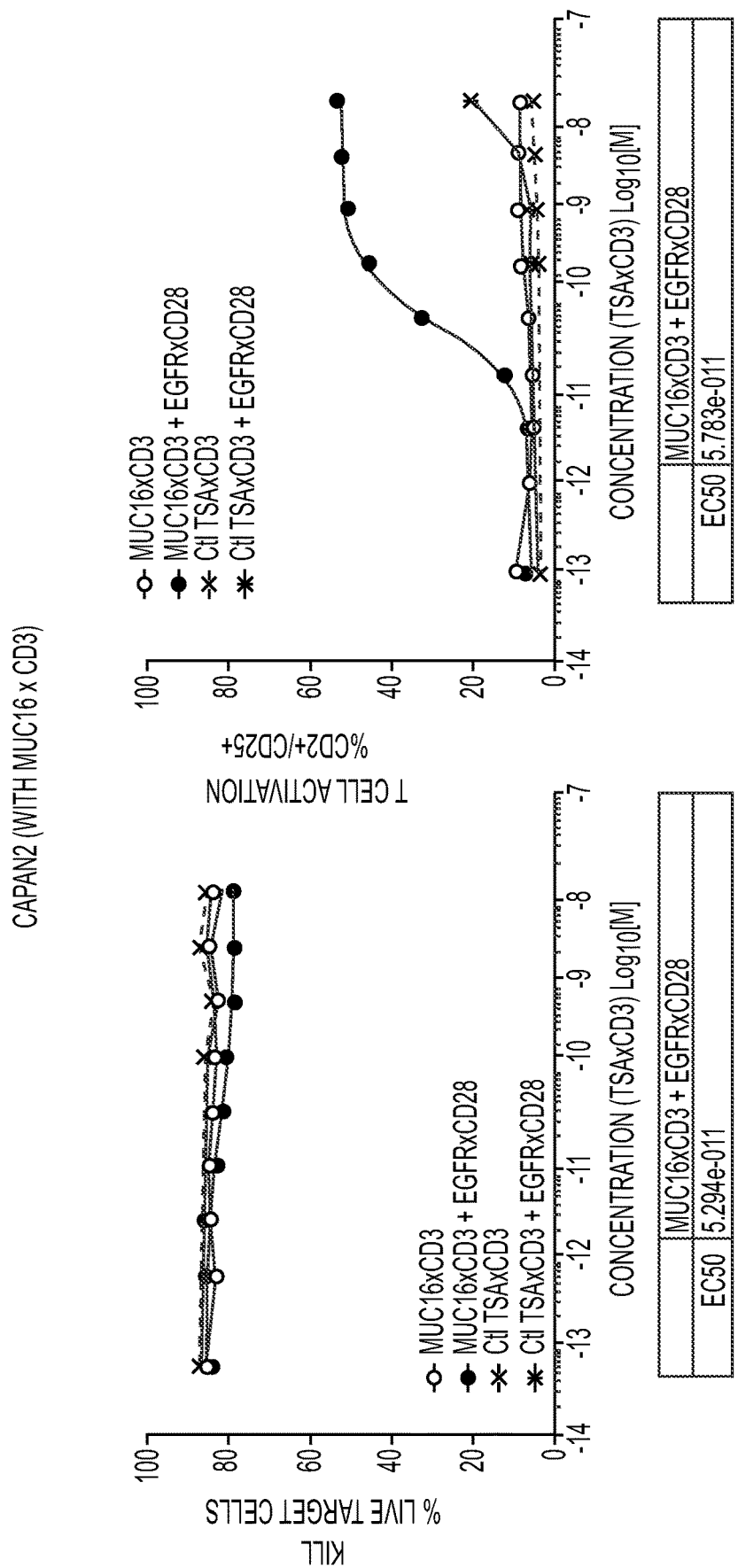
Figure 15C:
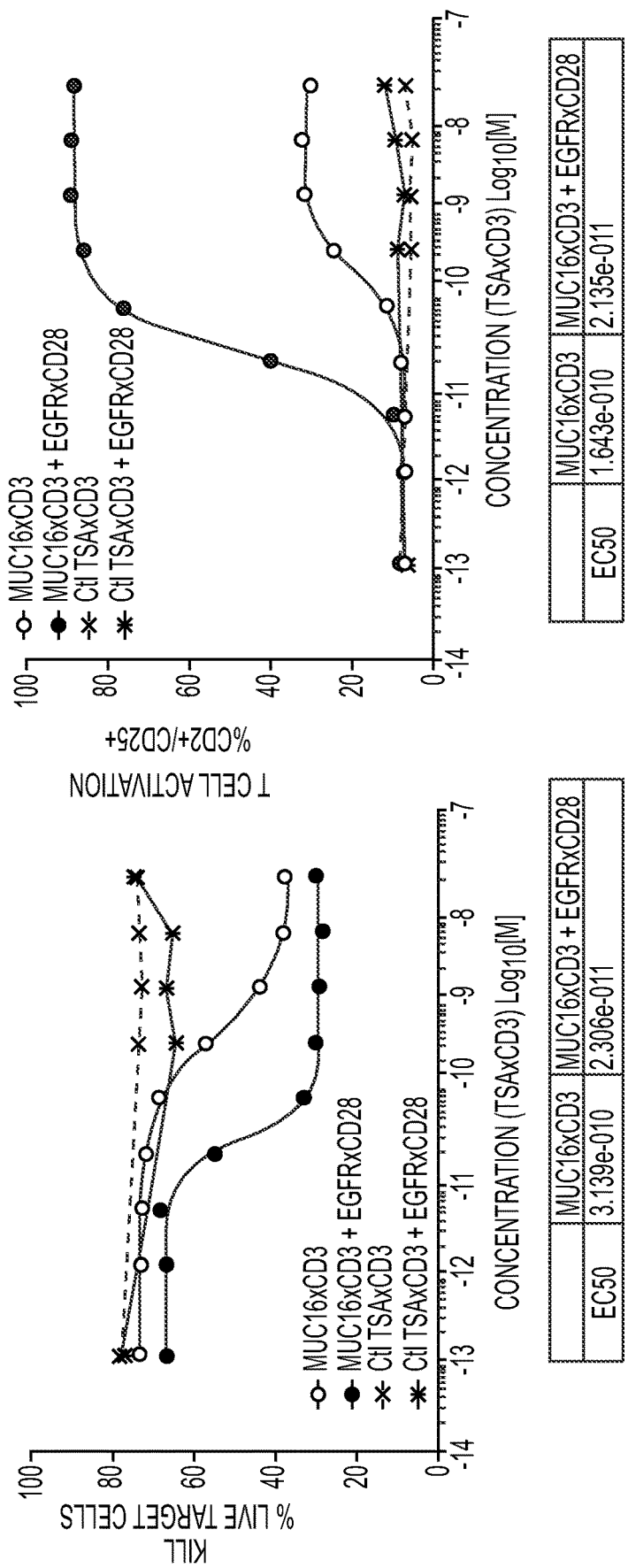
Figure 15D:
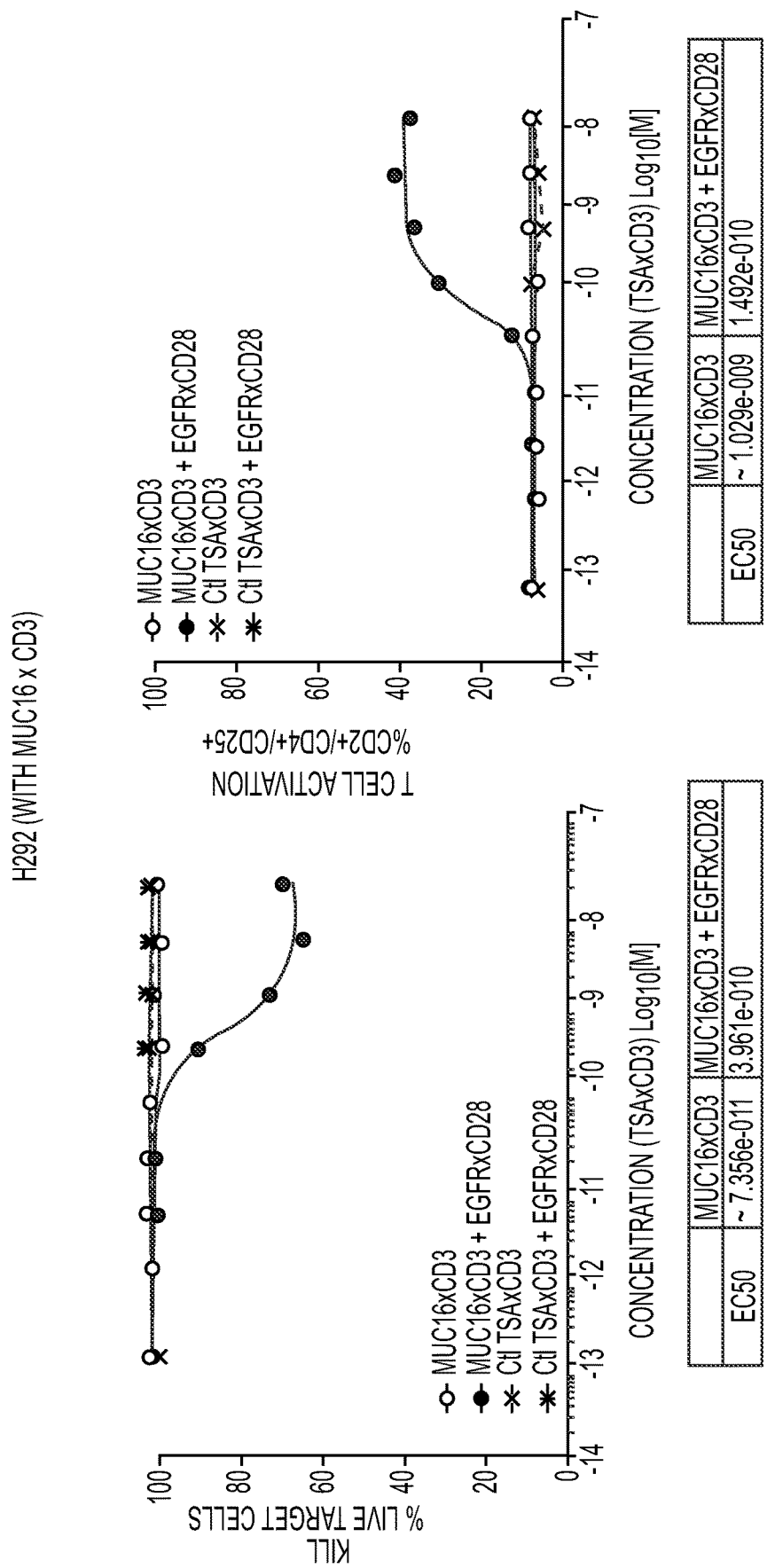

FIGS. 15A, 15B, 15C and 15D show that an anti-EGFR× anti-CD28 bispecific antibody enhances the cytotoxic potency of an anti-tumor specific antigen (TSA)×anti-CD3 bispecific antibody (anti-MUC16×anti-CD3) across various cell lines, including PEO1 cells (FIG. 15A), CAPAN2 cells (FIG. 15B), SW1990 cells (FIG. 15C) and H292 cells (FIG. 15D).

DETAILED DESCRIPTION OF THE INVENTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Checkpoint inhibition with PD-1 blocking mAb are known to release the break on T cell activation, but their efficacy as a single agent often not always sufficient to get tumor clearance and a durable anti-tumor response in many cancers. Several approaches to improve the response rate to PD-1 inhibition are currently being evaluated. Indeed, identification of biomarkers to predict responsiveness to PD-1 mAbs, non-tumor targeted combination therapies using PD-1 inhibition together with agonistic antibodies triggering costimulatory receptors to improve T cell activation, or with chemotherapy or radiotherapy are all currently undergoing pre-clinical and clinical testing. The challenge however is that many of these combinations are often based on the availability of pre-existing drug and a post-hoc rationale to combine therapies, rather than a truly hypothesis-driven approach, which in some cases has led to worse outcomes for the patient. It is evident that checkpoint inhibition and reactivation of the immune system offers the potential of long term remission in a number of patients, therefore methods to further improve or enhance T cell activity to promote a more durable responses are warranted. Here, to improve the anti-tumor efficacy of PD-1 mAb, the concept of using an EGFR×CD28 bispecific to enhance T-cell signaling and activation was introduced. Indeed, this novel combination immunotherapy demonstrated that CD28 costimulatory bispecific antibodies synergize with PD-1 mAb to not only generate robust T-cell activation but also to provide durable anti-tumor responses without systemic toxicity. Consequently, this tumor-targeted combination therapy provides a considerable advantage over the non-targeted approaches described previously. Using CD28-bispecific antibodies, which do not directly activate CD28 unless clustered on tumor cell surfaces, offered the possibility of promoting co-stimulation only at the tumor site, avoiding the systemic toxicity of conventional CD28-activating antibodies, the toxicity often observed with the combination of CLTA-4 and PD-1 blockade or other costimulatory agonist bivalent antibodies. Toxicology studies in genetically-humanized immunocompetent mice, as well as in cynomolgus monkeys, showed that these bispecifics exhibited no toxicity as single agents or in combination with PD-1 mAb. The safety profile together with the similar enhancement of anti-tumor efficacy by EGFR×CD28 with anti-PD-1 mAb across syngeneic and xenogeneic models suggested that this therapeutic modality is robust, not limited to a specific tumor model, and could have broader utility as a novel combination class for immunotherapy.

To enhance T-cell-mediated killing of tumor cells, tumor-targeted approaches are being developed. Indeed, CD3-based bispecific antibodies represent an emerging class of antibodies that can efficiently trigger T-cell activation, by linking a T cell to a tumor cell and activating TCR/CD3, thus mimicking normal "signal 1". However, despite their promising clinical efficacy, CD3-bispecifics can be associated with cytokine release syndrome (CRS) due to direct T-cell activation and lack of tumor only specificity. Further, TCR/CD3 activation in the absence of co-stimulation ("signal 2") can lead to anergy or activation induced cell death (AICD), which may limit or reduce the potential anti-tumor effects of these reagents. Here it was demonstrated for the first time that EGFR×CD28 bispecific and anti-PD-1 mAb combination therapy induced a tumor specific T-cell activation. As shown herein, EGFR×CD28 bispecific antibodies have limited or no activity in the absence of "signal 1" and PD-1 blockade relies on the endogenous antigen specific T-cell response to tumor peptides. Thus, CD28-bispecifics together with PD-1 blockade can boost endogenous TCR/CD3-dependent T cell responses driving durable anti-tumor responses.

The anti-tumor activity of PD-1 mAb is CD28-dependent and the PD-1 inhibition of T-cell activation reduces signaling through TCR/CD3 and/or CD28 which may be affecting the spatial localization of those molecules. The data herein demonstrated that PD-1 is accumulated at the immune synapse when PD-L1 is expressed by target cells and its accumulation is associated with a reduction of CD28 at the synapse, suggesting that PD-1 could exercise T-cell inhibition, by preventing CD28 localization to the synapse. In addition, it was found that PD-1 blockade prevented PD-1 synaptic localization while CD28 accumulation at the synapse was increased, allowing EGFR×CD28 bispecifics to markedly enhance the ability of PD-1 mAb to promote T-cell activation. This may be one of the mechanisms by which PD-1 blocking antibody promotes T-cell activation. Overall, the visualization of PD-1 and CD28 localization in the immunological synapse following PD-1-PD-L1 interaction and/or PD-1 inhibition, made it possible to better understand the effect of PD-1 blockade on T-cell activation, as well as the synergy between EGFR×CD28 and PD-1 mAb at the level of the immune synapse.

Although PD-1 mAbs are an important new class of immunotherapy, further optimization of anti-tumor activity will surely be necessary in many cases. Just as CAR-T approaches have employed chimeric receptors that artificially activate both "signal 1" and "signal 2" so as to improve their anti-tumor activity, it is now shown the potential benefit of combining PD-1 inhibition with CD28-bispecifics (which provide "signal 2") to enhance anti-tumor activity. This approach has several practical benefits over CAR-T therapies in that it does not require a laborious cell therapy preparation that must be individually customized for each patient, nor does it require that patients be pre-emptively "lymphodepleted" via toxic chemotherapy that is often associated with adverse effects so that they can't accept cell therapy. This bispecific approach offers the potential for increased efficacy as well as increased safety through its specificity of action. Collectively, the data here suggest that combining CD28-based bispecifics with the clinically validated PD-1 mAb, such as cemiplimab, may provide well-tolerated, biologics solutions with markedly enhanced and synergistic anti-tumor activity.

Definitions

"EGFR" and "EGFR fragment," as used herein refer to the well-known human EGFR protein or a fragment thereof unless specified as being from a non-human species (e.g., "mouse EGFR," "mouse EGFR fragment," "monkey EGFR," "monkey EGFR fragment," etc.). In an embodiment of the invention, human EGFR comprises the amino acid sequence set forth in NCBI accession no. NP_005219.2. In one embodiment, human EGFR (amino acids L25-A647 of Accession number 005228.4) is shown with a C-terminal CPGG.myc epitope (E1-L10).GlyGly.myc epitope (E1-L10).SerGly.6×His.SSG tag (SEQ ID NO: 69).

"CD28," as used herein, refers to the well-known human CD28 protein which is express on T cells as a costimulatory receptor unless specified as being from a non-human species. In an embodiment of the invention, human CD28 comprises the amino acid sequence as set forth NCBI accession No. NP_006130.1.

"Isolated" antigen-binding proteins (e.g., antibodies or antigen-binding fragments thereof), polypeptides, polynucleotides and vectors, are at least partially free of other biological molecules from the cells or cell culture from which they are produced. Such biological molecules include nucleic acids, proteins, other antibodies or antigen-binding fragments, lipids, carbohydrates, or other material such as cellular debris and growth medium. An isolated antigen-binding protein may further be at least partially free of expression system components such as biological molecules from a host cell or of the growth medium thereof. Generally, the term "isolated" is not intended to refer to a complete absence of such biological molecules or to an absence of water, buffers, or salts or to components of a pharmaceutical formulation that includes the antigen-binding proteins (e.g., antibodies or antigen-binding fragments).

The following references relate to BLAST algorithms often used for sequence analysis: BLAST ALGORITHMS: Altschul et al. (2005) FEBS J. 272(20): 5101-5109; Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, N.Y.

The present invention includes a polypeptide comprising the amino acid sequence set forth in SEQ ID NO: 6; 8; 10; 12; 14; 24; 34; 36; 38; 44; 46; 48; 54; 56 and/or 58.

An "antibody" is an immunoglobulin molecule comprising four polypeptide chains, two heavy chains (HC) and two light chains (LC) inter-connected by disulfide bonds. Each heavy chain (HC) comprises a heavy chain variable region (abbreviated herein as HCVR or $V_H$) and a heavy chain constant region (e.g., IgG, IgG1 or IgG4). The heavy chain constant region comprises three domains, $C_H1$, $C_H2$ and $C_H3$. Each light chain (LC) comprises a light chain variable region (abbreviated herein as LCVR or $V_L$) and a light chain constant region (e.g., lambda or kappa). The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ includes three CDRs and four FRs, arranged from amino-terminus to carboxy-terminus in the following order: FR1, CDR1, FR2, CDR2, FR3, CDR3, FR4. A heavy chain CDR may be referred to as HCDR and a light chain CDR may be referred to as LCDR. In different embodiments of the invention, the FRs of an antibody (or antigen-binding portion thereof) may be identical to the human germline sequences, or may be naturally or artificially modified.

An antigen-binding arm of a Y-shaped IgG antibody (e.g., a CD28 or EGFR binding arm) refers to a structural portion of the antibody that confers binding specificity to the antigen. For example, an antigen-binding arm of an IgG antibody has a heavy chain (HC) associated with a light chain (LC).

An antibody which, for example, is bispecific includes an arm that binds to a first antigen and another arm that binds to a second antigen. For example, an EGFR×CD28 bispecific antibody includes one arm that binds EGFR and another arm that binds to CD28.

Bispecific antigen-binding molecules (e.g., bispecific antibodies) may have an effector arm that binds to a first antigen and a targeting arm that binds to second antigen. The effector arm may be the first antigen-binding domain (e.g., anti-CD28) that binds to the antigens on effector cells (e.g., T cells). The targeting arm may be the second antigen binding domain (e.g., anti-EGFR antibody) that binds to the antigens on target cells (e.g., tumor cells). According to certain exemplary embodiments, the effector arm binds to CD28 and the targeting arm binds to EGFR.

An "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. A multispecific antigen-binding fragment of an antibody binds to multiple antigens (e.g., two different antigens if the fragment is bispecific). Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Non-limiting examples of antigen-binding fragments include: (i) Fab fragments; (ii) F(ab')$_2$ fragments; (iii) Fd fragments; (iv) Fv fragments; (v) single-chain Fv (scFv) molecules; and (vi) dAb fragments.

An antigen-binding fragment of an antibody will, in an embodiment of the invention, comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

The term "recombinant" antigen-binding proteins, such as antibodies or antigen-binding fragments thereof, refers to such molecules created, expressed, isolated or obtained by technologies or methods known in the art as recombinant DNA technology which include, e.g., DNA splicing and transgenic expression. The term includes antibodies expressed in a non-human mammal (including transgenic non-human mammals, e.g., transgenic mice), or a host cell (e.g., Chinese hamster ovary (CHO) cell) or cellular expression system or isolated from a recombinant combinatorial human antibody library. The present invention includes recombinant antigen-binding proteins as set forth herein.

The term "specifically binds" or "binds specifically" refers to those antigen-binding proteins (e.g., antibodies or antigen-binding fragments thereof) having a binding affinity to an antigen, such as EGFR or CD28 protein, expressed as $K_D$, of less than about $10^{-6}$ M (e.g., $10^{-7}$ M, $10^{-8}$ M, $10^{-9}$ M, $10^{-10}$ M, $10^{-11}$ M or $10^{-12}$ M), as measured by real-time, label free bio-layer interferometry assay, for example, at 25° C. or 37° C., e.g., an Octet® HTX biosensor, or by surface plasmon resonance, e.g., BIACORE™, or by solution-affinity ELISA. "Anti-EGFR" refers to an antigen-binding protein (or other molecule such as an antigen-binding arm), for example an antibody or antigen-binding fragment thereof, that binds specifically to EGFR and "anti-CD28" refers to an antigen-binding protein (or other molecule such as an antigen-binding arm), for example an antibody or antigen-binding fragment thereof, that binds specifically to CD28. "EGFR×CD28" refers to refers to an antigen-binding protein (or other molecule), for example an antibody or antigen-binding fragment thereof, that binds specifically to EGFR and to CD28 (and, optionally, to one or more other antigens).

The present invention includes antigen-binding proteins, e.g., antibodies or antigen-binding fragments, that bind to the same EGFR and CD28 epitopes as an antigen-binding protein of the present invention (e.g. REGN7075 (also referred to herein as bsAb7075); REGN6321 (also referred to herein as bsAb6321); REGN6322 (also referred to herein as bsAb6322); REGN6323 (also referred to herein as bsAb6323). Other anti-EGFR× anti-CD28 antigen-binding proteins may be found in Tables 9A, 9B and 9C. The amino acid sequences of the EGFR HCVR arms of the bispecific antibodies described herein may be found in Table 1, whereas the amino acid sequences of the CD28 HCVR arms of the bispecific antibodies described herein may be found in Table 3. Other EGFR parental antibodies for use in the present invention are described in WO2014/004427. The amino acid sequences for the EGFR HCVR arm and the CD28 HCVR arm of REGN7075, REGN6321, REGN6322 and REGN6323 are found in Table 6. The amino acid sequences of the common light chain variable region described in the present invention are also found in Table 6.

The term "epitope" refers to an antigenic determinant (e.g., on EGFR or CD28) that interacts with a specific antigen-binding site of an antigen-binding protein, e.g., a variable region of an antibody molecule, known as a paratope. A single antigen may have more than one epitope. Thus, different antibodies may bind to different areas on an antigen and may have different biological effects. The term "epitope" may also refer to a site on an antigen to which B and/or T cells respond and/or to a region of an antigen that is bound by an antibody. Epitopes may be defined as structural or functional. Functional epitopes are generally a subset of the structural epitopes and have those residues that directly contribute to the affinity of the interaction. Epitopes may be linear or conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

Methods for determining the epitope of an antigen-binding protein, e.g., antibody or fragment or polypeptide, include alanine scanning mutational analysis, peptide blot analysis (Reineke (2004) Methods Mol. Biol. 248: 443-63), peptide cleavage analysis, crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antigen-binding protein (e.g., antibody or fragment or polypeptide) interacts is hydrogen/deuterium exchange detected by mass spectrometry. See, e.g., Ehring (1999) Analytical Biochemistry 267: 252-259; Engen and Smith (2001) Anal. Chem. 73: 256A-265A.

The present invention includes antigen-binding proteins that compete for binding to CD28 and EGFR with an antigen-binding protein of the present invention, e.g., (e.g. REGN7075 (also referred to herein as bsAb7075); REGN6321 (also referred to herein as bsAb6321); REGN6322 (also referred to herein as bsAb6322); REGN6323 (also referred to herein as bsAb6323), as well as those described in Tables 9A, 9B and 9C. The term "competes" as used herein, refers to an antigen-binding protein (e.g., antibody or antigen-binding fragment thereof) that binds to an antigen and inhibits or blocks the binding of another antigen-binding protein (e.g., antibody or antigen-binding fragment thereof) to the antigen. Unless otherwise stated, the term also includes competition between two antigen-binding proteins e.g., antibodies, in both orientations, i.e., a first antibody that binds antigen and blocks binding by a second antibody and vice versa. Thus, in an embodiment of the invention, competition occurs in one such orientation. In certain embodiments, the first antigen-binding protein (e.g., antibody) and second antigen-binding protein (e.g., antibody) may bind to the same epitope. Alternatively, the first and second antigen-binding proteins (e.g., antibodies) may bind to different, but, for example, overlapping or non-overlapping epitopes, wherein binding of one inhibits or blocks the binding of the second antibody, e.g., via steric hindrance. Competition between antigen-binding proteins (e.g., antibodies) may be measured by methods known in the art, for example, by a real-time, label-free bio-layer interferometry assay. Also, binding competition between antigen-binding proteins (e.g., monoclonal antibodies (mAbs)) can be determined using a real time, label-free bio-layer interferometry assay on an Octet RED384 biosensor (Pall ForteBio Corp.).

Typically, an antibody or antigen-binding fragment of the invention which is modified in some way retains the ability to specifically bind to EGFR and CD28, e.g., retains at least 10% of its EGFR and CD28 binding activity (when compared to the parental antibody) when that activity is expressed on a molar basis. Preferably, an antibody or antigen-binding fragment of the invention retains at least 20%, 50%, 70%, 80%, 90%, 95% or 100% or more of the EGFR and CD28 binding affinity as the parental antibody. It is also intended that an antibody or antigen-binding fragment of the invention may include conservative or non-conservative amino acid substitutions (referred to as "conservative variants" or "function conserved variants" of the antibody) that do not substantially alter its biologic activity.

A "variant" of a polypeptide, such as an immunoglobulin chain (e.g., REGN7075 (also referred to herein as bsAb7075); REGN6321 (also referred to herein as bsAb6321); REGN6322 (also referred to herein as bsAb6322); REGN6323 (also referred to herein as bsAb6323) $V_H$, $V_L$, HC or LC or CDR thereof comprising the amino acid sequence specifically set forth herein), refers to a polypeptide comprising an amino acid sequence that is at least about 70-99.9% (e.g., at least 70, 72, 74, 75, 76, 79, 80, 81, 82, 83, 84, 85, 86, 87, 88, 89, 90, 91, 92, 93, 94, 95, 96, 97, 98, 99, 99.5 or 99.9%) identical or similar to a referenced amino acid sequence that is set forth herein (e.g., any of the sequence GAS and SEQ ID NOs: 6; 8; 10; 12; 14; 16; 18; 22; 24; 26; 28; 30; 32; 34; 36; 38; 40; 42; 44; 46; 48; 50; 52; 54; 56; or 58-67); when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment).

Moreover, a variant of a polypeptide may include a polypeptide such as an immunoglobulin chain (e.g., REGN7075 (also referred to herein as bsAb7075); REGN6321 (also referred to herein as bsAb6321); REGN6322 (also referred to herein as bsAb6322); REGN6323 (also referred to herein as bsAb6323) $V_H$, $V_L$, HC or LC or CDR thereof) which may include the amino acid sequence of the reference polypeptide whose amino acid sequence is specifically set forth herein but for one or more (e.g., 1, 2, 3, 4, 5, 6, 7, 8, 9 or 10) mutations, e.g., one or more missense mutations (e.g., conservative substitutions), non-sense mutations, deletions, or insertions. For example, the present invention includes CD28×EGFR antigen-binding proteins which include an EGFR binding arm immunoglobulin light chain (or $V_L$) variant comprising the amino acid sequence set forth in SEQ ID NO: 16 but having one or more of such mutations and/or an immunoglobulin heavy chain (or $V_H$) variant comprising the amino acid sequence set forth in SEQ ID NO: 2 but having one or more of such mutations. In an embodiment of the invention, a CD28×EGFR antigen-binding protein includes an immunoglobulin light chain variant comprising LCDR1, LCDR2 and LCDR3 wherein one or more (e.g., 1 or 2 or 3) of such CDRs has one or more of such mutations (e.g., conservative substitutions) and/or an immunoglobulin heavy chain variant comprising HCDR1, HCDR2 and HCDR3 wherein one or more (e.g., 1 or 2 or 3) of such CDRs has one or more of such mutations (e.g., conservative substitutions).

A "conservatively modified variant" or a "conservative substitution", e.g., of an immunoglobulin chain set forth herein, refers to a variant wherein there is one or more substitutions of amino acids in a polypeptide with other amino acids having similar characteristics (e.g. charge, side-chain size, hydrophobicity/hydrophilicity, backbone conformation and rigidity, etc.). Such changes can frequently be made without significantly disrupting the biological activity of the antibody or fragment. Those of skill in this art recognize that, in general, single amino acid substitutions in non-essential regions of a polypeptide do not substantially alter biological activity (see, e.g., Watson et al. (1987) Molecular Biology of the Gene, The Benjamin/Cummings Pub. Co., p. 224 (4$^{th}$ Ed.)). In addition, substitutions of structurally or functionally similar amino acids are less likely to significantly disrupt biological activity. The present invention includes EGFR×CD28 and anti-EGFR antigen-binding proteins and/or binding arms comprising such conservatively modified variant immunoglobulin chains.

Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4)

aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Alternatively, a conservative replacement is any change having a positive value in the PAM250 log-likelihood matrix disclosed in Gonnet et al. (1992) Science 256: 1443-45.

Antigen-Binding Molecules

The antibodies of the present invention may be monospecific, bi-specific, or multispecific. Multispecific antibodies may be specific for different epitopes of one target polypeptide or may contain antigen-binding domains specific for more than one target polypeptide. See, e.g., Tutt et al., 1991, J. Immunol. 147:60-69; Kufer et al, 2004, Trends Biotechnol. 22:238-244. The anti-CD28 antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity.

Use of the expression "anti-CD28 antibody" herein is intended to include both monospecific anti-CD28 antibodies as well as multispecific (e.g., bispecific) antibodies comprising a CD28-binding arm and a second arm that binds a target antigen. Thus, the present invention includes bispecific antibodies wherein one arm of an immunoglobulin binds human CD28, and the other arm of the immunoglobulin is specific for a target antigen. The target antigen that the other arm of the CD28 bispecific antibody binds can be any antigen expressed on or in the vicinity of a cell, tissue, organ, microorganism or virus, against which a targeted immune response is desired. The CD28-binding arm can comprise any of the HCVR/LCVR or CDR amino acid sequences as set forth in Tables 3 and 8 herein. In certain embodiments, the CD28-binding arm binds human CD28 and induces human T-cell proliferation.

In the context of bispecific antibodies of the present invention wherein one arm of the antibody binds CD28 and the other arm binds a target antigen, the target antigen can be a tumor-associated antigen, such as EGFR.

According to certain exemplary embodiments, the present invention includes bispecific antigen-binding molecules that specifically bind CD28 and EGFR. Such molecules may be referred to herein as, e.g., "anti-CD28/anti-EGFR," or "anti-CD28×EGFR," or "CD28×EGFR" or "EGFR×CD28", or "anti-EGFR/anti-CD28," or "anti-EGFR×CD28," or "EGFR×CD28" bispecific molecules, or "anti-EGFR× anti-CD28" or "anti-CD28× anti-EGFR", or other similar terminology.

According to certain exemplary embodiments, the bispecific antigen-binding molecules (e.g., bispecific antibody) may have an effector arm and a targeting arm. The effector arm may be the first antigen-binding domain (e.g., anti-CD28 antibody) that binds to the antigens on effector cells (e.g., T cells). The targeting arm may be the second antigen binding domain (e.g., anti-/EGFR antibody) that binds to the antigens on target cells (e.g., tumor cells). According to certain exemplary embodiments, the effector arm binds to CD28 and the targeting arm binds to EGFR. The bispecific anti-CD28/EGFR may provide co-stimulatory signal to effector cells (e.g., T-cells).

As used herein, the expression "antigen-binding molecule" means a protein, polypeptide or molecular complex comprising or consisting of at least one complementarity determining region (CDR) that alone, or in combination with one or more additional CDRs and/or framework regions (FRs), specifically binds to a particular antigen. In certain embodiments, an antigen-binding molecule is an antibody or a fragment of an antibody, as those terms are defined elsewhere herein.

As used herein, the expression "bispecific antigen-binding molecule" means a protein, polypeptide or molecular complex (e.g. an antibody or antigen-binding fragment thereof) comprising at least a first antigen-binding domain and a second antigen-binding domain. Each antigen-binding domain within the bispecific antigen-binding molecule comprises at least one CDR that alone, or in combination with one or more additional CDRs and/or FRs, specifically binds to a particular antigen. In the context of the present invention, the first antigen-binding domain specifically binds a first antigen (e.g., CD28), and the second antigen-binding domain specifically binds a second, distinct antigen (e.g., EGFR).

In certain exemplary embodiments of the present invention, the bispecific antigen-binding molecule is a bispecific antibody. Each antigen-binding domain of a bispecific antibody comprises a heavy chain variable domain (HCVR) and a light chain variable domain (LCVR).

The first antigen-binding domain and the second antigen-binding domain may be directly or indirectly connected to one another to form a bispecific antigen-binding molecule of the present invention. Alternatively, the first antigen-binding domain and the second antigen binding domain may each be connected to a separate multimerizing domain. The association of one multimerizing domain with another multimerizing domain facilitates the association between the two antigen-binding domains, thereby forming a bispecific antigen-binding molecule. As used herein, a "multimerizing domain" is any macromolecule, protein, polypeptide, peptide, or amino acid that has the ability to associate with a second multimerizing domain of the same or similar structure or constitution. For example, a multimerizing domain may be a polypeptide comprising an immunoglobulin $C_H3$ domain. A non-limiting example of a multimerizing component is an Fc portion of an immunoglobulin (comprising a $C_H2$-$C_H3$ domain), e.g., an Fc domain of an IgG selected from the isotypes IgG1, IgG2, IgG3, and IgG4, as well as any allotype within each isotype group.

Bispecific antigen-binding molecules of the present invention will typically comprise two multimerizing domains, e.g., two Fc domains that are each individually part of a separate antibody heavy chain. The first and second multimerizing domains may be of the same IgG isotype such as, e.g., IgG1/IgG1, IgG2/IgG2, IgG4/IgG4. Alternatively, the first and second multimerizing domains may be of different IgG isotypes such as, e.g., IgG1/IgG2, IgG1/IgG4, IgG2/IgG4, etc.

In certain embodiments, the multimerizing domain is an Fc fragment or an amino acid sequence of 1 to about 200 amino acids in length containing at least one cysteine residues. In other embodiments, the multimerizing domain is a cysteine residue, or a short cysteine containing peptide. Other multimerizing domains include peptides or polypeptides comprising or consisting of a leucine zipper, a helix-loop motif, or a coiled-coil motif.

Any bispecific antibody format or technology may be used to make the bispecific antigen-binding molecules of the present invention. For example, an antibody or antigen-binding fragment thereof having a first antigen binding specificity can be functionally linked (e.g., by chemical coupling, genetic fusion, noncovalent association or otherwise) to one or more other molecular entities, such as another antibody or antibody fragment having a second antigen-binding specificity to produce a bispecific antigen-binding molecule. Specific exemplary bispecific formats that can be used in the context of the present invention include, without limitation, e.g., scFv-based or diabody bispecific formats, IgG-scFv fusions, dual variable domain (OVO)-Ig, Quadroma, knobs-into-holes, common light chain (e.g., common light chain with knobs-intoholes, etc.), CrossMab, CrossFab, (SEEO)body, leucine zipper, Ouobody, IgG1/IgG2, dual acting Fab (OAF)-IgG, and Mab² bispecific formats (see, e.g., Klein et al. 2012, mAbs 4:6, 1-11, and references cited therein, for a review of the foregoing formats).

In the context of bispecific antigen-binding molecules of the present invention, the multimerizing domains, e.g., Fc domains, may comprise one or more amino acid changes (e.g., insertions, deletions or substitutions) as compared to the wild-type, naturally occurring version of the Fc domain. For example, the invention includes bispecific antigen-binding molecules comprising one or more modifications in the Fc domain that results in a modified Fc domain having a modified binding interaction (e.g., enhanced or diminished) between Fc and FcRn. In one embodiment, the bispecific antigen-binding molecule comprises a modification in a $C_H2$ or a $C_H3$ region, wherein the modification increases the affinity of the Fc domain to FcRn in an acidic environment (e.g., in an endosome where pH ranges from about 5.5 to about 6.0). Non-limiting examples of such Fc modifications include, e.g., a modification at position 250 (e.g., E or Q); 250 and 428 (e.g., L or F); 252 (e.g., LN/FIW or T), 254 (e.g., S or T), and 256 (e.g., S/R/Q/EID or T); or a modification at position 428 and/or 433 (e.g., UR/S/P/Q or K) and/or 434 (e.g., H/F or V); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 2591 (e.g., V2591), and 308F (e.g., V308F) modification; a 433K (e.g., H433K) and a 434 (e.g., 434Y) modification; a 252,254, and 256 (e.g., 252Y, 254T, and 256E) modification; a 2500 and 428L modification (e.g., T250Q and M428L); and a 307 and/or 308 modification (e.g., 308F or 308P).

The present invention also includes bispecific antigen-binding molecules comprising a first $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second CH3 include: D16E, L 18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies.

In certain embodiments, the Fc domain may be chimeric, combining Fc sequences derived from more than one immunoglobulin isotype. For example, a chimeric Fc domain can comprise part or all of a $C_H2$ sequence derived from a human IgG1, human IgG2 or human IgG4 $C_H2$ region, and part or all of a $C_H3$ sequence derived from a human IgG1, human IgG2 or human IgG4. A chimeric Fc domain can also contain a chimeric hinge region. For example, a chimeric hinge may comprise an "upper hinge" sequence, derived from a human IgG1, a human IgG2 or a human IgG4 hinge region, combined with a "lower hinge" sequence, derived from a human IgG1, a human IgG2 or a human IgG4 hinge region. A particular example of a chimeric Fc domain that can be included in any of the antigen-binding molecules set forth herein comprises, from N- to C-terminus: [IgG4 CH1]-[IgG4 upper hinge]-[IgG2 lower hinge]-[IgG4 CH2]-[IgG4 $C_H3$]. Another example of a chimeric Fc domain that can be included in any of the antigen-binding molecules set forth herein comprises, from N- to C-terminus: [IgG1 CH1]-[IgG1 upper hinge]-[IgG2 lower hinge]-[IgG4 $C_H2$]-[IgG1 $C_H3$]. These and other examples of chimeric Fc domains that can be included in any of the antigen-binding molecules of the present invention are described in WO2014/022540 A1, Chimeric Fc domains having these general structural arrangements, and variants thereof, can have altered Fc receptor binding, which in turn affects Fc effector function.

Antibodies and antigen-binding fragments of the present invention comprise immunoglobulin chains including the amino acid sequences specifically set forth herein (and variants thereof) as well as cellular and in vitro post-translational modifications to the antibody or fragment. For example, the present invention includes antibodies and antigen-binding fragments thereof that specifically bind to EGFR and CD28 comprising heavy and/or light chain amino acid sequences set forth herein as well as antibodies and fragments wherein one or more asparagine, serine and/or threonine residues is glycosylated, one or more asparagine residues is deamidated, one or more residues (e.g., Met, Trp and/or His) is oxidized, the N-terminal glutamine is pyro-glutamate (pyroE) and/or the C-terminal lysine or other amino acid is missing.

Epidermal Growth Factor Receptor (EGFR) Binding Molecules and Anti-EGFR Antigen-Binding Arms The present invention includes multispecific (e.g., bispecific) antigen-binding proteins, e.g., antibodies or antigen-binding fragments, including one or more EGFR binding arms as well as one or more CD28 binding arms.

An EGFR binding arm is the portion of a multispecific antigen-binding protein that confers EGFR binding upon the protein. In an embodiment of the invention, the EGFR binding arm of the bispecific antibodies REGN7075, REGN6321, REGN6322 or REGN6323 blocks EGF binding to EGFR and in another embodiment of the invention, the EGFR binding arm does not block EGF binding to EGFR. For example, an EGFR-binding arm of a Y-shaped IgG antibody refers to a structural portion of the antibody that confers binding specificity to the EGFR. For example, in an embodiment of the invention, an EGFR Binding Arm comprises HCDR1, LCDR1, HCDR2, LCDR2, HCDR3 and LCDR3; a HCVR ($V_H$) and an LCVR ($V_L$) and/or a HC and LC that binds specifically to EGFR.

In an embodiment of the invention, an EGFR binding arm includes a heavy chain immunoglobulin that comprises a $V_H$ including the combination of heavy chain CDRs (HCDR1, HCDR2 and HCDR3) and the corresponding light chain immunoglobulin that comprises a $V_L$ including the combination of light chain CDRs (LCDR1, LCDR2 and LCDR3) which are set forth herein or in International patent application publication no. WO2014/004427.

"085N"; "086N"; "089N"; "102N"; "103N"; "116N"; "134P"; "136P"; "141 P"; "142P"; "143P"; "144P"; "145P"; "147P"; "151 P"; "153P"; "155P"; "157P"; "158P"; "159P"; "161 P"; "163P"; "169P" and "171 P" refers to the identification number of several anti-EGFR monospecific antibodies described in WO2014/004427. The HCVR arm of these antibodies may be used to combine with an anti-CD28 arm having HCVR amino acid sequences as described in Table 3 and a common light chain with the amino acid sequences as described in Table 6 to prepare a bispecific antibody to target a tumor cell expressing EGFR and a T cell expressing CD28. "REGN7075", "REGN6321", "REGN6322" or "REGN6323" also referred to respectively as "bsAb7075", "bsAb6321", "bsAb6322" or "bsAb6323" refers to bispecific antibodies comprising an EGFR Binding Arm including the immunoglobulin heavy chain variable region ($V_H$) or full length heavy chain (or a variant thereof) as set forth herein in Tables 1, 6 and 8 and the corresponding immunoglobulin light chain variable region ($V_L$) or full length light chain (or a variant thereof) set forth herein in Tables 1, 6 and 8 or that comprise a $V_H$ that comprises the CDRs thereof (HCDR1 (or a variant thereof), HCDR2 (or a variant thereof) and HCDR3 (or a variant thereof)) and the corresponding $V_L$ that comprises the CDRs thereof (LCDR1 (or a variant thereof), LCDR2 (or a variant thereof) and LCDR3 (or a variant thereof)), e.g., wherein the variable regions and/or CDRs comprise the specific amino acid sequences described herein and are not variants. Such a $V_H$ may comprise variant amino acid sequences wherein the CDR-Hs are not variants; and/or such a $V_L$ may comprise variant amino acid sequences wherein the CDR-Ls are not variants. Such EGFR binding arms may be referred to in the context of an EGFR×CD28 multispecific antigen-binding protein, e.g., 085N×14226P2. In an embodiment of the invention, the $V_H$ is linked to an IgG constant heavy chain domain (e.g., IgG1 or IgG4 (e.g., comprising a S228P mutation)) and/or the $V_L$ is linked to a lambda or kappa constant light chain domain.

The present invention also provides antigen-binding proteins, such as antibodies (e.g., human antibodies, monoclonal antibodies and recombinant antibodies) and antigen-binding fragments thereof, that specifically bind to EGFR protein or an antigenic fragment thereof (e.g., the extracellular domain of EGFR). Antigen-binding proteins that bind to the same epitope on EGFR as, or compete for binding to EGFR with any of the antigen-binding proteins set forth herein, are also part of the present invention.

Anti-EGFR antibodies and antigen-binding fragments thereof of the present invention include those comprising the CDRs (HCDR1, HCDR2 and HCDR3), $V_H$ or full length immunoglobulin sequence of the 085N; 086N; 089N; 102N; 103N; 116N; 134P; 136P; 141P; 142P; 143P; 144P; 145P; 147P; 151P; 153P; 155P; 157P; 158P; 159P; 161P; 163P; 169P; 171P; mAb12999P2, mAb13008P2, mAb35193P2, mAb13006P2, REGN7075, REGN6321, REGN6322 or REGN6323 EGFR binding arm as set forth herein or in WO2014/004427 (or a variant thereof); and/or the CDRs (LCDR1, LCDR2 and LCDR3), $V_L$ or full length immunoglobulin sequence of the 085N; 086N; 089N; 102N; 103N; 116N; 134P; 136P; 141P; 142P; 143P; 144P; 145P; 147P; 151P; 153P; 155P; 157P; 158P; 159P; 161P; 163P; 169P; 171P; mAb12999P2, mAb13008P2, mAb35193P2, mAb13006P2, REGN7075, REGN6321, REGN6322 or REGN6323 EGFR binding arm as set forth herein or in WO2014/004427 (or a variant thereof).

"REGN7075", "REGN6321", "REGN6322" or "REGN6323" may also refer to anti-EGFR antibodies and antigen-binding fragments thereof (e.g., monospecific antibodies and fragments) including the immunoglobulin heavy chain variable region ($V_H$) or full length heavy chain set forth herein (or a variant thereof); and the corresponding immunoglobulin light chain variable region ($V_L$) or full length light chain set forth herein (or a variant thereof); or that comprise a $V_H$ that comprises the CDRs thereof (HCDR1 (or a variant thereof), HCDR2 (or a variant thereof) and HCDR3 (or a variant thereof)) and the corresponding $V_L$ that comprises the CDRs thereof (LCDR1 (or a variant thereof), LCDR2 (or a variant thereof) and LCDR3 (or a variant thereof)), e.g., wherein the variable regions and/or CDRs comprise the specific amino acid sequences described herein and are not variants. Such a $V_H$ may comprise variant amino acid sequences wherein the CDR-Hs are not variants; and/or such a $V_L$ may comprise variant amino acid sequences wherein the CDR-Ls are not variants. In an embodiment of the invention, the $V_H$ is linked to an IgG constant heavy chain domain (e.g., IgG1 or IgG4) and/or the $V_L$ is linked to a lambda or kappa constant light chain domain.

The antigen-binding proteins REGN7075, REGN6321, REGN6322 and REGN6323 are bispecific anti-EGFR antigen-binding proteins (e.g., an antibody or antigen-binding fragment thereof) having one HCVR arm that binds to EGFR (and/or one or more different antigens or different EGFR epitopes) and having one HCVR arm that binds to CD28 on a T cell.

Amino acid sequences of the immunoglobulin chains of REGN7075, REGN6321, REGN6322 and REGN6323 are set forth below:

```
EGFR Components of REGN7075
HCVR of the EGFR arm from parental EGFR mAb12999P2):
                                        (SEQ ID NO: 2; CDRs underscored)
QVQLQESGPGLVKPSETLSLTCTVSGDSIITFYWSWIRQPPGRGLEWIGYIYYSGITNYNPSLKS
RVTISVDTSKNQVSLKLSSVTAADTAVYYCARVSEDSYFHYGMDVWGQGTTVTVSS (SEQ ID NO: 4)
CDR-H1: G D S I I T F Y (SEQ ID NO: 6)
CDR-H2: I Y Y S G I T (SEQ ID NO: 8)
CDR-H3: A R V S E D S Y F H Y G M D V Full length heavy chain of the EGFR arm of the bispecific antibody REGN7075
                                                       (SEQ ID NO: 24)
QVQLQESGPGLVKPSETLSLTCTVSGDSIITFYWSWIRQPPGRGLEWIGYIYYSGITNYNPSLKS
RVTISVDTSKNQVSLKLSSVTAADTAVYYCARVSEDSYFHYGMDVWGQGTTVTVSSASTKGPS
```

```
VFPLAPCSRSTSESTAALGCLVKDYFPEPVTVSWNSGALTSGVHTFPAVLQSSGLYSLSSVVT
VPSSSLGTKTYTCNVDHKPSNTKVDKRVESKYGPPCPPCPAPPVAGPSVFLFPPKPKDTLMIS
RTPEVTCVVVDVSQEDPEVQFNWYVDGVEVHNAKTKPREEQFNSTYRVVSVLTVLHQDWLN
GKEYKCKVSNKGLPSSIEKTISKAKGQPREPQVYTLPPSQEEMTKNQVSLTCLVKGFYPSDIAV
EWESNGQPENNYKTTPPVLDSDGSFFLYSRLTVDKSRWQEGNVFSCSVMHEALHNHYTQKS
LSLSLGK
```

LCVR of the EGFR and CD28 parental antibodies and the bispecific antibody
REGN7075

```
                                             (SEQ ID NO: 16; CDRs underscored)
EIVLTQSPGTLSLSPGERATLSCRASQSVSSSYLAWYQQKPGQAPRLLIYGASSRATGIPDRFS
GSGSGTDFTLTISRLEPEDFAVYYCQQYGSSPWTFGQGTKVEIK
```

```
                                             (SEQ ID NO: 18)
CDR-L1: QSVSSSY
```

```
                                             (SEQ ID NO: 20)
CDR-L2: GAS
```

```
                                             (SEQ ID NO: 22)
CDR-L3: QQYGSSPWT
```

Full length light chain of both EGFR and CD28 parental antibodies and the
bispecifics

```
                                             (SEQ ID NO: 28)
EIVLTQSPGTLSLSPGERATLSCRASQSVSSSYLAWYQQKPGQAPRLLIYGASSRATGIPDRFS
GSGSGTDFTLTISRLEPEDFAVYYCQQYGSSPWTFGQGTKVEIKRTVAAPSVFIFPPSDEQLKS
GTASVVCLLNNFYPREAKVQWKVDNALQSGNSQESVTEQDSKDSTYSLSSTLTLSKADYEKH
KVYACEVTHQGLSSPVTKSFNRGEC
```

EGFR Components of REGN6321
HCVR of the EGFR arm from parental EGFR mAb13008P2

```
                                             (SEQ ID NO: 30; CDRs underscored)
EVQLVESGGGLVRPGGSLRLSCTASGFTFSTFIMFWVRQAPGKGLEYVSSISSNGGTIYYADS
VKGRFTISRDNSKNTLYLQMGSLRAEDMAVYYCTRGGDFWSGYYPFDYWGQGTLVTVSS
```

```
                                             (SEQ ID NO: 32)
CDR-H1: G F T F S T F I
```

```
                                             (SEQ ID NO: 34)
CDR-H2: I S S N G GT I
```

```
                                             (SEQ ID NO: 36)
CDR-H3: T R G G D F W S G Y Y P F D Y
```

Full length heavy chain of the EGFR arm of the bispecific antibody REGN6321

```
                                             (SEQ ID NO: 38)
EVQLVESGGGLVRPGGSLRLSCTASGFTFSTFIMFWVRQAPGKGLEYVSSISSNGGTIYYADS
VKGRFTISRDNSKNTLYLQMGSLRAEDMAVYYCTRGGDFWSGYYPFDYWGQGTLVTVSSAST
KGPSVFPLAPCSRSTSESTAALGCLVKDYFPEPVTVSWNSGALTSGVHTFPAVLQSSGLYSLS
SVVTVPSSSLGTKTYTCNVDHKPSNTKVDKRVESKYGPPCPPCPAPPVAGPSVFLFPPKPKDT
LMISRTPEVTCVVVDVSQEDPEVQFNWYVDGVEVHNAKTKPREEQFNSTYRVVSVLTVLHQD
WLNGKEYKCKVSNKGLPSSIEKTISKAKGQPREPQVYTLPPSQEEMTKNQVSLTCLVKGFYPS
DIAVEWESNGQPENNYKTTPPVLDSDGSFFLYSRLTVDKSRWQEGNVFSCSVMHEALHNHYT
QKSLSLSLGK
```

LCVR of the EGFR and CD28 parental antibodies and the bispecific antibody
REGN6321

```
                                             (SEQ ID NO: 16; CDRs underscored)
EIVLTQSPGTLSLSPGERATLSCRASQSVSSSYLAWYQQKPGQAPRLLIYGASSRATGIPDRFS
GSGSGTDFTLTISRLEPEDFAVYYCQQYGSSPWTFGQGTKVEIK
```

```
                                             (SEQ ID NO: 18)
CDR-L1: QSVSSSY
```

```
                                             (SEQ ID NO: 20)
CDR-L2: GAS
```

```
                                             (SEQ ID NO: 22)
CDR-L3: QQYGSSPWT
```

Full length light chain of both EGFR and CD28 parental antibodies and the
bispecifics

```
                                             (SEQ ID NO: 28)
EIVLTQSPGTLSLSPGERATLSCRASQSVSSSYLAWYQQKPGQAPRLLIYGASSRATGIPDRFS
GSGSGTDFTLTISRLEPEDFAVYYCQQYGSSPWTFGQGTKVEIKRTVAAPSVFIFPPSDEQLKS
GTASVVCLLNNFYPREAKVQWKVDNALQSGNSQESVTEQDSKDSTYSLSSTLTLSKADYEKH
KVYACEVTHQGLSSPVTKSFNRGEC
```

EGFR Components of REGN6322
HCVR of the EGFR arm from parental EGFR mAb35193P2:
(SEQ ID NO: 40; CDRs underscored)
EVQLVESGGGLVKPGGSLRLSCTAS<u>GFSFRDAW</u>MTWVRQVPGKGLEWVGR<u>IRNKIDGGTTD</u>
YNTPVKDRFTISRDDSKNTLYLQMNSLKTEDTAVYYC<u>TTDIWNYVLFYYYGLDV</u>WGQGTTVTV
SS (SEQ ID NO: 42)
CDR-H1: G F S F R D A W (SEQ ID NO: 44)
CDR-H2: I R N K I D G G T T (SEQ ID NO: 46)
CDR-H3: T T D I W N Y V L F Y Y Y G L D V Full length heavy chain of the EGFR arm of the bispecific antibody REGN6322
(SEQ ID NO: 48)
EVQLVESGGGLVKPGGSLRLSCTASGFSFRDAWMTWVRQVPGKGLEWVGRIRNKIDGGTTD
YNTPVKDRFTISRDDSKNTLYLQMNSLKTEDTAVYYCTTDIWNYVLFYYYGLDVWGQGTTVTV
SSASTKGPSVFPLAPCSRSTSESTAALGCLVKDYFPEPVTVSWNSGALTSGVHTFPAVLQSSG
LYSLSSVVTVPSSSLGTKTYTCNVDHKPSNTKVDKRVESKYGPPCPPCPAPPVAGPSVFLFPP
KPKDTLMISRTPEVTCVVVDVSQEDPEVQFNWYVDGVEVHNAKTKPREEQFNSTYRVVSVLTV
LHQDWLNGKEYKCKVSNKGLPSSIEKTISKAKGQPREPQVYTLPPSQEEMTKNQVSLTCLVKG
FYPSDIAVEWESNGQPENNYKTTPPVLDSDGSFFLYSRLTVDKSRWQEGNVFSCSVMHEALH
NHYTQKSLSLSLGK LCVR of the EGFR and CD28 parental antibodies and the bispecific antibody
REGN6322
(SEQ ID NO: 16; CDRs underscored)
EIVLTQSPGTLSLSPGERATLSCRAS<u>QSVSSSY</u>LAWYQQKPGQAPRLLIY<u>GAS</u>SRATGIPDRFS
GSGSGTDFTLTISRLEPEDFAVYYC<u>QQYGSSPWT</u>FGQGTKVEIK (SEQ ID NO: 18)
CDR-L1: QSVSSSY (SEQ ID NO: 20)
CDR-L2: GAS (SEQ ID NO: 22)
CDR-L3: QQYGSSPWT Full length light chain of both EGFR and CD28 parental antibodies and the
bispecifics
(SEQ ID NO: 28)
EIVLTQSPGTLSLSPGERATLSCRASQSVSSSYLAWYQQKPGQAPRLLIYGASSRATGIPDRFS
GSGSGTDFTLTISRLEPEDFAVYYCQQYGSSPWTFGQGTKVEIKRTVAAPSVFIFPPSDEQLKS
GTASVVCLLNNFYPREAKVQWKVDNALQSGNSQESVTEQDSKDSTYSLSSTLTLSKADYEKH
KVYACEVTHQGLSSPVTKSFNRGEC EGFR Components of REGN6323
HCVR of the EGFR arm from parental EGFR mAb13006P2:
(SEQ ID NO: 50; CDRs underscored)
QVQLQESGPGLVKPSETLSLTCTVS<u>DDSIISYY</u>WSWIRQPPGKGLEWIGY<u>IYYSGRT</u>NYNPSLK
SRVTISVDTSKNQVSLKLNSVIAADTAVYYC<u>ARVSEDSYYHYGMDV</u>WGQGTTVTVSS (SEQ ID NO: 52)
CDR-H1: D D S I I S Y Y (SEQ ID NO: 54)
CDR-H2: I Y Y S G R T (SEQ ID NO: 56)
CDR-H3: A R V S E D S Y Y H Y G M D V Full length heavy chain of the EGFR arm of the bispecific antibody REGN6323
(SEQ ID NO: 58)
QVQLQESGPGLVKPSETLSLTCTVSDDSIISYYWSWIRQPPGKGLEWIGYIYYSGRTNYNPSLK
SRVTISVDTSKNQVSLKLNSVIAADTAVYYCARVSEDSYYHYGMDVWGQGTTVTVSSASTKGP
SVFPLAPCSRSTSESTAALGCLVKDYFPEPVTVSWNSGALTSGVHTFPAVLQSSGLYSLSSVV
TVPSSSLGTKTYTCNVDHKPSNTKVDKRVESKYGPPCPPCPAPPVAGPSVFLFPPKPKDTLMI
SRTPEVTCVVVDVSQEDPEVQFNWYVDGVEVHNAKTKPREEQFNSTYRVVSVLTVLHQDWLN
GKEYKCKVSNKGLPSSIEKTISKAKGQPREPQVYTLPPSQEEMTKNQVSLTCLVKGFYPSDIAV
EWESNGQPENNYKTTPPVLDSDGSFFLYSRLTVDKSRWQEGNVFSCSVMHEALHNHYTQKS
LSLSLGK -continued LCVR of the EGFR and CD28 parental antibodies and the bispecific antibody
REGN6323
(SEQ ID NO: 16; CDRs underscored)
EIVLTQSPGTLSLSPGERATLSCRAS<u>QSVSSSY</u>LAWYQQKPGQAPRLLIY<u>GAS</u>SRATGIPDRFS
GSGSGTDFTLTISRLEPEDFAVYYC<u>QQYGSSPWT</u>FGQGTKVEIK (SEQ ID NO: 18)
CDR-L1: QSVSSSY (SEQ ID NO: 20)
CDR-L2: GAS (SEQ ID NO: 22)
CDR-L3: QQYGSSPWT Full length light chain of both EGFR and CD28 parental antibodies and the
bispecifics
(SEQ ID NO: 28)
EIVLTQSPGTLSLSPGERATLSCRASQSVSSSYLAWYQQKPGQAPRLLIYGASSRATGIPDRFS
GSGSGTDFTLTISRLEPEDFAVYYCQQYGSSPWTFGQGTKVEIKRTVAAPSVFIFPPSDEQLKS
GTASVVCLLNNFYPREAKVQWKVDNALQSGNSQESVTEQDSKDSTYSLSSTLTLSKADYEKH
KVYACEVTHQGLSSPVTKSFNRGEC In an embodiment of the invention, an mAb12999P2, mAb13008P2, mAb35193P2, or mAb13006P2 heavy chain is paired with a light chain comprising an amino acid sequence selected from:

(SEQ ID NO: 16)
EIVLTQSPGTLSLSPGERATLSCRAS<u>QSVSSSY</u>LAWYQQKPGQAPRLLIY
<u>GAS</u>SRATGIPDRFSGSGSGTDFTLTISRLEPEDFAVYYC<u>QQYGSSPWT</u>FG
QGTKVEIK;
and (SEQ ID NO: 67)
DIQMTQSPSSLSASVGDRVTITCRAS<u>QSISSY</u>LNWYQQKPGKAPKLLIY<u>A
ASS</u>LQSGVPSRFSGSGSGTDFTLTISSLQPEDFATYYC<u>QQSYSTPPIT</u>FG
QGTRLEIK.

CD28 (Cluster of Differentiation 28) Binding Arms

The present invention includes multispecific (e.g., bispecific) antigen-binding proteins, e.g., antibodies or antigen-binding fragments, including one or more CD28 Binding Arms as well as one or more EGFR Binding Arms.

A CD28 Binding Arm is the portion of a multispecific antigen-binding protein that confers CD28 binding upon the protein. For example, a CD28-binding arm of a Y-shaped IgG antibody refers to a structural portion of the antibody that confers binding specificity to the CD28. For example, in an embodiment of the invention, a CD28 Binding Arm comprises HCDR1, LCDR1, HCDR2, LCDR2, HCDR3 and LCDR3; a HVCR ($V_H$) and an LCVR ($V_L$) and/or a HC and LC that binds specifically to CD28.

In an embodiment of the invention, a CD28 Binding Arm includes a heavy chain immunoglobulin that comprises a $V_H$ including the combination of heavy chain CDRs (HCDR1, HCDR2 and HCDR3) and the corresponding light chain immunoglobulin that comprises a $V_L$ including the combination of light chain CDRs (LCDR1, LCDR2 and LCDR3) which are set forth herein. In an embodiment of the invention, a CD28 Binding Arm includes a heavy chain variable region ($V_H$) and the corresponding light chain variable region ($V_L$) set forth herein.

Amino acid sequences of the immunoglobulin chains of parental anti-CD28 antibodies 14226P2, 14193P2 and 14216P2 are set forth below:

Parental CD28 mAbs used to prepare bispecifics mAb14226P2

HCVR of mAb14226P2
QVQLQESGPGLVKPSETLSLTCTVS<u>GGSISSYY</u>WSWIRQPPGKGLEWIGY<u>IYYSGIT</u>HYNPSLK
SRVTISVDTSKIQFSLKLSSVTAADTAVYYC<u>ARWGVRRDYYYYGMDV</u>WGQGTTVTVSS
(SEQ ID NO: 10)
CDR-H1: GGSISSYY (SEQ ID NO: 12)
CDR-H2: IYYSGIT (SEQ ID NO: 6)
CDR-H3: ARWGVRRDYYYYGMDV
Full length heavy chain of mAb14226P2
QVQLQESGPGLVKPSETLSLTCTVSGGSISSYYWSWIRQPPGKGLEWIGYIYYSGITHYNPSLK
SRVTISVDTSKIQFSLKLSSVTAADTAVYYCARWGVRRDYYYYGMDVWGQGTTVTVSSASTKG
PSVFPLAPCSRSTSESTAALGCLVKDYFPEPVTVSWNSGALTSGVHTFPAVLQSSGLYSLSSV
VTVPSSSLGTKTYTCNVDHKPSNTKVDKRVESKYGPPCPPCPAPPVAGPSVFLFPPKPKDTLM
ISRTPEVTCVVVDVSQEDPEVQFNWYVDGVEVHNAKTKPREEQFNSTYRVVSVLTVLHQDWL
NGKEYKCKVSNKGLPSSIEKTISKAKGQPREPQVYTLPPSQEEMTKNQVSLTCLVKGFYPSDIA
VEWESNGQPENNYKTTPPVLDSDGSFFLYSRLTVDKSRWQEGNVFSCSVMHEALHNRFTQK
SLSLSPGK (SEQ ID NO: 14)
(SEQ ID NO: 26)
LCVR of mAb 14226P2
EIVLTQSPGTLSLSPGERATLSCRAS<u>QSVSSSY</u>LAWYQQKPGQAPRLLIY<u>GAS</u>SRATGIPDRFS
GSGSGTDFTLTISRLEPEDFAVYYC<u>QQYGSSPWT</u>FGQGTKVEIK
(SEQ ID NO: 16)
CDR-L1: QSVSSSY (SEQ ID NO: 18)
CDR-L2: GAS (SEQ ID NO: 20)
CDR-L3: QQYGSSPWT (SEQ ID NO: 22)

-continued

---

Parental CD28 mAbs used to prepare bispecifics

Full length light chain of mAb14226P2
EIVLTQSPGTLSLSPGERATLSCRASQSVSSSYLAWYQQKPGQAPRLLIYGASSRATGIPDRFS
GSGSGTDFTLTISRLEPEDFAVYYCQQYGSSPWTFGQGTKVEIKRTVAAPSVFIFPPSDEQLKS
GTASVVCLLNNFYPREAKVQWKVDNALQSGNSQESVTEQDSKDSTYSLSSTLTLSKADYEKH
KVYACEVTHQGLSSPVTKSFNRGEC
(SEQ ID NO: 28)

mAb14193P2

HCVR of mAb14193P2
QVQLVESGGGVVQPGRSLRLSCAASGFTFSSYGMHWVRQAPGKGLEWVAVISYAGNNKYYA
DSVKGRFTVSRDNSKKTLYLQMNSLRSEDTAVYYCAKDSYYDFLTDPDVLDIWGQGTMVTVS
S
(SEQ ID NO: 59)
CDR-H1: GFTFSSYG (SEQ ID NO: 60)
CDR-H2: ISYAGNNK (SEQ ID NO: 61)
CDR-H3: AKDSYYDFLTDPDVLDI (SEQ ID NO: 62)
LCVR of mAb 14193P2
EIVLTQSPGTLSLSPGERATLSCRASQSVSSSYLAWYQQKPGQAPRLLIYGASSRATGIPDRFS
GSGSGTDFTLTISRLEPEDFAVYYCQQYGSSPWTFGQGTKVEIK
(SEQ ID NO: 16)
CDR-L1: QSVSSSY (SEQ ID NO: 18)
CDR-L2: GAS (SEQ ID NO: 20)
CDR-L3: QQYGSSPWT (SEQ ID NO: 22)

mAb14216P2

HCVR of mAb 14216P2
EVQLVESGGGLVQPGGSLRLSCAASGFTFSRNNMHWVRQAPGKGLEYVSGISSNGGRTYYA
DSVKGRFTISRDNSKNTLYLQMGGLRAADMAVYFCTRDDELLSFDYWGQGTLVTVSS
(SEQ ID NO: 63)
CDR-H1: GFTFSRNN (SEQ ID NO: 64)
CDR-H2: ISSNGGRT (SEQ ID NO: 65)
CDR-H3: TRDDELLSFDY (SEQ ID NO: 66)
[0125]
LCVR of mAb14216P2
EIVLTQSPGTLSLSPGERATLSCRASQSVSSSYLAWYQQKPGQAPRLLIYGASSRATGIPDRFS
GSGSGTDFTLTISRLEPEDFAVYYCQQYGSSPWTFGQGTKVEIK
(SEQ ID NO: 16)
CDR-L1: QSVSSSY (SEQ ID NO: 18)
CDR-L2: GAS (SEQ ID NO: 20)
CDR-L3: QQYGSSPWT (SEQ ID NO: 22)

---

In an embodiment of the invention, a 14226P2, 14193P2 or 14216P2 heavy chain is paired with a light chain comprising an amino acid sequence selected from:

(SEQ ID NO: 16)
EIVLTQSPGTLSLSPGERATLSCRASQSVSSSYLAWYQQKPGQAPRLLIY
GASSRATGIPDRFSGSGSGTDFTLTISRLEPEDFAVYYCQQYGSSPWTFG
QGTKVEIK;
and (SEQ ID NO: 67)
DIQMTQSPSSLSASVGDRVTITCRASQSISSYLNWYQQKPGKAPKLLIYA
ASSLQSGVPSRFSGSGSGTDFTLTISSLQPEDFATYYCQQSYSTPPITFG
QGTRLEIK.

"14226P2", "14193P2" or "14216P2" or "mAb14226P2", "mAb14193P2" or "mAb14216P2" refer to the parental monospecific antibodies from which the CD28 arms of the bispecifics described herein are obtained. CD28 Binding Arms including the immunoglobulin heavy chain variable region ($V_H$) or full length heavy chain set forth herein (or a variant thereof); and the corresponding immunoglobulin light chain variable region ($V_L$) or full length light chain set forth herein (or a variant thereof); or that comprise a $V_H$ that comprises the CDRs thereof (HCDR1 (or a variant thereof), HCDR2 (or a variant thereof) and HCDR3 (or a variant thereof)) and the corresponding $V_L$ that comprises the CDRs thereof (LCDR1 (or a variant thereof), LCDR2 (or a variant thereof) and LCDR3 (or a variant thereof)), e.g., wherein the variable regions and/or CDRs comprise the specific amino acid sequences described herein and which are not variants. Such a $V_H$ may comprise variant amino acid sequences wherein the CDR-Hs are not variants; and/or such a $V_L$ may comprise variant amino acid sequences wherein the CDR-Ls are not variants. Such CD28 binding arms may be referred to in the context of an EGFR×CD28 multispecific antigen-binding protein, e.g., 085N×14226P2. In an embodiment of the invention, the $V_H$ is linked to an IgG constant heavy chain domain (e.g., IgG1 or IgG4) and/or the $V_L$ is linked to a lambda or kappa constant light chain domain.

The present invention also provides antigen-binding proteins, such as antibodies (e.g., human antibodies, monoclonal antibodies and recombinant antibodies) and antigen-binding fragments thereof, that specifically bind to CD28 protein or an antigenic fragment thereof (e.g., the extracellular domain of CD28). Antigen-binding proteins that bind to the same epitope on CD28 as, or compete for binding to CD28 with any of the antigen-binding proteins set forth herein, are also part of the present invention.

The multispecific EGFR×CD28 antigen-binding proteins of the present invention which bind to CD28 on the surface of a T-cell and agonize CD28 signaling enhancing activation and/or proliferation of the T-cell may be referred to, herein, as "co-stimulatory" or "costimulatory". T-cell activation is initiated upon binding of the T-cell Receptor (TCR)/CD3 complex to peptide-MHC complexes ("signal 1"); activation is then enhanced by engagement of a second "co-stimulatory" receptor, such as the CD28 receptor on T-cells binding to its cognate ligand(s) on the target cell ("signal 2"). For example, activation of a T-cell by a CD28 bi-specific antibody may be caused by amplification of signals in response to endogenous tumor antigen recognition by the TCR/CD3 complex, or in response to "signal 1" activation via a CD3-bispecific.

Multispecific Antigen-Binding Proteins

The present invention provides antigen-binding proteins which are multispecific (e.g., bispecific) and bind at least to EGFR and CD28. As used herein, such an antibody is referred to in the format A×B wherein A refers to a binding arm in the multispecific molecule that binds to EGFR and B refers to a binding arm in the multispecific molecule that binds to CD28, or vice versa. EGFR×CD28 or CD28×EGFR refer to a multispecific antigen binding protein that binds to EGFR and CD28. The specific EGFR and CD28 binding arms in a multispecific antigen-binding protein also may be specified in an A×B format wherein A refers to a specific arm and B refers to another specific arm. For example, 085N×14226P2 refers to a multispecific antigen-binding protein that has the anti-EGFR binding arms of 085N as set forth herein and the anti-CD28 binding arms of 14426P2 as set forth herein. 085N, for example, is a binding arm including the 085N immunoglobulin heavy and light chains or variable regions thereof or CDRs thereof whose sequences are specifically set forth herein or are variants thereof.

In certain embodiments, the multispecific antigen-binding proteins comprise bispecific antigen-binding proteins. As used herein, the expression "bispecific antigen-binding protein" means a protein, polypeptide or molecular complex (e.g., antibody or antigen-binding fragment thereof) comprising at least a first antigen-binding domain and a second antigen-binding domain. Each antigen-binding domain within the bispecific antigen-binding molecule comprises at least one CDR that alone, or in combination with one or more additional CDRs and/or FRs, specifically binds to a particular antigen. In the context of the present invention, the first antigen-binding domain specifically binds a first antigen (e.g., CD28), and the second antigen-binding domain specifically binds a second, distinct antigen (e.g., EGFR).

Multispecific binding refers to binding to two or more different epitopes (EGFR and CD28 or more) which may be on the same or on different antigens. Multispecific includes bispecific, trispecific and tetraspecific.

The present invention includes any of the following multispecific antigen-binding proteins (e.g., bispecific antibodies or antigen-binding fragments thereof): REGN7075, REGN6321, REGN6322, REGN6323, as well as bispecific antibodies prepared by combining any of the EGFR HCVR arms of Table 1 (e.g., HCVR arms of the parental monoclonal antibodies mAb12999P2, mAb13008P2, mAb35193P2 and mAb13006P2) with any of the CD28 HCVR arms of Table 3 (e.g. HCVR arms of the parental mAb14226, mAb14193 and mAb14216) and methods of use thereof as set forth herein.

Polynucleotides and Methods of Making

An isolated polynucleotide encoding the immunoglobulin chains of any EGFR×CD28 multispecific antigen-binding protein or anti-EGFR antigen-binding protein set forth herein forms part of the present invention as does a vector comprising the polynucleotide and/or a host cell (e.g., Chinese hamster ovary (CHO) cell) comprising the polynucleotide, vector or antigen-binding protein set forth herein.

A polynucleotide includes DNA and RNA. The present invention includes any polynucleotide of the present invention, for example, encoding an immunoglobulin $V_H$, $V_L$, CDR-H, CDR-L, HC or LC of an EGFR Binding Arm and/or a CD28 Binding Arm, optionally, which is operably linked to a promoter or other expression control sequence. For example, the present invention provides any polynucleotide (e.g., DNA) that includes a nucleotide sequence set forth in Table 2 and a nucleotide sequence set forth in Table 4.

The present invention includes a polynucleotide comprising a nucleotide sequence set forth in SEQ ID NO: 1, 3, 5, 7, 9, 11, 13 15, 17, 21, 29, 31, 33, 35, 39, 41, 43, 45, 49, 51, 53, 55 and/or sequence ggggcaagt, optionally operably linked to a promoter or other expression control sequence or other polynucleotide sequence.

In general, a "promoter" or "promoter sequence" is a DNA regulatory region capable of binding an RNA polymerase in a cell (e.g., directly or through other promoter-bound proteins or substances) and initiating transcription of a coding sequence. A promoter may be operably linked to other expression control sequences, including enhancer and repressor sequences and/or with a polynucleotide of the invention. Promoters which may be used to control gene expression include, but are not limited to, cytomegalovirus (CMV) promoter (U.S. Pat. Nos. 5,385,839 and 5,168,062), the SV40 early promoter region (Benoist, et al., (1981) Nature 290:304-310), the promoter contained in the 3' long terminal repeat of Rous sarcoma virus (Yamamoto, et al., (1980) Cell 22:787-797), the herpes thymidine kinase promoter (Wagner, et al., (1981) Proc. Natl. Acad. Sci. USA 78:1441-1445), the regulatory sequences of the metallothionein gene (Brinster, et al., (1982) Nature 296:39-42); prokaryotic expression vectors such as the beta-lactamase promoter (Vllla-Komaroff, et al., (1978) Proc. Natl. Acad. Sci. USA 75:3727-3731), or the tac promoter (DeBoer, et al., (1983) Proc. Natl. Acad. Sci. USA 80:21-25); see also "Useful proteins from recombinant bacteria" in Scientific American (1980) 242:74-94; and promoter elements from yeast or other fungi such as the Ga/4 promoter, the ADC (alcohol dehydrogenase) promoter, PGK (phosphoglycerol kinase) promoter or the alkaline phosphatase promoter.

A polynucleotide encoding a polypeptide is "operably linked" to a promoter or other expression control sequence when, in a cell or other expression system, the sequence directs RNA polymerase mediated transcription of the coding sequence into RNA, preferably mRNA, which then may be RNA spliced (if it contains introns) and, optionally, translated into a protein encoded by the coding sequence.

The present invention includes polynucleotides encoding immunoglobulin polypeptide chains which are variants of those whose nucleotide sequence is specifically set forth herein. A "variant" of a polynucleotide refers to a polynucleotide comprising a nucleotide sequence that is at least about 70-99.9% (e.g., 70, 72, 74, 75, 76, 79, 80, 81, 82, 83, 84, 85, 86, 87, 88, 89, 90, 91, 92, 93, 94, 95, 96, 97, 98, 99, 99.5, 99.9%) identical to a referenced nucleotide sequence that is set forth herein; when the comparison is performed by a BLAST algorithm wherein the parameters of the algorithm are selected to give the largest match between the respective sequences over the entire length of the respective reference sequences (e.g., expect threshold: 10; word size: 28; max matches in a query range: 0; match/mismatch scores: 1, −2; gap costs: linear). In an embodiment of the invention, a variant of a nucleotide sequence specifically set forth herein comprises one or more (e.g., 1, 2, 3, 4, 5, 6, 7, 8, 9, 10, 11 or 12) point mutations, insertions (e.g., in frame insertions) or deletions (e.g., in frame deletions) of one or more nucleotides. Such mutations may, in an embodiment of the invention, be missense or nonsense mutations. In an embodiment of the invention, such a variant polynucleotide encodes an immunoglobulin polypeptide chain which can be incorporated into an EGFR Binding Arm and/or CD28 Binding Arm, i.e., such that the protein retains specific binding to EGFR and/or CD28.

Eukaryotic and prokaryotic host cells, including mammalian cells, may be used as hosts for expression of an anti-EGFR and EGFR×CD28 antigen-binding protein (e.g., antibody or antigen-binding fragment thereof) or an antigen binding arm thereof. Such host cells are well known in the art and many are available from the American Type Culture Collection (ATCC). These host cells include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Other cell lines that may be used are insect cell lines (e.g., *Spodoptera frugiperda* or *Trichoplusia ni*), amphibian cells, bacterial cells, plant cells and fungal cells. Fungal cells include yeast and filamentous fungus cells including, for example, *Pichia, Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Physcomitrella patens* and *Neurospora crassa*. The present invention includes an isolated host cell (e.g., a CHO cell or any type of host cell set forth above) comprising an anti-EGFR antibody (e.g., an EGFR antibody found in WO2014/004427) or an anti-EGFR× anti-CD28 antigen-binding protein of the present invention, such as REGN7075; REGN6321; REGN6322; REGN6323 and the anti-EGFR× anti-CD28 antigen-binding proteins shown in Tables 9A, 9B or 9C, or a polynucleotide encoding an immunoglobulin (Ig) heavy and/or light chain thereof); and/or one or more polynucleotides encoding the EGFR binding arm and CD28 binding arm of a multispecific antigen-binding protein of the present invention.

The present invention also includes a cell which is expressing an EGFR and/or CD28 or an antigenic fragment or fusion thereof (e.g., His$_6$ (SEQ ID NO: 68), Fc and/or myc) which is bound by an EGFR×CD28 and/or anti-EGFR antigen-binding protein of the present invention (e.g., an antibody or antigen-binding fragment thereof), for example, REGN7075, REGN6321, REGN6322, REGN6323, as well as bispecific antibodies prepared by combining any of the EGFR HCVR arms of Table 1 (e.g., HCVR arms of the parental monoclonal antibodies mAb12999P2, mAb13008P2, mAb35193P2 and mAb13006P2) with any of the CD28 HCVR arms of Table 3 (e.g. HCVR arms of the parental mAb14226, mAb14193 and mAb14216), or any of the bispecific antibodies shown in Tables 9A, 9B and 9C, for example, wherein the cell is in the body of a subject or is in vitro.

In addition, the present invention also provides a complex comprising an EGFR×CD28, and/or anti-EGFR antigen-binding protein of the present invention, e.g., antibody or antigen-binding fragment thereof, as discussed herein complexed with EGFR and/or CD28 polypeptide or an antigenic fragment thereof or fusion thereof and/or with a secondary antibody or antigen-binding fragment thereof (e.g., detectably labeled secondary antibody) that binds specifically to the anti-EGFR or EGFR×CD28 antibody or fragment. In an embodiment of the invention, the complex is in vitro (e.g., is immobilized to a solid substrate) or is in the body of a subject. In an embodiment of the invention, the EGFR is on the surface of a tumor cell and the CD28 is on the surface of an immune cell, e.g., a T-cell. In an embodiment of the invention, the T-cell is activated.

There are several methods by which to produce recombinant antibodies which are known in the art. One example of a method for recombinant production of antibodies is disclosed in U.S. Pat. No. 4,816,567. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, nucleic acid molecules may be introduced into mammalian cells by viral vectors. Methods of transforming cells are well known in the art. See, for example, U.S. Pat. Nos. 4,399,216; 4,912,040; 4,740,461 and 4,959,455.

The present invention includes recombinant methods for making an anti-EGFR×anti-CD28 (e.g., REGN7075, REGN6321, REGN6322 or REGN6323) antigen-binding protein of the present invention, such as an antibody or antigen-binding fragment thereof of the present invention, or an immunoglobulin chain thereof, comprising
  (i) introducing, into a host cell, one or more polynucleotides encoding the light and heavy immunoglobulin chains encoding the EGFR×CD28 or anti-EGFR antigen-binding protein's antigen binding arms for example, wherein the polynucleotide is in a vector; and/or integrates into the host cell chromosome and/or is operably linked to a promoter;
  (ii) culturing the host cell (e.g., CHO or *Pichia* or *Pichia pastoris*) under conditions favorable to expression of the polynucleotide and,
  (iii) optionally, isolating the antigen-binding protein (e.g., antibody or antigen-binding fragment) or chain from the host cell and/or medium in which the host cell is grown. The present invention also includes anti-EGFR or EGFR×CD28 antigen-binding proteins, such as antibodies and antigen-binding fragments thereof, which are the product of the production methods set forth herein, and, optionally, the purification methods set forth herein.

In an embodiment of the invention, a method for making an EGFR×CD28 (e.g., REGN7075, REGN6321, REGN6322 or REGN6323) antigen-binding protein, e.g., antibody or antigen-binding fragment thereof, includes a method of purifying the antigen-binding protein, e.g., by column chromatography, precipitation and/or filtration. As discussed, the product of such a method also forms part of the present invention.

Sequence Variants

The antibodies and bispecific antigen-binding molecules of the present invention may comprise one or more amino acid substitutions, insertions and/or deletions in the framework and/or CDR regions of the heavy and light chain variable domains as compared to the corresponding germline sequences from which the individual antigen-binding domains were derived. Such mutations can be readily ascertained by comparing the amino acid sequences disclosed herein to germ line sequences available from, for example, public antibody sequence databases. The antigen-binding molecules of the present invention may comprise antigen-binding fragments which are derived from any of the exemplary amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antigen-binding domain was originally derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germ line sequence from which the antigen-binding domain was originally derived). Furthermore, the antigen-binding domains may contain any combination of two or more germline mutations within the framework and/or CDR regions, e.g., wherein certain individual residues are mutated to the corresponding residue of a particular germ line sequence while certain other residues that differ from the original germ line sequence are maintained or are mutated to the corresponding residue of a different germline sequence. Once obtained, antigen-binding domains that contain one or more germline mutations can be easily tested for one or more desired properties such as improved binding specificity, increased binding affinity, improved or enhanced antagonistic or agonistic biological properties (as the case may be), reduced immunogenicity, etc. Bispecific antigen-binding molecules comprising one or more antigen-binding domains obtained in this general manner are encompassed within the present invention.

The present invention also includes antigen-binding molecules wherein one or both antigen-binding domains comprise variants of any of the HCVR, LCVR, and/or CDR amino acid sequences disclosed herein having one or more conservative substitutions. For example, the present invention includes antigen-binding molecules comprising an antigen-binding domain having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445. A "moderately conservative" replacement is any change having a nonnegative value in the PAM250 log-likelihood matrix.

The present invention also includes antigen-binding molecules comprising an antigen binding domain with an HCVR, LCVR, and/or CDR amino acid sequence that is substantially identical to any of the HCVR, LCVR, and/or CDR amino acid sequences disclosed herein. The term "substantial identity" or "substantially identical," when referring to an amino acid sequence means that two amino acid sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402.

Antibodies Comprising Fc Variants

According to certain embodiments of the present invention, anti-EGFRx anti-CD28 bispecific antigen binding molecules are provided comprising an Fc domain comprising one or more mutations which enhance or diminish antibody binding to the FcRn receptor, e.g., at acidic pH as compared to neutral pH. For example, the present invention includes antibodies and antigen binding molecules comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q);
250 and 428 (e.g., L or F);
252 (e.g., L/Y/F/W or T),
254 (e.g., S or T), and/or
256 (e.g., S/R/Q/E/D or T);
or a modification at position
428 and/or 433 (e.g., H/L/R/S/P/Q or K) and/or
434 (e.g., H/F or Y);
or a modification at position
250 and/or 428;
or a modification at position
307 or 308 (e.g., 308F, V308F), and/or
434.

In one embodiment, the modification comprises a 428L (e.g., M428L) and 434S (e.g., N434S) modification;
a 428L, 259I (e.g., V259I), and 308F (e.g., V308F) modification;
a 433K (e.g., H433K) and a 434 (e.g., 434Y) modification;
a 252, 254, and 256 (e.g., 252Y, 254T, and 256E) modification;
a 250Q and 428L modification (e.g., T250Q and M428L); and/or
a 307 and/or 308 modification (e.g., 308F or 308P).

For example, the present invention includes EGFR×CD28 bispecific antigen binding molecules comprising an Fc domain comprising one or more pairs or groups of mutations selected from the group consisting of:

250Q and 248L (e.g., T250Q and M248L);
252Y, 254T and 256E (e.g., M252Y, S254T and T256E);
428L and 434S (e.g., M428L and N434S); and
433K and 434F (e.g., H433K and N434F).

All possible combinations of the foregoing Fc domain mutations, and other mutations within the antibody variable domains disclosed herein, are contemplated within the scope of the present invention.

Biological Characteristics of the Antibodies and Antigen-Binding Molecules

The present invention includes antibodies and antigen-binding fragments thereof that bind human CD28 and EGFR with high affinity. The present invention also includes antibodies and antigen binding fragments thereof that bind human CD28 and/or EGFR with medium or low affinity, depending on the therapeutic context and particular targeting properties that are desired. For example, in the context of a bispecific antigen-binding molecule, wherein one arm binds CD28 and another arm binds a target antigen (e.g., EGFR), it may be desirable for the target antigen-binding arm to bind the target antigen with high affinity while the anti-CD28 arm binds CD28 with only moderate or low affinity. In this manner, preferential targeting of the antigen-binding molecule to cells expressing the target antigen may be achieved while avoiding general/untargeted CD28 binding and the consequent adverse side effects associated therewith.

According to certain embodiments, the present invention includes antibodies and antigen-binding fragments of antibodies that bind human CD28 (e.g., at 25° C.) with a $K_D$ of less than about 200 nM as measured by surface plasmon resonance, e.g., using an assay format as defined in Examples 1 and 13 herein. In certain embodiments, the antibodies or antigen-binding fragments of the present invention bind CD28 with a $K_D$ of less than about 100 nM, less than about 90 nM, less than about 80 nM, less than about 60 nM, less than about 40 nM, less than about 30 nM, less than 20 nM, less than 10 nM, or less than 5 nM as measured by surface plasmon resonance, e.g., using an assay format as defined in Examples 1 and 13 herein, or a substantially similar assay. In certain embodiments, the antibodies or antigen-binding fragments of the present invention bind CD28 with a $K_D$ between from about 5 nM to about 20 nM.

The present invention also includes antibodies and antigen-binding fragments thereof that bind CD28 with a dissociative half-life (t½) of greater than about 3 minutes as measured by surface plasmon resonance at 25° C. or 37° C., e.g., using an assay format as defined in Examples 1 and 13 herein, or a substantially similar assay. In certain embodiments, the antibodies or antigen-binding fragments of the present invention bind CD28 with a t % of greater than about 5 minutes, greater than about 10 minutes, greater than about 20 minutes, greater than about 30 minutes, greater than about 40 minutes, greater than about 50 minutes, greater than about 60 minutes, greater than about 70 minutes, greater than about 80 minutes, greater than about 90 minutes, greater than about 100 minutes, greater than about 200 minutes, greater than about 300 minutes, greater than about 400 minutes, greater than about 500 minutes, greater than about 600 minutes, greater than about 700 minutes, greater than about 800 minutes, greater than about 900 minutes, greater than about 1000 minutes, or greater than about 1200 minutes, as measured by surface plasmon resonance at 25° C. or 37° C., e.g., using an assay format as defined in Examples 1 and 13 herein, or a substantially similar assay.

The present invention includes bispecific antigen-binding molecules (e.g., bispecific antibodies) which are capable of simultaneously binding to human CD28 and human EGFR. According to certain embodiments, the bispecific antigen-binding molecules of the invention specifically interact with cells that express CD28 and/or EGFR. The extent to which a bispecific antigen-binding molecule binds cells that express CD28 and/or EGFR can be assessed by fluorescence activated cell sorting (FACS), as illustrated in Examples 10A and 10B herein. For example, the present invention includes bispecific antigen-binding molecules which specifically bind human cell lines which express CD28 but not EGFR (e.g., Jurkat cell), and human ovarian cancer cell lines which express EGFR but not CD28 (e.g., PEO1). In some embodiments, the bispecific antigen-binding molecules bind to CD28-expressing human or cynomolgus T-cells with an EC50 value less than $1\times10^{-5}$ M. In some embodiments, the bispecific antigen-binding molecules bind to CD28-expressing human or cynomolgus T-cells with an EC50 value of between $1\times10^{-12}$ M and $1\times10^{-5}$ M. In certain embodiments, the bispecific antigen-binding molecules bind to CD28-expressing human or cynomolgus T-cells with an EC50 value of between $1\times10^{-9}$ M and $1\times10^{-5}$ M. In certain embodiments, the bispecific antigen binding molecules bind to the surface of cell lines expressing EGFR with an $EC_{50}$ of less than about $2.5\times10^{-8}$ M. The binding of the bispecific antigen binding molecules to the surface of cells or cell lines can be measured by an in vitro FACS binding assay as described in Examples 10A and 10B.

EGFR×CD28 antigen-binding proteins set forth herein, e.g., comprising variant immunoglobulin chains, may exhibit one or more of the following properties:

Reduces the growth and/or survival of human tumor cells (e.g., A431 tumor cells) in a mouse (e.g., VH mouse (Rag2$^{null}$/γ$_c$$^{null}$/huSirp-a/huTPO)) engrafted with CD34+ cells (e.g., fetal liver CD34+ cells); optionally wherein the EGFR×CD28 is administered in association with a PD1 antagonist (e.g., anti-PD1 such as cemiplimab);

Reduces the growth and/or survival of human tumor cells (e.g., A431 tumor cells) in a mouse (e.g., (NOD/SCID/γ$_c$$^{null}$)) comprising human PBMCs (e.g., wherein human PBMCs mixed with the tumor cells are implanted subcutaneously into the mouse); optionally wherein the EGFR×CD28 is administered in association with a PD1 antagonist (e.g., anti-PD1 such as cemiplimab);

Reduces the growth and/or survival of human tumor cells (e.g., A549 tumor cells) in a mouse (e.g., NOD/SCID/γ$_c$$^{null}$) comprising human PBMCs (e.g., wherein human PBMCs are implanted intraperitoneally and the tumor cells are implanted subcutaneously into the mouse); optionally wherein the EGFR×CD28 is administered in association with a PD1 antagonist (e.g., anti-PD1 such as cemiplimab);

Binds to Jurkat CD28+ cells;

Binds to PE01 EGFR+ cells; and/or

Does not cause a significant cytokine release (e.g., interferon-gamma, IL-2, IL-6, IL-8 and/or IL-10) when administered to cynomolgus monkeys, e.g., at 10 mg/kg.

The present invention includes anti-EGFR and EGFR×CD28 bispecific antigen-binding molecules which are capable of depleting tumor cells in a subject (see, e.g., Examples 3-5). For example, according to certain embodiments, anti-EGFR and EGFR×CD28 bispecific antigen-binding molecules are provided, wherein a single administration of the antigen-binding molecule to a subject at a therapeutically effective dose causes a reduction in the number of tumor cells in the subject.

The present invention includes anti-EGFR× anti-CD28 bispecific antigen-binding molecules which are capable of binding to a variety of tumor cells, including A375 melanoma cells, 22RV1 prostate cells, PEO1 ovarian cells, CAPAN2 pancreatic cells, SW1990 pancreatic cells and H292 lung cells (See Examples 10A and 10B). As such, the bispecific antibodies of the invention may prove useful in treating a multitude of cancer indications.

The present invention includes anti-EGFR× anti-CD28 bispecific antigen-binding molecules which are capable of enhancing the cytotoxic potency of anti-tumor specific antigen (TSA)×anti-CD3 bispecific antibodies across a variety of cell lines (See Example 11). Using this approach, the TSA× CD3 bispecific antibody may include anti-STEAP2× anti-CD3, anti-PSMA× anti-CD3, or anti-MUC16×anti-CD3 bispecifics. The anti-EGFR× anti-CD28 antibodies may also prove useful when combined with a checkpoint inhibitor, for example, an antibody to PD-1 or PD-L1, or any other checkpoint inhibitor (See Example 9). In certain embodiments, it may be beneficial to combine the anti-EGFR× anti-CD28 with both an anti-TSA×anti-CD3 bispecific plus a checkpoint inhibitor.

The antibodies of the invention were also shown to bind certain epitopes on human EGFR using hydrogen-deuterium exchange (See Example 12). In particular, certain of the antibodies of the invention were found to bind to/interact with amino acid residues 345-368 of human EGFR (SEQ ID NO: 70), amino acid residues 399-416 of human EGFR (SEQ ID NO: 71) and amino acid residues 133-154 of human EGFR (SEQ ID NO: 72).

Epitope Mapping and Related Technologies

The epitope on CD28 or EGFR to which the antigen-binding molecules of the present invention bind may consist of a single contiguous sequence of 3 or more (e.g., 3, 4, 5, 6, 7, 8, 9, 10, 11, 12, 13, 14, 15, 16, 17, 18, 19, 20 or more) amino acids of a CD28 protein or a EGFR protein. Alternatively, the epitope may consist of a plurality of non-contiguous amino acids (or amino acid sequences) of CD28 or EGFR. The antibodies of the invention may interact with amino acids contained within a CD28 monomer, or may interact with amino acids on two different CD28 chains of a CD28 dimer. The term "epitope," as used herein, refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

Various techniques known to persons of ordinary skill in the art can be used to determine whether an antigen-binding domain of an antibody "interacts with one or more amino acids" within a polypeptide or protein. Exemplary techniques that can be used to determine an epitope or binding domain of a particular antibody or antigen-binding domain include, e.g., routine crossblocking assay such as that described in *Antibodies*, Harlow and Lane (Cold Spring Harbor Press, Cold Spring Harb., NY), point mutagenesis (e.g., alanine scanning mutagenesis, arginine scanning mutagenesis, etc.), peptide blots analysis (Reineke, 2004, Methods Mol Biol 248:443-463), protease protection, and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A. Alternatively, in certain embodiments, the protein of interest binds to the antibody, followed by hydrogen-deuterium exchange. After dissociation of the antibody, the target protein is subjected to protease cleavage and mass spectrometry analysis, thereby revealing the non-deuterium-labeled residues which correspond to the specific amino acids with which the antibody interacts. X-ray crystal structure analysis can also be used to identify the amino acids within a polypeptide with which an antibody interacts.

The present invention further includes anti-CD28 and anti-EGFR antibodies that bind to the same epitope as any of the specific exemplary antibodies described herein (e.g. antibodies comprising any of the amino acid sequences as set forth in Tables 1, 3, 6, 9A, 9B and 9C). Likewise, the present invention also includes anti-CD28 and/or anti-EGFR antibodies that compete for binding to CD28 and/or EGFR with any of the specific exemplary antibodies described herein (e.g. antibodies comprising any of the amino acid sequences as set forth in Tables 1, 3, 6, 9A, 9B and 9C herein).

The present invention also includes bispecific antigen-binding molecules comprising a first antigen-binding domain that specifically binds human CD28, and a second antigen binding fragment that specifically binds human EGFR, wherein the first antigen-binding domain binds to the same epitope on CD28 as any of the specific exemplary CD28-specific antigen-binding domains described herein, and/or wherein the second antigen-binding domain binds to the same epitope on EGFR as any of the specific exemplary EGFR-specific antigen-binding domains described herein.

In certain embodiments, the present invention includes bispecific antigen-binding molecules that interact with one or more of amino acid residues 133-154 of EGFR as set forth in SEQ ID NO: 72, or amino acid residues 345-368 of EGFR as set forth in SEQ ID NO: 70, or amino acid residues 399-416 of EGFR as set forth in SEQ ID NO: 71.

Likewise, the present invention also includes bispecific antigen-binding molecules comprising a first antigen-binding domain that specifically binds human CD28, and a second antigen binding fragment that specifically binds human EGFR, wherein the first antigen-binding domain competes for binding to CD28 with any of the specific exemplary CD28-specific antigen binding domains described herein, and/or wherein the second antigen-binding domain competes for binding to EGFR with any of the specific exemplary EGFR-specific antigen-binding domains described herein.

One can easily determine whether a particular antigen-binding molecule (e.g., antibody) or antigen-binding domain thereof binds to the same epitope as, or competes for binding with, a reference antigen-binding molecule of the present invention by using routine methods known in the art. For example, to determine if a test antibody binds to the same epitope on CD28 (or EGFR) as a reference bispecific antigen-binding molecule of the present invention, the reference bispecific molecule is first allowed to bind to a CD28 protein (or EGFR protein). Next, the ability of a test antibody to bind to the CD28 (or EGFR) molecule is assessed. If the test antibody is able to bind to CD28 (or EGFR) following saturation binding with the reference bispecific antigen-binding molecule, it can be concluded that the test antibody does not compete for binding to CD28 (or EGFR) with the reference bispecific antigen-binding molecule and/or that there is steric interference between antibodies that are binding different sites on the antigen. On the other hand, if the test antibody is not able to bind to the CD28 (or EGFR) molecule following saturation binding with the reference bispecific antigen-binding molecule, then the test antibody competes for binding to CD28 (or EGFR) with the reference bispecific antigen-binding molecule of the invention. Additional routine experimentation (e.g., peptide mutation and binding analyses) can then be carried out to confirm whether the observed lack of binding of the test antibody is in fact due to binding to the same epitope as the reference bispecific antigen-binding molecule or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antigen-binding proteins compete for binding to an antigen if, e.g., a 1-, 5-, 10-, 20- or 100-fold excess of one antigen-binding protein inhibits binding of the other by at least 50% but preferably 75%, 90% or even 99% as measured in a competitive binding assay (see, e.g., Junghans et al., Cancer Res. 1990:50:1495-1502). Alternatively, two antigen-binding proteins may bind to the same epitope if essentially all amino acid mutations in the antigen that reduce or eliminate binding of one antigen-binding protein reduce or eliminate binding of the other. Two antigen-binding proteins may have "overlapping epitopes" if only a subset of the amino acid mutations that reduce or eliminate binding of one antigen-binding protein reduce or eliminate binding of the other.

To determine if an antibody or antigen-binding domain thereof competes for binding with a reference antigen-binding molecule, the above-described binding methodology is performed in two orientations: In a first orientation, the reference antigen-binding molecule is allowed to bind to a CD28 protein (or EGFR protein) under saturating conditions followed by assessment of binding of the test antibody to the CD28 (or EGFR) molecule. In a second orientation, the test antibody is allowed to bind to a CD28 (or EGFR) molecule under saturating conditions followed by assessment of binding of the reference antigen-binding molecule to the CD28 (or EGFR) molecule. If, in both orientations, only the first (saturating) antigen-binding molecule is capable of binding to the CD28 (or EGFR) molecule, then it is concluded that the test antibody and the reference antigen-binding molecule compete for binding to CD28 (or EGFR). As will be appreciated by a person of ordinary skill in the art, an antibody that competes for binding with a reference antigen-binding molecule may not necessarily bind to the same epitope as the reference antibody, but may sterically block binding of the reference antibody by binding an overlapping or adjacent epitope.

Preparation of Antigen-Binding Domains and Construction of Bispecific Molecules

Antigen-binding domains specific for particular antigens can be prepared by any antibody generating technology known in the art. Once obtained, two different antigen-binding domains, specific for two different antigens (e.g., CD28 and EGFR), can be appropriately arranged relative to one another to produce a bispecific antigen-binding molecule of the present invention using routine methods. (A discussion of exemplary bispecific antibody formats that can be used to construct the bispecific antigen-binding molecules of the present invention is provided elsewhere herein). In certain embodiments, one or more of the individual components (e.g., heavy and light chains) of the multispecific antigen-binding molecules of the invention are derived from chimeric, humanized or fully human antibodies. Methods for making such antibodies are well known in the art. For example, one or more of the heavy and/or light chains of the bispecific antigen-binding molecules of the present invention can be prepared using VELOCIMMUNE™ technology. Using VELOCIMMUNE™ technology (or any other human antibody generating technology), high affinity chimeric antibodies to a particular antigen (e.g., CD28 or EGFR) are initially isolated having a human variable region and a mouse constant region. The antibodies are characterized and selected for desirable characteristics, including affinity, selectivity, epitope, etc. The mouse constant regions are replaced with a desired human constant region to generate fully human heavy and/or light chains that can be incorporated into the bispecific antigen-binding molecules of the present invention.

Genetically engineered animals may be used to make human bispecific antigen binding molecules. For example, a genetically modified mouse can be used which is incapable of rearranging and expressing an endogenous mouse immunoglobulin light chain variable sequence, wherein the mouse expresses only one or two human light chain variable domains encoded by human immunoglobulin sequences operably linked to the mouse kappa constant gene at the endogenous mouse kappa locus. Such genetically modified mice can be used to produce fully human bispecific antigen-binding molecules comprising two different heavy chains that associate with an identical light chain that comprises a variable domain derived from one of two different human light chain variable region gene segments. (See, e.g., US 2011/0195454 for a detailed discussion of such engineered mice and the use thereof to produce bispecific antigen-binding molecules).

Bioequivalents

The present invention encompasses antigen-binding molecules having amino acid sequences that vary from those of the described antibodies but that retain the ability to bind CD28 and EGFR. Such variant molecules comprise one or more additions, deletions, or substitutions of amino acids when compared to parent sequence, but exhibit biological activity that is essentially equivalent to that of the described antigen-binding molecules. Likewise, the antigen binding molecules-encoding DNA sequences of the present invention encompass sequences that comprise one or more additions, deletions, or substitutions of nucleotides when compared to the disclosed sequence, but that encode an antigen binding molecule that is essentially bioequivalent to the described antigen-binding molecules of the invention. Examples of such variant amino acid and DNA sequences are discussed above.

The present invention includes antigen-binding molecules that are bioequivalent to any of the exemplary antigen-binding molecules set forth herein. Two antigen-binding proteins or antibodies are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the exemplary bispecific antigen-binding molecules set forth herein may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include the exemplary bispecific antigen-binding molecules set forth herein comprising amino acid changes which modify the glycosylation characteristics of the antibodies, e.g., mutations which eliminate or remove glycosylation.

Species Selectivity and Species Cross-Reactivity

The present invention, according to certain embodiments, provides antigen-binding molecules that bind to human CD28 but not to CD28 from other species. The present invention also provides antigen-binding molecules that bind to human EGFR but not to EGFR from other species. The present invention also includes antigen-binding molecules that bind to human CD28 and to CD28 from one or more non-human species; and/or antigen-binding molecules that bind to human EGFR and to EGFR from one or more non-human species.

According to certain exemplary embodiments of the invention, antigen-binding molecules are provide which bind to human CD28 and/or human EGFR and may bind or not bind, as the case may be, to one or more of mouse, rat, guinea pig, hamster, gerbil, pig, cat, dog, rabbit, goat, sheep, cow, horse, camel, cynomolgus, marmoset, rhesus or chimpanzee CD28 and or EGFR. For example, in a particular exemplary embodiment of the present invention, bispecific antigen-binding molecules are provided comprising a first antigen-binding domain that binds human CD28 and cynomolgus CD28, and a second antigen-binding domain that specifically binds human EGFR.

Immunoconjugates

The invention encompasses EGFR×CD28 antigen-binding proteins, e.g., antibodies or antigen-binding fragments, such as REGN7075, REGN6321, REGN6322, REGN6323, or any combination of anti-EGFR HCVR pairing with an HCVR from any of the CD28 antibodies described herein, conjugated to another moiety, e.g., a therapeutic moiety (an "immunoconjugate"). In an embodiment of the invention, an anti-EGFR or EGFR×CD28 antigen-binding protein, e.g., antibody or antigen-binding fragment, is conjugated to any of the further therapeutic agents set forth herein. As used herein, the term "immunoconjugate" refers to an antigen-binding protein, e.g., an antibody or antigen-binding fragment, which is chemically or biologically linked to another antigen-binding protein, a drug, a radioactive agent, a reporter moiety, an enzyme, a peptide, a protein or a therapeutic agent.

In certain embodiments, the therapeutic moiety may be a cytotoxin, a chemotherapeutic drug, an immunosuppressant or a radioisotope. Cytotoxic agents include any agent that is detrimental to cells. Examples of suitable cytotoxic agents and chemotherapeutic agents for forming immunoconjugates are known in the art, (see for example, WO 05/103081).

Administration and Treatment

The present invention provides methods for administering an EGFR×CD28 multispecific antigen-binding protein of the present invention, e.g., REGN7075; REGN6321; REGN6322; REGN6323; or any combination of anti-EGFR HCVR pairing with an HCVR from any of the CD28 antibodies described herein, or a pharmaceutical composition thereof, to a subject (e.g., a human for example, who suffers from a hyperproliferative disorder), comprising introducing the antigen-binding protein or pharmaceutical composition into the body of the subject (e.g., a human), for example, parenterally. For example, the method comprises piercing the body of the subject with a needle of a syringe and injecting the antigen-binding protein or pharmaceutical composition into the body of the subject, e.g., into the vein, artery, tumor, muscular tissue or subcutis of the subject.

The mode of administration of an EGFR×CD28 or anti-EGFR antigen-binding protein or pharmaceutical composition thereof can vary. Routes of administration include parenteral, non-parenteral, oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, intraocular, intravitreal, transdermal or intra-arterial.

The present invention also provides a vessel (e.g., a plastic or glass vial or ampule, e.g., with a cap or a chromatography column, hollow bore needle or a syringe cylinder) comprising an EGFR×CD28 or anti-EGFR antigen-binding protein of the present invention or a pharmaceutical composition thereof.

The present invention also provides an injection device comprising one or more antigen-binding proteins (e.g., antibody or antigen-binding fragment) that bind specifically to EGFR or EGFR and CD28 (EGFR×CD28) or a pharmaceutical formulation thereof. The injection device may be packaged into a kit. An injection device is a device that introduces a substance into the body of a subject via a parenteral route, e.g., intramuscular, subcutaneous or intravenous. For example, an injection device may be a syringe or an auto-injector (e.g., pre-filled with the pharmaceutical formulation) which, for example, includes a cylinder or barrel for holding fluid to be injected (e.g., comprising the antibody or fragment or a pharmaceutical formulation thereof), a needle for piercing skin, blood vessels or other tissue for injection of the fluid; and a plunger for pushing the fluid out of the cylinder and through the needle bore and into the body of the subject.

A pre-filled syringe is a syringe which has been filled with a composition (e.g. a pharmaceutical composition comprising a multispecific antigen-binding protein and a pharmaceutically acceptable carrier) prior to sale or transfer to an end-user, e.g., a physician or care-giver, who is to administer the composition to a patient/subject.

Therapeutic Uses of the Antigen-Binding Molecules

The present invention provides methods for treating or preventing a hyperproliferative disease in a subject, comprising administering a therapeutically effective dose of EGFR×CD28 antigen-binding protein (e.g., REGN7075; REGN6321; REGN6322; REGN6323; or any combination of anti-EGFR HCVR pairing with an HCVR from any of the CD28 antibodies described herein to the subject; optionally in association with a PD-1 and/or PD-L1 inhibitor such as an antibody (e.g., pembrolizumab, nivolumab and/or cemiplimab) or antigen-binding fragment thereof. In an embodiment of the invention, the method includes the step of determining whether the cancer in the subject expresses EGFR. If such expression is observed, then the EGFR×CD28 and/or anti-EGFR antigen-binding protein is administered. For example, in an embodiment of the invention, the method comprises taking a biopsy of the cancer (e.g., which is performed by a treating physician) and either determining whether the cells of the cancer express EGFR or directing another individual or entity (e.g., on behalf of the patient or subject) to perform such a determination and, if EGFR expression is present, then administering the anti-EGFR or EGFR×CD28 antigen-binding protein to the subject. In an embodiment of the invention, the physician directs some other individual or entity, for example, a pathologist (e.g., on behalf of the patient or subject) to perform the biopsy. In an embodiment of the invention, EGFR expression is tested immunohistochemically (IHC) or by ELISA (enzyme linked immunosorbent assay).

The present invention includes methods including administering to a subject in need thereof a therapeutic composition comprising a bispecific antigen binding molecule that specifically binds EGFR, or CD28 and EGFR. The therapeutic composition can comprise any of the antibodies or bispecific antigen-binding molecules as disclosed herein and a pharmaceutically acceptable carrier or diluent.

The antibodies and bispecific antigen-binding molecules of the invention (and therapeutic compositions comprising the same) are useful, inter alia, for treating any disease or disorder in which stimulation, activation and/or targeting of an immune response would be beneficial. In particular, the anti-EGFR, or EGFR×CD28 bispecific antigen-binding molecules of the present invention may be used for the treatment, prevention and/or amelioration of any disease or disorder associated with or mediated by EGFR expression or activity or the proliferation of EGFR+ cells. The mechanisms of action by which the therapeutic methods of the invention are achieved include killing of the cells expressing EGFR in the presence of effector cells, for example, T-cells. Cells expressing EGFR which can be inhibited or killed using the bispecific antigen-binding molecules of the invention include, for example, lung cancer cells.

As used herein, the term "subject" refers to a mammal (e.g., rat, mouse, cat, dog, cow, sheep, horse, goat, rabbit), preferably a human, for example, in need of prevention and/or treatment of an EGFR-expressing cancer. The subject may have an EGFR-expressing cancer, be predisposed to developing such a condition, and/or would benefit from an inhibition or reduction in EGFR activity or a depletion of EGFR+ cells. In one embodiment, the subject may have, or be at risk of developing, a hyperproliferative disease.

A hyperproliferative disease, for the purposes herein, refers to a disease characterized by abnormal, excessive and/or uncontrolled cell growth, e.g., wherein the cells express EGFR. For example, hyperproliferative diseases include EGFR-expressing cancers. A wide range of cancers express EGFR. Exemplary EGFR-expressing cancers include, but are not limited to esophageal carcinoma, lung squamous cell carcinoma, lung adenocarcinoma, cervical squamous cell carcinoma, glioma, thyroid cancer, lung cancer (e.g., non-small cell lung cancer), colorectal cancer, colon cancer, bladder cancer, rectal cancer, head and neck cancer, stomach cancer, liver cancer, pancreatic cancer, renal cancer, urothelial cancer, prostate cancer, testis cancer, breast cancer, cervical cancer, endometrial cancer, ovarian cancer, gastroesophageal cancer, (e.g., gastroesophageal adenocarcinoma), and melanoma. Accordingly, the antibodies and the bispecific antigen-binding molecules of the present invention can be used in treating a wide range of cancers.

Cancer characterized by solid tumor cells or cancerous blood cells, which may be an EGFR-expressing cancer e.g., wherein EGFR expression in the cells of the particular subject to be treated has been confirmed, includes esophageal carcinoma, lung squamous cell carcinoma, lung adenocarcinoma, cervical squamous cell carcinoma, endometrial adenocarcinoma, bladder urothelial carcinoma, lung cancer (e.g., non-small cell lung cancer), colorectal cancer, rectal cancer, endometrial cancer, skin cancer (e.g., head & neck squamous cell carcinoma), brain cancer (e.g., glioblastoma multiforme), breast cancer, gastroesophageal cancer, (e.g., gastroesophageal adenocarcinoma), prostate cancer and/or ovarian cancer.

The antigen-binding molecules of the present invention may also be used to treat, e.g., primary and/or metastatic tumors arising in the colon, lung, breast, renal cancer, and bladder (or from any cancer discussed herein). According to certain exemplary embodiments, the bispecific antigen binding molecules of the present invention are used to treat an ovarian cancer.

The present invention also includes methods for treating residual cancer in a subject. As used herein, the term "residual cancer" means the existence or persistence of one or more cancerous cells in a subject following treatment with an anti-cancer therapy.

According to certain aspects, the present invention provides methods for treating a hyperproliferative disease, e.g., which is associated with EGFR expression (e.g., lung cancer), comprising administering one or more of the anti-EGFR, or EGFR×CD28 bispecific antigen-binding molecules, as described herein to a subject, for example, after the subject has been shown to be non-responsive to other types of anti-cancer therapies. For example, the present invention includes methods for treating a hyperproliferative disease such as lung cancer comprising administering an anti-EGFR or EGFR×CD28 bispecific antigen-binding molecule to a patient or subject 1 day, 2 days, 3 days, 4 days, 5 days, 6 days, 1 week, 2 weeks, 3 weeks or 4 weeks, 2 months, 4 months, 6 months, 8 months, 1 year, or more after the subject has received the standard of care for patients suffering from cancer, e.g., lung cancer. In other aspects, an anti-EGFR or EGFR×CD28 bispecific antigen-binding molecule of the invention comprising an IgG4 Fc domain is initially administered to a subject at one or more time points (e.g., to provide robust initial depletion of ovarian cancer cells), followed by administration of an equivalent bispecific antigen-binding molecule comprising a different IgG domain, such as an IgG1 Fc domain, at subsequent time points. It is envisioned that the anti-EGFR or EGFR×CD28 antibodies of the invention may be used in conjunction with other bispecific antigen binding molecules, such as with an anti-EGFR/anti-CD3 bispecific antibody. It is also envisioned that the bispecific antibodies of the invention will be used in conjunction with further therapeutic agents, for example, those that target PD-1, and other targets. It may be advantageous to combine two bispecific antibodies that target the same tumor antigen (e.g., EGFR), but with one of the bispecifics targeting the CD3 on T-cells and the other bispecific targeting a co-stimulator molecule like CD28. This combination may be used alone to enhance tumor cell killing, or may be used in combination with a checkpoint inhibitor.

An "effective" or "therapeutically effective" dose of EGFR×CD28 or anti-EGFR antigen-binding protein, e.g., antibody or antigen-binding fragment, for treating or preventing a hyperproliferative disease, such as an EGFR-expressing cancer, is the amount of the antigen-binding protein sufficient to alleviate one or more signs and/or symptoms of the disease in the treated subject, whether by inducing the regression or elimination of such signs and/or symptoms or by inhibiting the progression of such signs and/or symptoms. In an embodiment of the invention, a therapeutically effective dose of anti-EGFR or EGFR×CD28 antigen-binding protein is 0.1-2000 mg, e.g., 0.1 mg IV (intravenously) Q2W (every two weeks) to 2000 mg IV Q2W. The dose amount may vary depending upon the age and the size of a subject to be administered, target disease, conditions, route of administration, and the like. In certain embodiments, the initial dose may be followed by administration of a second or a plurality of subsequent doses of antigen-binding protein in an amount that can be approximately the same or less or more than that of the initial dose, wherein the subsequent doses are separated by 2 weeks.

The dose of antigen-binding molecule administered to a patient may vary depending upon the age and the size of the patient, target disease, conditions, route of administration, and the like. The preferred dose is typically calculated according to body weight or body surface area. Depending on the severity of the condition, the frequency and the duration of the treatment can be adjusted. Effective dosages and schedules for administering a bispecific antigen-binding molecule may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

According to certain embodiments of the present invention, multiple doses of an antigen-binding molecule (e.g., an anti-CD28 antibody or a bispecific antigen-binding molecule that specifically binds EGFR and CD28) may be administered to a subject over a defined time course. The methods according to this aspect of the invention comprise sequentially administering to a subject multiple doses of an antigen-binding molecule of the invention. As used herein, "sequentially administering" means that each dose of an antigen-binding molecule is administered to the subject at a different point in time, e.g., on different days separated by a predetermined interval (e.g., hours, days, weeks or months). The present invention includes methods which comprise sequentially administering to the patient a single initial dose of an antigen-binding molecule, followed by one or more secondary doses of the antigen-binding molecule, and optionally followed by one or more tertiary doses of the antigen-binding molecule.

The terms "initial dose," "secondary doses," and "tertiary doses," refer to the temporal sequence of administration of the antigen-binding molecule of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of the antigen-binding molecule, but may differ from one another in terms of frequency of administration. In certain embodiments, however, the amount of an antigen-binding molecule contained in the initial, secondary and/or tertiary doses varies from one another (e.g., adjusted up or down as appropriate) during the course of treatment. In certain embodiments, two or more doses are administered at the beginning of the treatment regimen as "loading doses" followed by subsequent doses that are administered on a less frequent basis (e.g., "maintenance doses").

In one exemplary embodiment of the present invention, each secondary and/or tertiary dose is administered from one to several weeks after the immediately preceding dose. The phrase "the immediately preceding dose," as used herein, means, in a sequence of multiple administrations, the dose of antigen-binding molecule which is administered to a patient prior to the administration of the very next dose in the sequence with no intervening doses.

The methods according to this aspect of the invention may comprise administering to a patient any number of secondary and/or tertiary doses of an antigen-binding molecule (e.g., an anti-CD28 antibody or a bispecific antigen-binding molecule that specifically binds EGFR and CD28). For example, in certain embodiments, only a single secondary dose is administered to the patient. In other embodiments, two or more secondary doses are administered to the patient. Likewise, in certain embodiments, only a single tertiary dose is administered to the patient. In other embodiments, two or more tertiary doses are administered to the patient.

In embodiments involving multiple secondary doses, each secondary dose may be administered at the same frequency as the other secondary doses. Similarly, in embodiments involving multiple tertiary doses, each tertiary dose may be administered at the same frequency as the other tertiary doses. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

Diagnostic Uses

The bispecific antibodies of the present invention may also be used to detect and/or measure CD28 or EGFR, or CD28-expressing or EGFR-expressing cells in a sample, e.g., for diagnostic purposes. For example, anti-EGFR or EGFR×CD28 antibody or antigen-binding fragment thereof, may be used to diagnose a condition or disease characterized by aberrant expression (e.g., over-expression, under-expression, lack of expression, etc.) of CD28 or EGFR. Exemplary diagnostic assays for CD28 or EGFR may comprise, e.g., contacting a sample, obtained from a patient, with an antibody of the invention, wherein the antibody is labeled with a detectable label or reporter molecule. Alternatively, an unlabeled antibody can be used in diagnostic applications in combination with a secondary antibody which is itself detectably labeled. The detectable label or reporter molecule can be a radioisotope, such as $^3H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, betagalactosidase, horseradish peroxidase, or luciferase. Specific exemplary assays that can be used to detect or measure CD28 or EGFR in a sample include enzyme-linked immunosorbent assay (ELISA), radioimmunoassay (RIA), and fluorescence-activated cell sorting (FACS). Samples that can be used in CD28 or EGFR diagnostic assays according to the present invention include any tissue or fluid sample obtainable from a patient which contains detectable quantities of CD28 or EGFR protein, or fragments thereof, under normal or pathological conditions. Generally, levels of CD28 or EGFR in a particular sample obtained from a healthy patient (e.g., a patient not afflicted with a disease or condition associated with abnormal CD28 or EGFR levels or activity) will be measured to initially establish a baseline, or standard, level of CD28 or EGFR. This baseline level of CD28 or EGFR can then be compared against the levels of CD28 or EGFR measured in samples obtained from individuals suspected of having a CD28 or EGFR related disease or condition.

Combinations and Pharmaceutical Formulations

The present invention provides compositions that include EGFR×CD28 and/or anti-EGFR antigen-binding proteins and one or more ingredients; as well as methods of use thereof and methods of making such compositions. Pharmaceutical formulations (e.g., aqueous pharmaceutical formulations that include water) comprising an EGFR×CD28 or anti-EGFR antigen-binding protein or the present invention and a pharmaceutically acceptable carrier or excipient are part of the present invention.

The present invention provides pharmaceutical compositions comprising the antigen binding molecules of the present invention. The pharmaceutical compositions of the invention can be formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFECTIN™, Life Technologies, Carlsbad, CA), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

To prepare pharmaceutical formulations of the EGFR× CD28 antigen-binding proteins, e.g., antibodies and antigen-binding fragments thereof (e.g., REGN7075; REGN6321; REGN6322; REGN6323; or any combination of anti-EGFR HCVR pairing with an HCVR from any of the CD28 antibodies described herein, the antigen-binding protein is admixed with a pharmaceutically acceptable carrier or excipient. See, e.g., Remington's Pharmaceutical Sciences and U.S. Pharmacopeia: National Formulary, Mack Publishing Company, Easton, Pa. (1984); Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y. In an embodiment of the invention, the pharmaceutical formulation is sterile. Such compositions are part of the present invention.

Pharmaceutical formulations of the present invention include an EGFR×CD28 or anti-EGFR antigen-binding protein and a pharmaceutically acceptable carrier including, for example, water, buffering agents, preservatives and/or detergents.

The scope of the present invention includes desiccated, e.g., freeze-dried compositions, comprising an EGFR× CD28 or anti-EGFR antigen-binding protein, e.g., antibody or antigen-binding fragment thereof, or a pharmaceutical formulation thereof that includes a pharmaceutically acceptable carrier but substantially lacks water.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

As discussed herein, the present invention provides a vessel (e.g., a plastic or glass vial) or injection device (e.g., syringe, pre-filled syringe or autoinjector) comprising any of the EGFR×CD28 or anti-EGFR antigen-binding proteins herein, e.g., antibodies or antigen-binding fragments thereof, or a pharmaceutical formulation comprising a pharmaceutically acceptable carrier or excipient thereof.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable and disposable pens and autoinjector delivery devices have applications in the subcutaneous delivery of a pharmaceutical composition of the present invention. See e.g., AUTOPEN™ (Owen Mumford, Inc., Woodstock, UK) or the HUMIRA™ Pen (Abbott Labs, Abbott Park, IL)

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Florida. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138).

Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline and other isotonic solutions which may be used in combination with an appropriate solubilizing agent. Injectable oily mediums are also part of the present invention. Such oily mediums may be combined with a solubilizing agent.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 0.1 to about 2000 mg per dosage form in a unit dose; especially in the form of injection.

The present invention includes compositions and therapeutic formulations comprising any of the exemplary antibodies and bispecific antigen-binding molecules described herein in combination with one or more additional therapeutically active components, and methods of treatment comprising administering such combinations to subjects in need thereof.

Exemplary additional therapeutic agents that may be combined with or administered in association with an antigen-binding molecule of the present invention include, e.g., chemotherapy (e.g., anti-cancer chemotherapy, for example, paclitaxel, docetaxel, vincristine, cisplatin, carboplatin or oxaliplatin), radiation therapy, checkpoint inhibitors that target PD-1 (e.g., an anti-PD-1 antibody such as pembrolizumab, nivolumab, or cemiplimab (see U.S. Pat. No. 9,987, 500)), CTLA-4, LAG3, TIM3, and others, costimulatory agonist bivalent antibodies that target molecules such as GITR, OX40, 4-1 BB, and others), other costimulatory CD28 bispecific antibodies, and multispecific (e.g., bispecific) antibodies and antigen-binding fragments thereof that bind a tumor associated antigen (e.g., MUC16 (mucin 16), PSMA, or STEAP2) and, for example, CD3 (MUC16×CD3, PSMA×CD3, or STEAP2×CD3). Exemplary bispecific antibodies comprising an antigen binding domain that binds CD3 include, but are not limited to those described in, e.g., WO2017/053856A1, WO2014/047231A1, WO2018/067331A1 and WO2018/058001A1. EGFR is expressed in a wide range of cancers. Accordingly, the bispecific anti-EGFR×CD28 antibodies of the present invention can be used in combination with a wide range of bispecific antibodies comprising an antigen-binding domain that binds CD3 in treatments of various cancers.

In a further embodiment of the invention, a further therapeutic agent that is administered to a subject in association with an EGFR×CD28 and/or anti-EGFR antigen-binding protein, e.g., antibody or antigen-binding fragment thereof, is administered to the subject in accordance with the Physicians' Desk Reference 2003 (Thomson Healthcare; 57$^{th}$ edition (Nov. 1, 2002)) or the approved prescribing information normally provided with the particular agent.

Methods for treating or preventing an EGFR expressing cancer in a subject in need of said treatment or prevention by administering a therapeutically effective dose amount EGFR×CD28 and/or anti-EGFR antigen-binding protein, in association with a further therapeutic agent are part of the present invention.

The term "in association with" indicates that components, an EGFR×CD28 or anti-EGFR antigen-binding protein, e.g., antibody or antigen-binding fragment thereof of the present invention, along with a further therapeutic agent, such as cemiplimab, can be formulated into a single composition, e.g., for simultaneous delivery, or formulated separately into two or more compositions (e.g., a kit including each component). Components administered in association with each another can be administered to a subject at a different time than when the other component is administered; for example, each administration may be given non-simultaneously (e.g., separately or sequentially) at intervals over a given period of time as part of a treatment regimen. Separate components administered in association with each another may also be administered sequentially, though essentially simultaneously, during the same administration session. Moreover, the separate components administered in association with each another may be administered to a subject by the same or by a different route.

EXAMPLES

The following examples are put forth so as to provide those of ordinary skill in the art with a complete disclosure and description of how to make and use the methods and compositions of the invention, and are not intended to limit the scope of what the inventors regard as their invention.

Example 1: Construction of Anti-EGFR×CD28 Antibodies

Generation of Anti-EGFR Antibodies

Anti-EGFR antibodies were obtained by directly administering an EGFR-expressing cell line (A431) with an adjuvant to stimulate the immune response, to a VELOCIMMUNE® mouse comprising DNA encoding human immunoglobulin heavy and a universal light chain variable regions. That is, the antibodies produced in this mouse have different heavy chain variable regions but essentially identical light chain variable domains.

The antibody immune response was monitored by an EGFR-specific immunoassay. When a desired immune response was achieved, Anti-EGFR antibodies were isolated directly from antigen-positive B cells without fusion to myeloma cells, as described in U.S. Pat. No. 7,582,298.

Table 1 sets forth the amino acid sequence identifiers of the heavy and light chain variable regions and CDRs of selected anti-EGFR antibodies of the invention. The corresponding nucleic acid sequence identifiers are set forth in Table 2.

TABLE 1

Amino Acid Sequence Identifiers for Parental EGFR Monoclonal Antibodies (mAb)

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| mAb12999P2 | 2 | 4 | 6 | 8 | 16 | 18 | GAS | 22 |
| mAb13008P2 | 30 | 32 | 34 | 36 | 16 | 18 | GAS | 22 |
| mAb35193P2 | 40 | 42 | 44 | 46 | 16 | 18 | GAS | 22 |
| mAb13006P2 | 50 | 52 | 54 | 56 | 16 | 18 | GAS | 22 |

TABLE 2

Nucleic Acid Sequence Identifiers for Parental EGFR Monoclonal Antibodies (mAb)

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| mAb12999P2 | 1 | 3 | 5 | 7 | 15 | 17 | ggggcaagt | 21 |
| mAb13008P2 | 29 | 31 | 33 | 35 | 15 | 17 | ggggcaagt | 21 |
| mAb35193P2 | 39 | 41 | 43 | 45 | 15 | 17 | ggggcaagt | 21 |
| mAb13006P2 | 49 | 51 | 53 | 55 | 15 | 17 | ggggcaagt | 21 |

Generation of Anti-CD28 Antibodies

Anti-CD28 antibodies were obtained by immunizing a VELOCIMMUNE® mouse (i.e., an engineered mouse comprising DNA encoding human Immunoglobulin heavy and universal light chain variable regions) with human CD28 protein fused to the Fc portion of mouse IgG2a, or with cells expressing CD28 or with DNA encoding CD28.

The antibody immune response was monitored by a CD28-specific immunoassay. When a desired immune response was achieved, anti-CD28 antibodies were isolated directly from antigen-positive B cells, as described in U.S. Pat. No. 7,582,298.

Table 3 sets forth the amino acid sequence identifiers of the heavy and light chain variable regions and CDRs of selected anti-CD28 antibodies of the invention. The corresponding nucleic acid sequence identifiers are set forth in Table 4.

Certain biological properties of the exemplary anti-CD28 antibodies generated in accordance with the methods of this Example are described in detail in the Examples set forth below.

TABLE 3

Amino Acid Sequence Identifiers for Parental CD28 Monoclonal Antibodies (mAb)

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| mAb14226 | 10 | 12 | 6 | 14 | 16 | 18 | GAS | 22 |
| mAb14193 | 59 | 60 | 61 | 62 | 16 | 18 | GAS | 22 |
| mAb14216 | 63 | 64 | 65 | 66 | 16 | 18 | GAS | 22 |

TABLE 4

Nucleic Acid Sequence Identifiers for Parental CD28 Antibodies

| Antibody Designation | SEQ ID NOS: | | | | | | | |
|---|---|---|---|---|---|---|---|---|
| | HCVR | HCDR1 | HCDR2 | HCDR3 | LCVR | LCDR1 | LCDR2 | LCDR3 |
| mAb14226 | 9 | 11 | 5 | 13 | 15 | 17 | ggggcaagt | 21 |
| mAb14193 | | | | | 15 | 17 | ggggcaagt | 21 |
| mAb14216 | | | | | 15 | 17 | ggggcaagt | 21 |

Generation of Bispecific Antibodies (bsAbs) that Bind AD28 and EGFR

Bispecific antibodies comprising an anti-EGFR-specific binding domain and an anti-.D28-specific binding domain were constructed using standard methodologies, wherein the anti-EGFR antigen binding domain and the anti-D28 antigen binding domain each comprise different, distinct HCVRs paired with a common LCVR. In some instances the bispecific antibodies were constructed utilizing a heavy chain from an anti-CD28 antibody, a heavy chain from an anti-EGFR antibody and a common light chain comprising the components, amino acid and nucleic acid sequences encoding the antibodies as shown below in Tables 5, 6, 7 and 8. Additional bispecific antibodies that bind to EGFR and PD28 may be prepared using the parental monoclonal antibodies having the designations shown in Tables 9A, 9B and 9C.

TABLE 5

Summary of Antibody Designations for HCVR Arms of Anti-EGFR x Anti-CD28 Bispecific Antibodies

| Bispecific Antibody Designation | Anti-EGFR Antigen-Binding Domain (Parental Antibody Designation) | Anti-CD28 Antigen-Binding Domain (Parental Antibody Designation) |
|---|---|---|
| bsAb7075 (Also referred to as REGN7075 or H4sH24623D) | mAb12999P2 | mAb14226 |
| bsAb6321 (Also referred to as REGN6321) | mAb13008P2 | mAb14226 |
| bsAb6322 (Also referred to as REGN6322) | mAb35193P2 | mAb14226 |
| bsAb6323 (Also referred to as REGN6323) | mAb13006P2 | mAb14226 |

TABLE 6

Amino Acid Sequences of Anti-EGFR × Anti-CD28 Bispecific Antibodies

| Bispecific Antibody Designation | Anti-EGFR Antigen-Binding Domain | | | | Anti-CD28 Antigen-Binding Domain | | | | Common Light Chain Variable Region | | | |
|---|---|---|---|---|---|---|---|---|---|---|---|---|
| | HCVR | HCDR1 | HCDR2 | HCDR3 | HCVR | HCDR1 | HCDR2 | HCDR3 | LCVR | LCDR1 | LCDR2 | LCDR3 |
| bsAb7075 | 2 | 4 | 6 | 8 | 10 | 12 | 6 | 14 | 16 | 18 | GAS | 22 |
| bsAb6321 | 30 | 32 | 34 | 36 | 10 | 12 | 6 | 14 | 16 | 18 | GAS | 22 |
| bsAb6322 | 40 | 42 | 44 | 46 | 10 | 12 | 6 | 14 | 16 | 18 | GAS | 22 |
| bsAb6323 | 50 | 52 | 54 | 56 | 10 | 12 | 6 | 14 | 16 | 18 | GAS | 22 |

TABLE 7

Nucleic Acid Sequences Encoding Anti-EGFR × Anti-CD28 Bispecific Antibodies

| Bispecific Designation Antibody | Anti-EGFR Antigen-Binding Domain | | | | Anti-CD28 Antigen-Binding Domain | | | | Common Light Chain Variable Region | | | |
|---|---|---|---|---|---|---|---|---|---|---|---|---|
| | HCVR | HCDR1 | HCDR2 | HCDR3 | HCVR | HCDR1 | HCDR2 | HCDR3 | LCVR | LCDR1 | LCDR2 | LCDR3 |
| bsAb7075 | 1 | 3 | 5 | 7 | 9 | 11 | 5 | 13 | 15 | 17 | ggggcaagt | 21 |
| bsAb6321 | 29 | 31 | 33 | 35 | 9 | 11 | 5 | 13 | 15 | 17 | ggggcaagt | 21 |
| bsAb6322 | 39 | 41 | 43 | 45 | 9 | 11 | 5 | 13 | 15 | 17 | ggggcaagt | 21 |
| bsAb6323 | 49 | 51 | 53 | 55 | 9 | 11 | 5 | 13 | 15 | 17 | ggggcaagt | 21 |

TABLE 8

Amino acid and nucleotide sequences for full length immunoglobulin chains of bispecific antibodies bsAb7075, bsAb6321, bsAb6322 and bsAb6323

| Bispecific Antibody Designation | HC (EGFR) | | HC (CD28) | | LC (EGFR & CD28) | |
|---|---|---|---|---|---|---|
| | D | P | D | P | D | P |
| bsAb7075 | 23 | 24 | 25 | 26 | 27 | 28 |
| bsAb6321 | 37 | 38 | 25 | 26 | 27 | 28 |
| bsAb6322 | 47 | 48 | 25 | 26 | 27 | 28 |
| bsAb6323 | 57 | 58 | 25 | 26 | 27 | 28 |

D = Nucleotide sequence of DNA encoding indicated sequence

P = amino acid of polypeptide for the indicated sequence

Numbers refer to SEQ ID NOs for the indicated sequence

HC is the full length heavy chain for the indicated antibody

LC is the full length light chain for the indicated antibody

Additional bispecific antibodies comprising one HCVR from a parental EGFR antibody and the other HCVR arm from a parental CD28 antibody may be made using the techniques described herein. The parental EGFR antibodies used to generate these additional anti-EGFR× anti-CD28 bispecific antibodies have HCVR sequences described in WO2014/004427. The CD28 parental antibodies used to generate these additional anti-EGFR× anti-CD28 bispecific antibodies have the amino acid sequences described above in Table 3. These anti-EGFR and anti-CD28 binding domains (pairings) are shown below in Tables 9A, 9B and 9C.

TABLE 9A

Summary of Parental Antibody Designations for HCVR Arms of Anti-EGFR x Anti-CD28 Additional Bispecific Antibodies

| Anti-EGFR Antigen-Binding Domain (Parental Antibody Designation and Sequences found in WO2014/004427) | Anti-CD28 Antigen-Binding Domain (Parental Antibody Designation and Sequences found herein in Table 3) |
| --- | --- |
| mAb085N | mAb14226 |
| mAb086N | mAb14226 |
| mAb136P | mAb14226 |
| mAb141P | mAb14226 |
| mAb142P | mAb14226 |
| mAb143P | mAb14226 |
| mAb144P | mAb14226 |
| mAb145P | mAb14226 |
| mAb147P | mAb14226 |
| mAb151P | mAb14226 |
| mAb153P | mAb14226 |
| mAb155P | mAb14226 |
| mAb157P | mAb14226 |
| mAb158P | mAb14226 |
| mAb159P | mAb14226 |
| mAb161P | mAb14226 |
| mAb163P | mAb14226 |
| mAb169P | mAb14226 |
| mAb171P | mAb14226 |

TABLE 9B

Summary of Parental Antibody Designations for HCVR Arms of Anti-EGFR x Anti-CD28 Additional Bispecific Antibodies

| Anti-EGFR Antigen-Binding Domain (Parental Antibody Designation and Sequences found in WO2014/004427) | Anti-CD28 Antigen-Binding Domain (Parental Antibody Designation and Sequences found herein in Table 3) |
| --- | --- |
| mAb085N | mAb14193 |
| mAb086N | mAb14193 |
| mAb136P | mAb14193 |
| mAb141P | mAb14193 |
| mAb142P | mAb14193 |
| mAb143P | mAb14193 |
| mAb144P | mAb14193 |
| mAb145P | mAb14193 |
| mAb147P | mAb14193 |
| mAb151P | mAb14193 |
| mAb153P | mAb14193 |
| mAb155P | mAb14193 |
| mAb157P | mAb14193 |
| mAb158P | mAb14193 |
| mAb159P | mAb14193 |
| mAb161P | mAb14193 |
| mAb163P | mAb14193 |
| mAb169P | mAb14193 |
| mAb171P | mAb14226 |

TABLE 9C

Summary of Parental Antibody Designations for HCVR Arms of Anti-EGFR x Anti-CD28 Additional Bispecific Antibodies

| Anti-EGFR Antigen-Binding Domain (Parental Antibody Designation and Sequences found in WO2014/004427) | Anti-CD28 Antigen-Binding Domain (Parental Antibody Designation and Sequences found herein in Table 3) |
| --- | --- |
| mAb085N | mAb14216 |
| mAb086N | mAb14216 |
| mAb136P | mAb14216 |
| mAb141P | mAb14216 |
| mAb142P | mAb14216 |
| mAb143P | mAb14216 |
| mAb144P | mAb14216 |
| mAb145P | mAb14216 |
| mAb147P | mAb14216 |
| mAb151P | mAb14216 |
| mAb153P | mAb14216 |
| mAb155P | mAb14216 |
| mAb157P | mAb14216 |
| mAb158P | mAb14216 |
| mAb159P | mAb14216 |
| mAb161P | mAb14216 |
| mAb163P | mAb14216 |
| mAb169P | mAb14216 |
| mAb171P | mAb14216 |

The bispecific antibodies described in the following examples consist of binding arms known to bind to human soluble heterodimeric hCD28 protein; and human EGFR (see Biacore binding data below). Exemplified bispecific antibodies were manufactured having a modified (chimeric) IgG4 Fc domain as set forth in US Patent Application Publication No. US20140243504A1, published on Aug. 28, 2014.

The bispecific antibodies created in accordance with the present Example comprise two separate antigen-binding domains (i.e., binding arms). The first antigen-binding domain comprises a heavy chain variable region derived from an anti-CD28 antibody ("CD28-VH"), and the second antigen-binding domain comprises a heavy chain variable region derived from an anti-EGFR antibody ("EGFR-VH"). Both the anti-EGFR and the anti-CD28 share a common light chain. The CD28-VH/EGFR-VH pairing creates antigen-binding domains that specifically recognize CD28 on T cells and EGFR on tumor cells.

Characterization of Bispecific Antibodies that Bind CD28 and EGFR

SPR Kinetics Method: Kinetics binding parameters were determined via surface plasmon resonance (SPR) using a T-200 instrument and CM5 sensors (GE Healthcare). Double-referenced sensorgrams were globally fit to a 1:1 binding model using Scrubber (BioLogics Software). The dissociation rate constant (kd) was determined by fitting the change in the binding response during the dissociation phase, and the association rate constant (ka) was determined by fitting analyte binding at different concentrations. The $K_D$ was calculated from the ratio of the kd and ka. The dissociative half-life (t½) was calculated as ln2/kd and converted to minutes.

EGFR Specifics Method: An anti-hFc monoclonal Ab (REGN2567) was coupled to a CM5 sensor surface using traditional EDC/NHS coupling chemistry. 200-250 RUs of EGFRxCD28 Ab were captured on this surface. A six-point, three-fold dilution series of hEGFR.mmH starting at 30 nM was injected over this surface at a flow rate of 50 uL/min for 5 minutes. Surface was regenerated with a 10 second pulse of 20 mM H3PO4. Dissociation was measured for 10 minutes. Sensorgrams were processed and fit as described above.

CD28 Capture Method Specifics: An anti-mFc polyclonal Ab (GE) was coupled to a CM5 sensor surface using traditional EDC/NHS coupling chemistry. ~30RUs of hCD28.mFc were captured on this surface. A six point, three-fold dilution series of EGFRxCD28 Ab starting at 90 nM was injected over this surface at a flow rate of 50 uL/min for 4 minutes. Dissociation was measured for 5 minutes. Surface was regenerated with a 40 second injection of 10 mM glycine, pH 1.5. Sensorgrams were processed and fit as described above.

Biacore analysis showed that EGFRxCD28 bound hEGFR with a $K_D$ of ~9.3E-10 and hCD28 with a $K_D$ of ~5.2E-08 (Tables 10 and 11).

TABLE 10

Biacore Kinetics of Binding to EGFR

| AbPID | mAB Capture (RU) | 30 nM hEGFR.mmh Bind (RU) | Ka (1/Ms) | Kd (1/s) | $K_D$ (M) | t½ (min) |
|---|---|---|---|---|---|---|
| Biacore 37° C. Binding to Human EGFR-mmh | | | | | | |
| REGN7075 | 245.6 ± 0.7 | 72.67 | 4.41E+05 | 4.12E−04 | 9.33E−10 | 4.24 |
| Biacore 25° C. Binding to Human EGFR-mmh | | | | | | |
| REGN7075 | 209.6 ± 0.8 | 55.45 | 1.54E+05 | 4.33E−04 | 2.80E−09 | 26.69 |

TABLE 11

Biacore Kinetics of Binding to CD28

| AbPID | hCD28.mFc Capture (RU) | 90 nM mAb Bind (RU) | Ka (1/Ms) | Kd (1/s) | $K_D$ (M) | t½ (min) |
|---|---|---|---|---|---|---|
| Biacore 37° C. Binding to Human CD28-mFc | | | | | | |
| REGN7075 | 39.8 ± 0.2 | 25.0 | 2.54E+05 | 1.31E−02 | 5.17E−08 | 0.9 |
| Biacore 25° C. Binding to Human CD28-mFc | | | | | | |
| REGN7075 | 32.6 ± 0.2 | 27.1 | 2.94E+05 | 3.14E−03 | 1.07E−08 | 3.7 |

Next, using co-cultures of human T-cells containing peripheral blood mononuclear cells (PBMCs) and PEO-1, the ability of EGFR×CD28 to induce cellular cytotoxicity and T-cell activation was tested. Human peripheral blood mononuclear cells (PBMCs) were isolated from a healthy donor leukocyte pack. PBMC isolation was accomplished by density gradient centrifugation using 50 mL SepMate™ tubes following the manufacturer's recommended protocol. Briefly, 15 mL of FicollPaque PLUS was layered into 50 mL SepMate tubes, followed by addition of 30 mL of leukocytes diluted 1:2 with D-PBS. Subsequent steps were followed according to SepMate manufacturer's protocol. CD3+ T-cells were subsequently isolated from PBMC's using an EasySep Human T-Cell Isolation Kit from StemCell Technologies and following manufacturer's recommended instructions. Isolated CD3+ T-cells were frozen in FBS containing 10% DMSO at a concentration of $50 \times 10^6$ cells per vial.

Figure 1A:
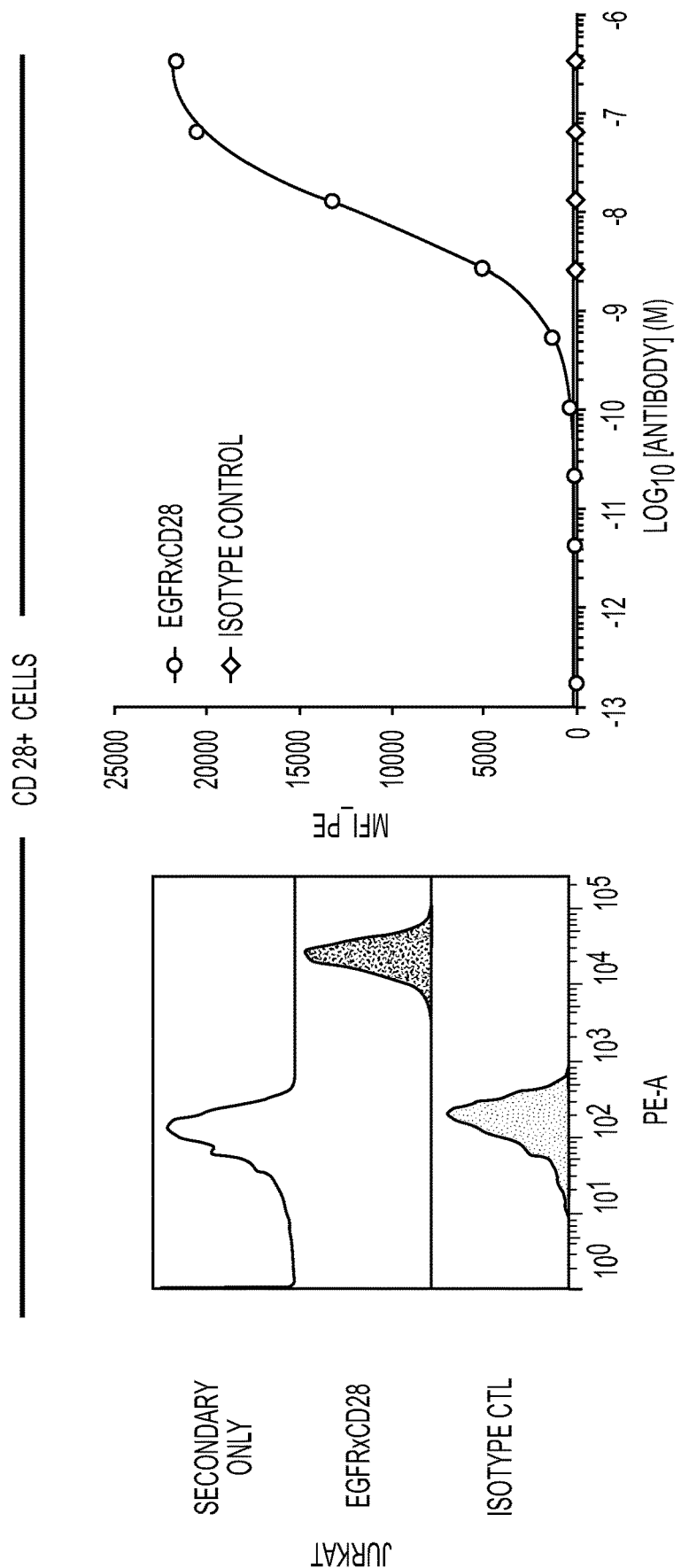
FIGS. 1A, 1B, 1C, 1D, and 1E show that, in cancer cell lines with endogenous TSA, EGFR×CD28 bispecific antibody (REGN7075) potentiates T-cell activation in the presence of TCR stimulation by TSA×CD3 (MUC16×CD3).
Figure 1B:
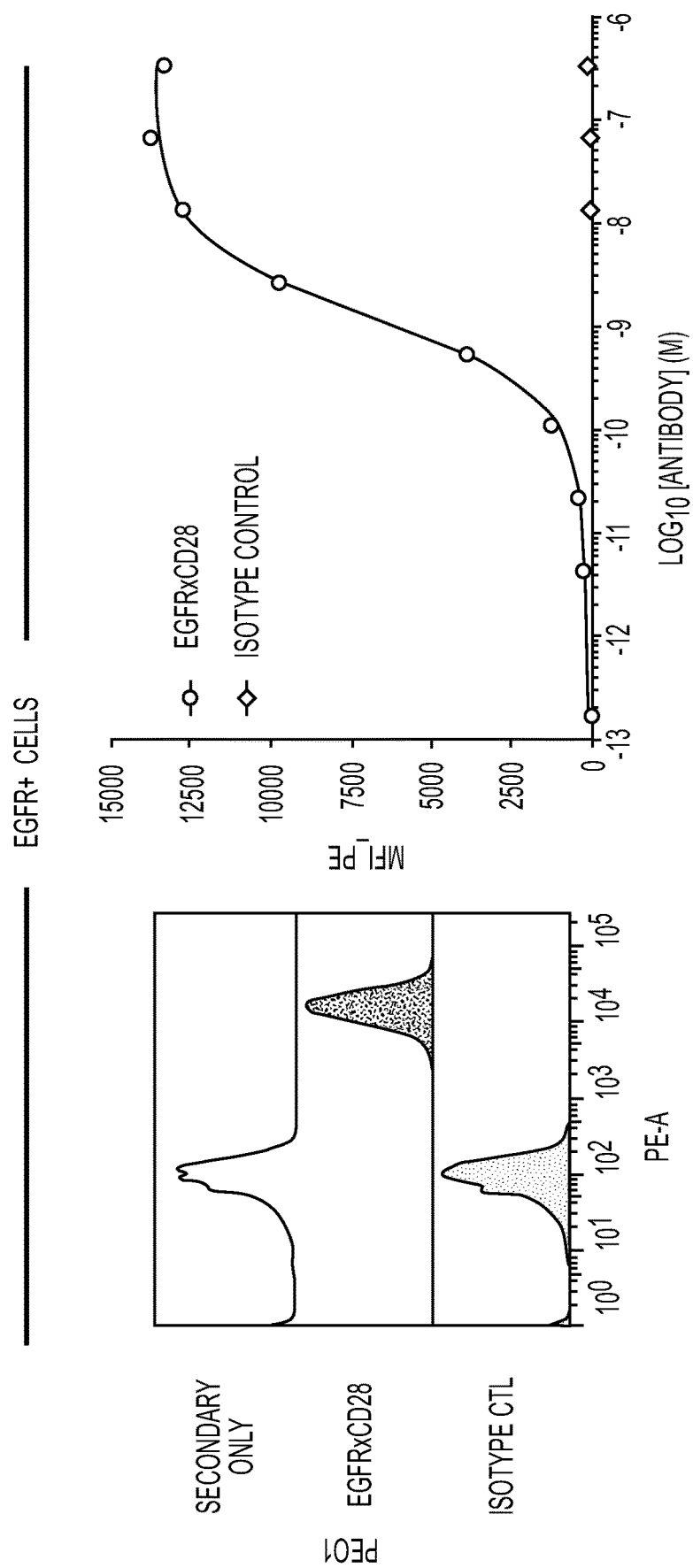
Figure 1D:
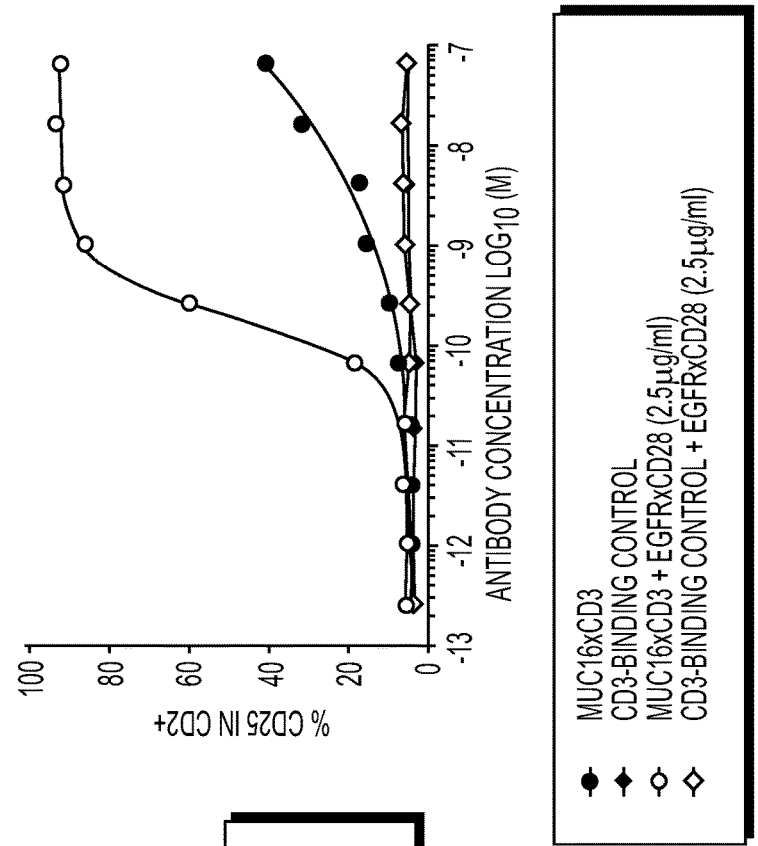
Figure 1C:
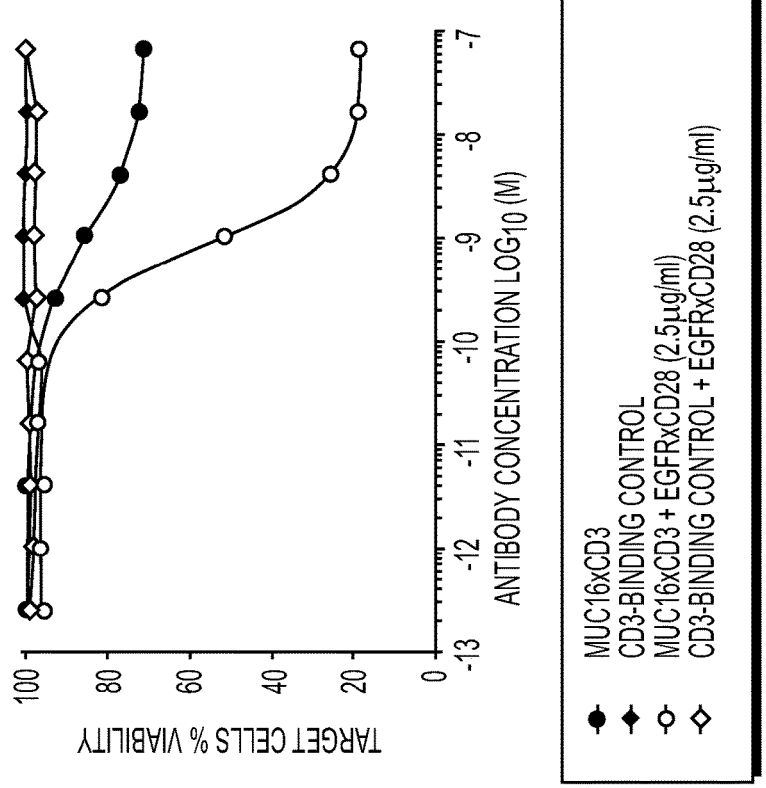
Figure 1E:
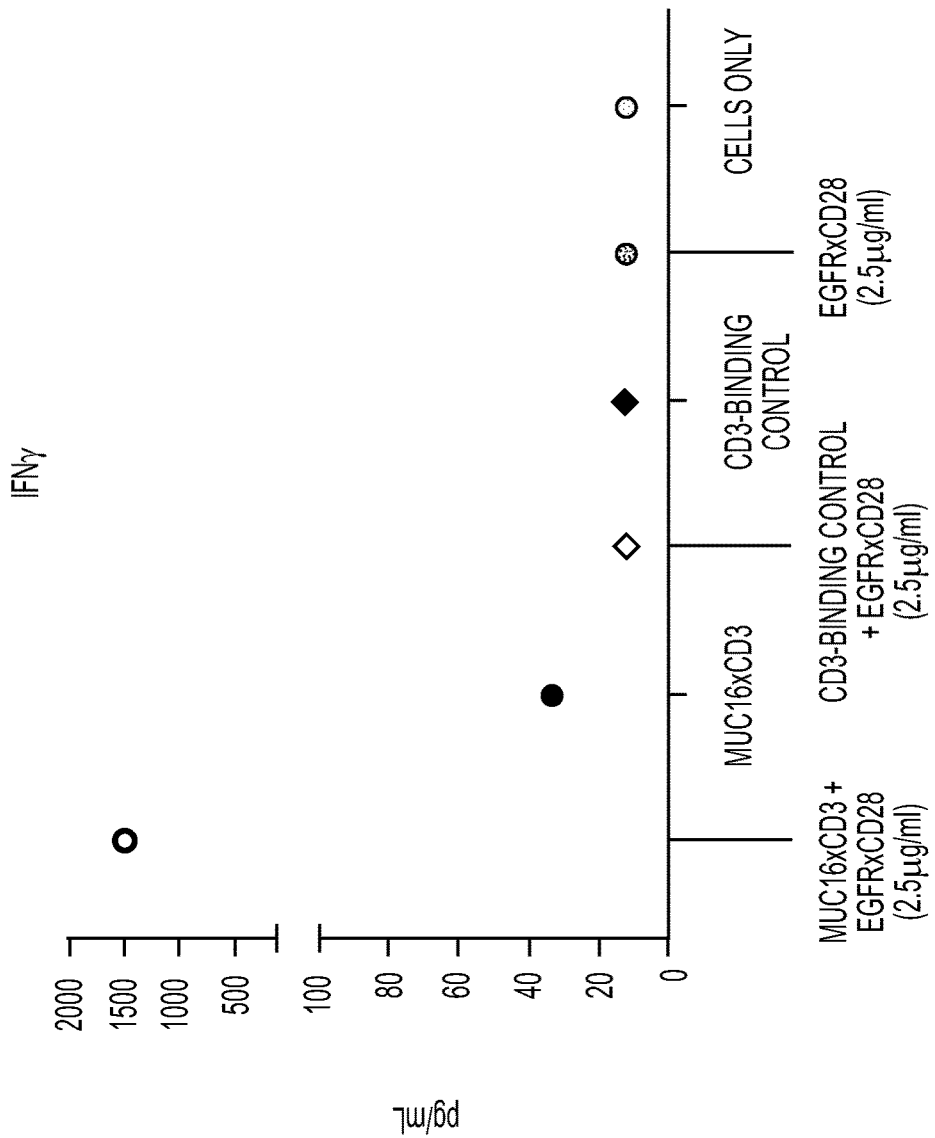

EGFR×CD28 significantly increased the ability of MUC16×CD3 (data not shown) to induce T-cell killing of tumor cells, from 18.8% to 71.5% (FIG. 1C). Consistent with this enhancement of T-cell cytotoxicity, EGFR×CD28 also boosted the T-cell activation as assessed by CD25-expression and IFNγ cytokine release (FIGS. 1D and 1E). Notably, EGFR×CD28 in the presence of non-targeted CD3 binding control (absence of "signal 1") had no effect on T-cell cytotoxicity or activation (FIGS. 1C-1E).

Example 2: Over-Expression of a Natural CD28 Ligand on Tumor Cells Synergizes with PD-1 mAb Treatment to Induce CD8 T Cell-Dependent Durable Anti-Tumor Immunity In Vivo To determine if CD28 engagement by its natural ligand(s) could potentiate the anti-tumor efficacy of PD-1 mAb in vivo, MC38 tumor cells were engineered to over-express CD86, one of the co-stimulatory ligands for CD28. Specifically, to generate tumor cell lines engineered to express co-stimulatory ligands, the pLVX lentiviral plasmid with EF1 a promoter encoding mouse CD86 or empty vector and a puromycin resistance gene (pLVX.EF1a.CD86-puro and pLVX.EF1 a.EV-puro, respectively) was used to transfect HEK293T cells, facilitating the production of viral particles, which were subsequently used to infect MC38 (National Cancer Institute, Laboratory of Tumor Immunology & Biology). Engineered cell lines expressing CD86 were isolated by fluorescence-activated cell sorting (FACS). Cells were maintained under conditions recommended by ATCC in the presence of 0.5 µg/ml Puromycin. Resulting cell lines were designated MC38/CD86 and MC38/EV.

Figure 2D:
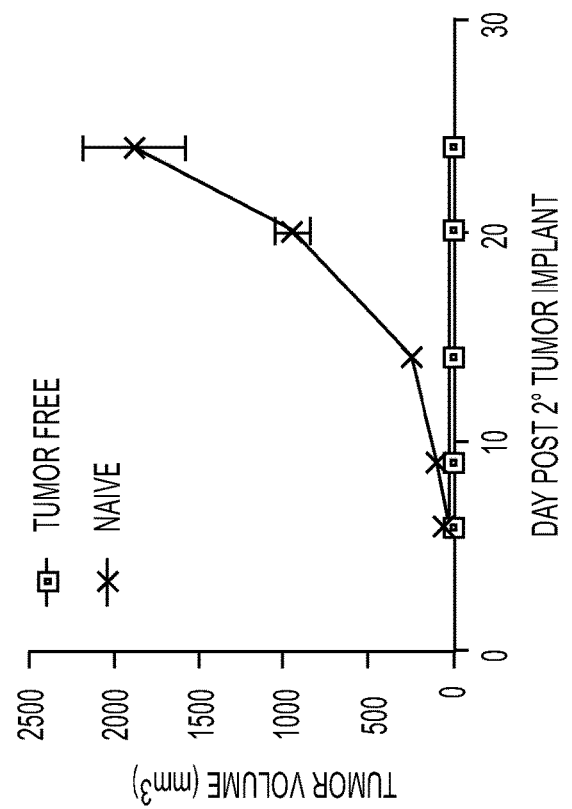
Figure 2C:
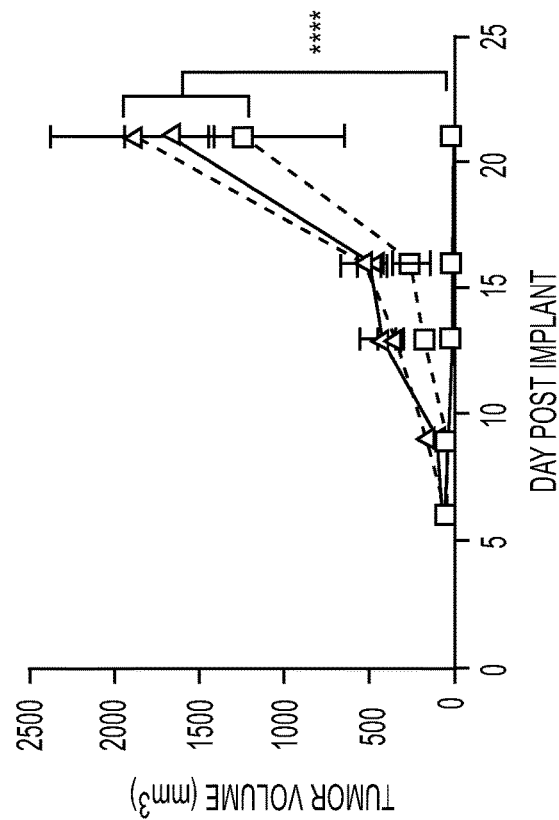

Combination of MC38/CD86 cells and anti-PD-1 mAb treatment significantly inhibited tumor growth (FIG. 2A), resulting in complete tumor regression associated with robust survival benefit (FIG. 2B) when compared with a negative control MC38 cells transfected with an empty vector control (MC38/EV). Depletion of CD8+ T-cells during the course of treatment completely abrogated the anti-tumor efficacy elicited by combining anti-PD-1 mAb therapy with MC38/CD86 cells demonstrating a dependence on CD8+ T-cells (FIG. 2C). Of note, tumor free mice that were initially implanted with MC38/CD86 cells and treated with anti-PD-1 mAb rejected a second MC38 parental tumor that was implanted more than 60 days after the implantation of the primary tumor, indicating the presence of a T-cell memory response (FIG. 2D). Consequently, these data demonstrate that the synergistic effect of constitutive expression of a CD28 ligand and anti-PD-1 therapy can result in a durable CD8-dependent anti-tumor immunity in vivo.

Figure 3A:
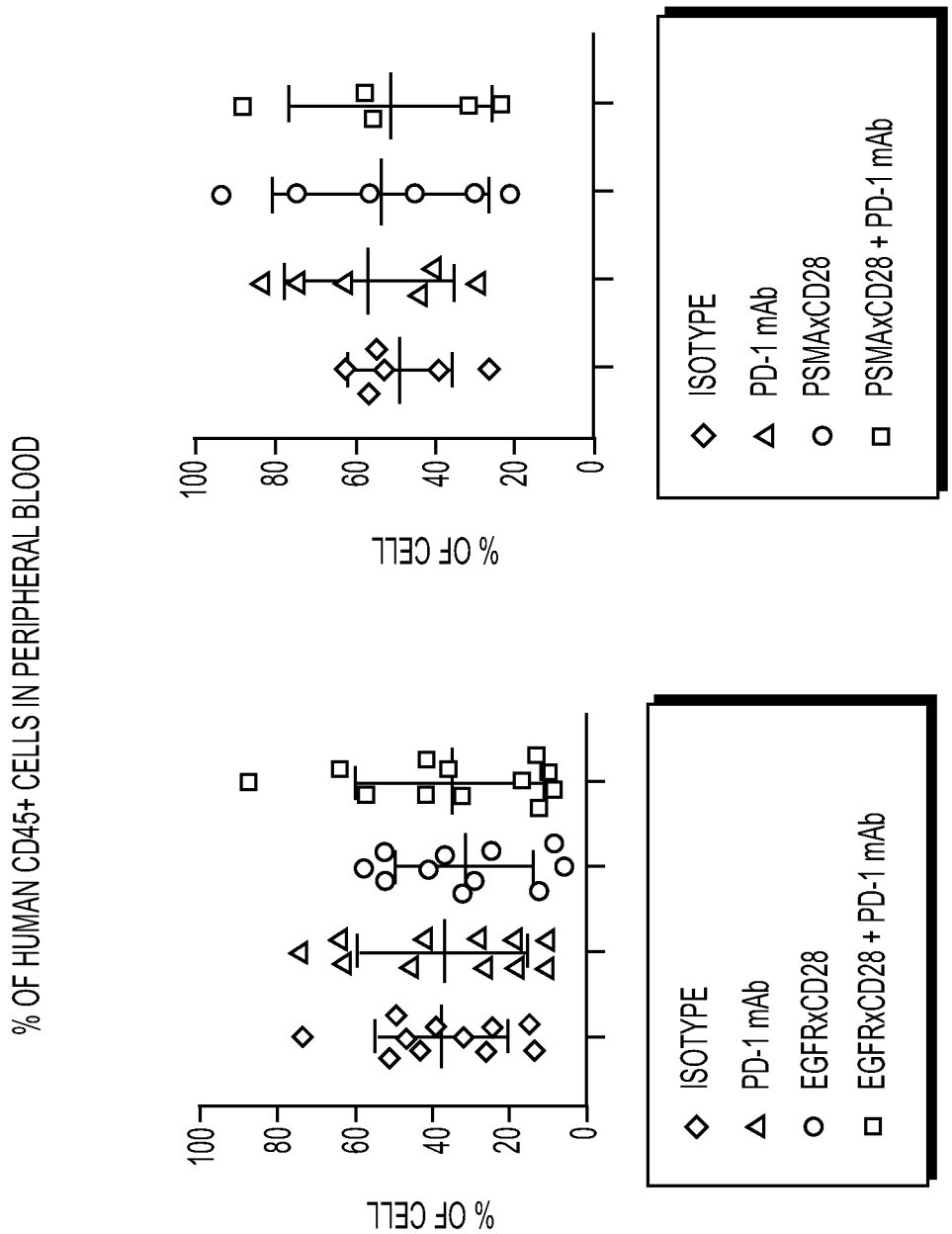
FIGS. 3A and 3B show A431 Human xenograft tumor model. Data corresponds with FIGS. 4 and 5.

Example 3: Administration of EGFR×CD28 Antibodies in Combination with Anti-PD-1 Antibodies Synergistically Controls and Eradicates Mouse Human Tumor Xenografts, $V_H$ Engrafted with Human CD34+ Stem Cells The effectiveness of EGFR×CD28 bispecific antibody in combination with PD-1 blocking Ab (REGN2810 (cemiplimab), E. Burova et al., Characterization of the Anti-PD-1 Antibody REGN2810 and Its Antitumor Activity in Human PD-1 Knock-In Mice. *Mol Cancer Ther* 16, 861-870 (2017)) was tested using human tumor xenograft model. The engraftment of human immune cell population was validated by FACS (FIG. 3A). A431 epidermoid carcinoma tumor cells (obtained from ATCC) were implanted subcutaneously in SIRPA$^{h/h}$ TPO$^{h/m}$ Rag2$^{-/-}$ Il2rg$^{-/-}$ that were engrafted with fetal liver CD34+ cells. Mice were segregated into 4 groups based on fetal liver donor, human immune cell engraftment frequency and sex. Mice were dosed by intra-peritoneal injection 2× per week starting on the day of implant (day 0) with isotype control, 5 mg/kg of EGFR×CD28, 10 mg/kg of PD-1 or combination. Antibody injection(s) were then administrated every 2-3 days through the experiment. Tumors were measured two dimensionally (length×width) and tumor volume was calculated (length× width$^2$×0.5). Mice were euthanized when the tumor reached a designated tumor end-point (tumor volume>2000 mm$^3$ or tumor ulceration).

Figure 3B:
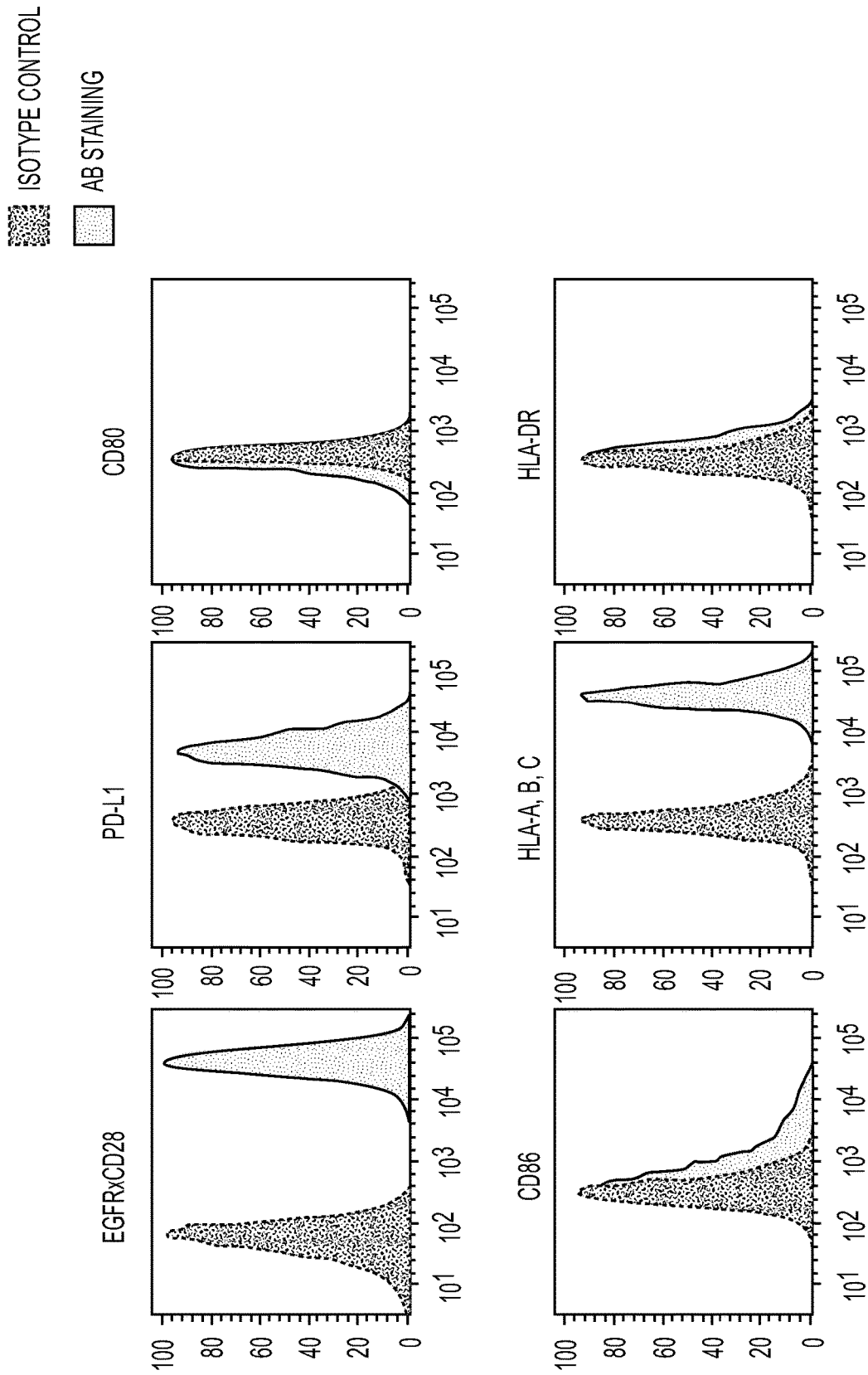

The expression of EGFR and PD-L1 on A431 tumor cells were validated by FACS (FIG. 3B). Each group was treated intra-peritoneally (IP) starting on the day of tumor challenge with:
(1) 10 mg/kg human Isotype Control No. 1+5 mg/kg human Isotype Control No. 2
(2) 10 mg/kg anti-human PD-1 (REGN2810; cemiplimab)+5 mg/kg human Isotype Control No. 2
(3) 5 mg/kg EGFR×CD28 (REGN7075)+10 mg/kg human Isotype Control No. 1 or
(4) 5 mg/kg EGFR×CD28 (REGN7075)+10 mg/kg anti-human PD-1 (REGN2810). Antibody injection(s) were then administrated 2× per week through the experiment. Tumors were measured two dimensionally (length×width) and tumor volume was calculated (length×width$^2$×0.5). Mice were euthanized when the tumor reached a designated tumor end-point (tumor volume>2000 mm$^3$ or tumor ulceration).

Isotype Control No.1 and Isotype Control No. 2 are negative control antibodies that bind Fel d1.

Figure 4:
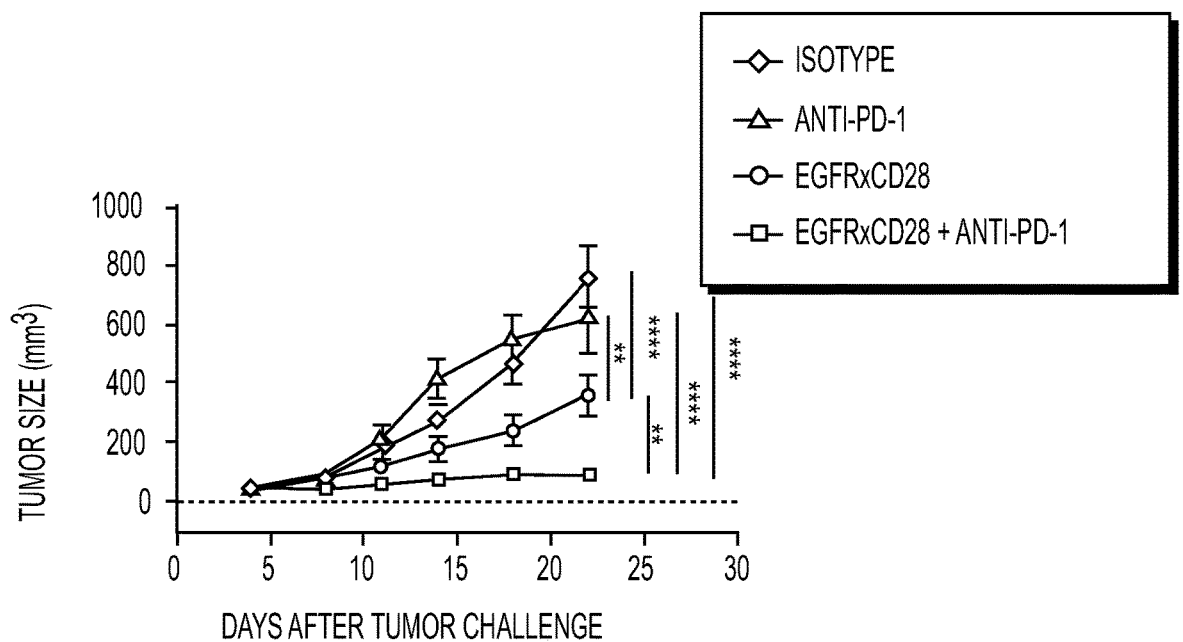
FIG. 4 and FIG. 5 show EGFR×CD28 (REGN7075) synergizes with anti-PD1 (cemiplimab) treatment to induce anti-tumor immunity in VH mice engrafted with human fetal liver CD34+ cells. Specifically, in FIGS. 4 and 5, A431 epidermoid carcinoma tumor cells (obtained from ATCC) were implanted subcutaneously in $SIRPA^{h/h}$ $TPO^{h/m}$ $Rag2^{-/-}$ $Il2rg^{-/-}$ mice that were engrafted with fetal liver CD34+ cells. Mice were segregated into indicated treatment groups based on fetal liver donor, human immune cell engraftment frequency and sex. Mice were treated intra-peritoneally (IP) starting on the day of tumor challenge and administrated every 2-3 days through the experiment. Dose for anti-PD-1 is 10 mg/kg and EGFR×CD28 or PSMA×CD28, 5 mg/kg. Data shown are average A431 tumor volumes for each treatment group ($mm^3$±SEM) plotted against days after tumor challenge. Two-way ANONA, Tukey comparison:  P<0.01, ** P<0.001. (n=10~12 mice per group).
Figure 5:
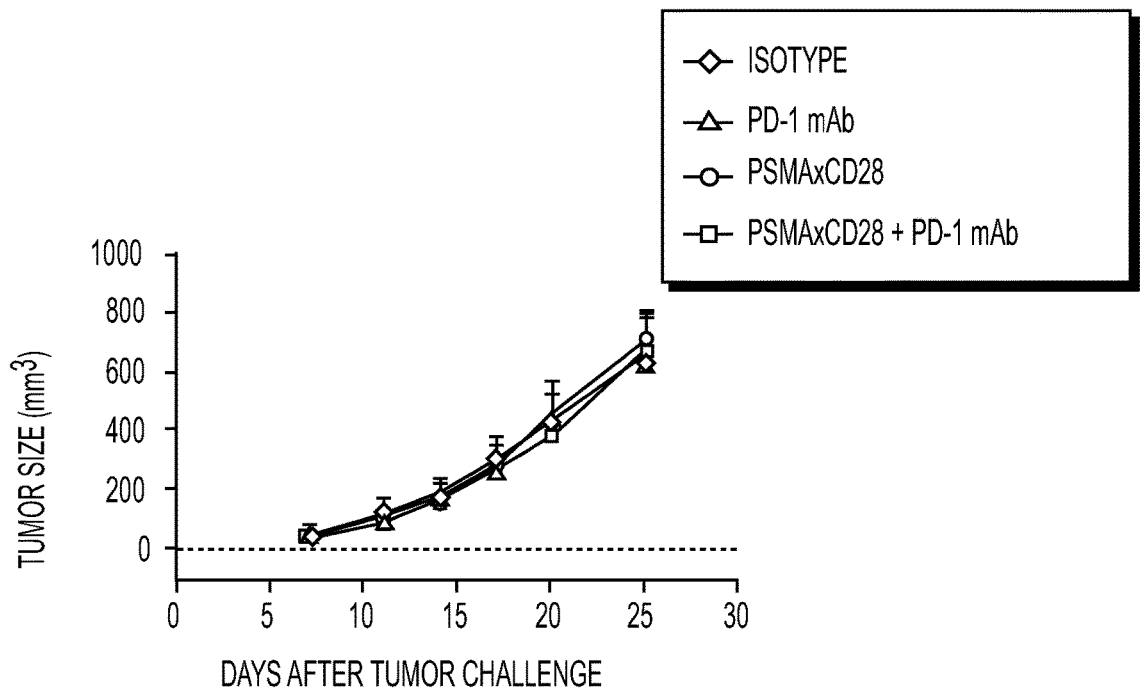
Figure 6:
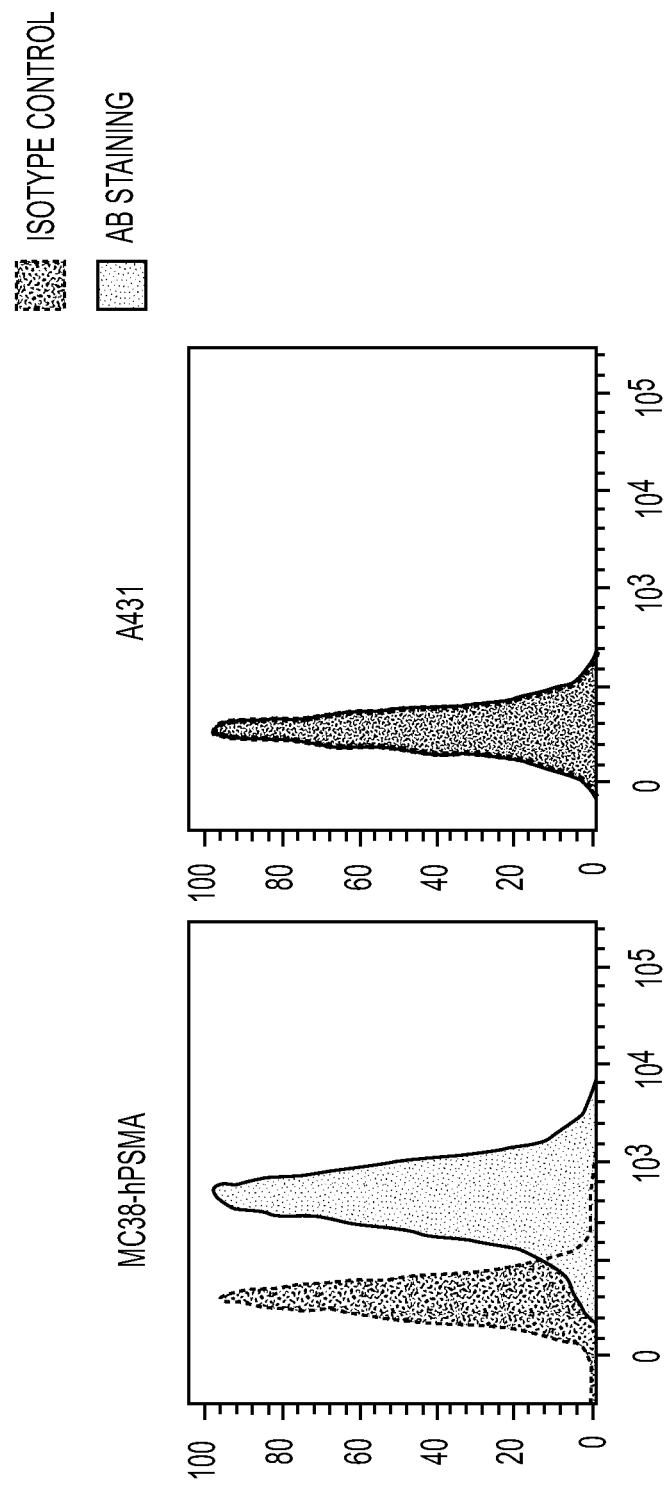
FIG. 6 shows the validation of the lack of PSMA expression on A431 tumor cells. MC38 mouse tumor cell line engineered to express human PSMA was used as positive control.

The size of the A431 tumor sizes over time in each treatment group are set forth in FIG. 4. EGFR×CD28 in combination with anti-PD-1 synergistically controlled and eradicated human tumor xenografts in humanized mice. EGFR×CD28 monotherapy was able to delay tumor growth significantly and combination with anti-PD-1 Ab further inhibited the tumor progression. When a control PSMA× CD28 Ab was used in the same treatment setting, tumor growth inhibition with or without anti-PD1 treatment was not observed (FIG. 5). A lack of PSMA expression on A431 tumor cells was validated by FACS (FIG. 6).

These data demonstrated that anti-PD1 monotherapy caused limited anti-tumor response and anti-EGFR monotherapy caused partial anti-tumoral response whereas combination therapy exhibited a strong, robust anti-tumoral immune response.

Example 4: Administration of EGFR×CD28 Antibodies as Monotherapy Controls and Eradicates Human A431 Tumor Xenografts in NSG Mice Engrafted with Human PBMC Cells A431 epidermoid carcinoma tumor cells (obtained from ATCC) were mixed with human PBMC and implanted subcutaneously in NSG mice (NOD/SCID/$\gamma_c^{null}$). Mice were treated with either a prophylactic (treatment on day 0, 3, 7) or therapeutic (day 3, 7, 10) protocol.

For the prophylactic protocol, mice were segregated into 4 treatment groups. Each group was treated intra-peritoneally (IP) with:
(1) 5 mg/kg control Ab EGRvIII×CD3 (bs17664D)
(2) 5 mg/kg EGFR×CD28 (REGN7075)
(3) 0.5 mg/kg EGFR×CD28 (REGN7075)
(4) 0.05 mg/kg EGFR×CD28 (REGN7075).

For therapeutic protocol, mice were segregated into 3 treatment group. Each group was treated with:
(1) 5 mg/kg control Ab EGRvIII×CD3 (bs17664D)
(2) 5 mg/kg EGFR×CD28 (REGN7075)
(3) 0.05 mg/kg EGFR×CD28 (REGN7075).

Tumors were measured two dimensionally (length×width) and tumor volume was calculated (length×width$^2$×0.5). Mice were euthanized when the tumor reached a designated tumor end-point (tumor volume>2000 mm$^3$ or tumor ulceration).

Figure 7A:
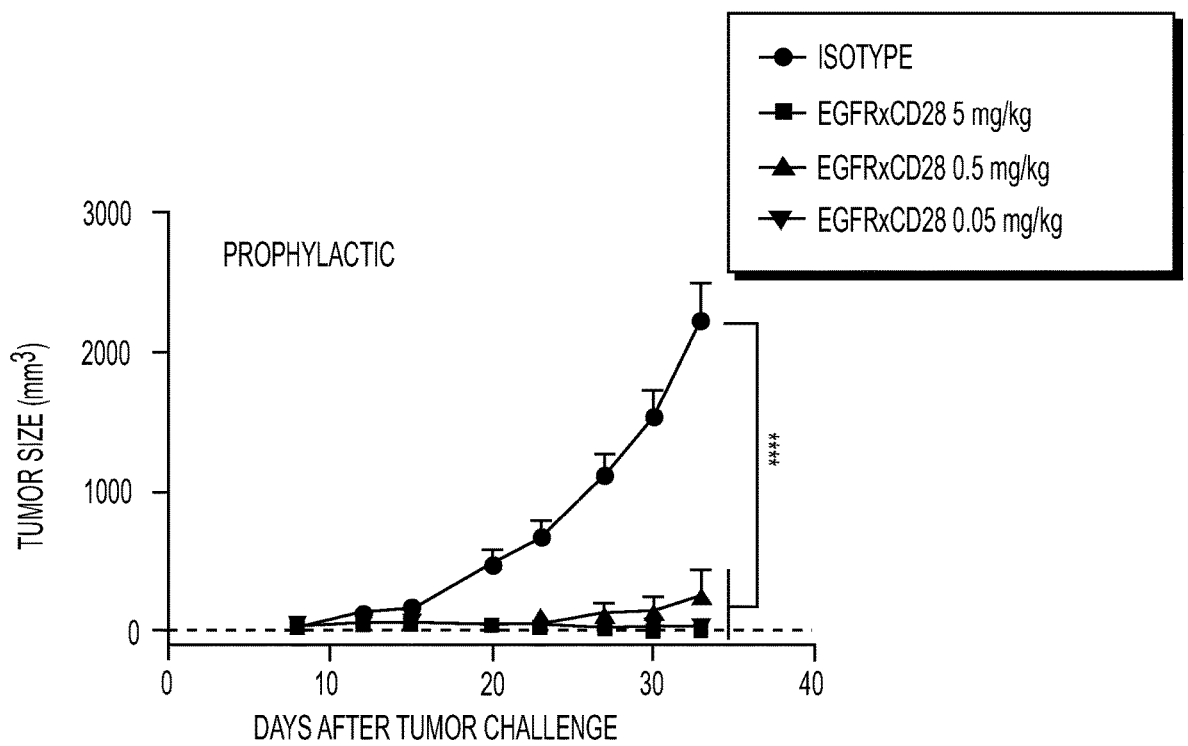
FIGS. 7A and 7B. Average A431 tumor volumes for each treatment group ($mm^3$±SEM) receiving EGFR×CD28 (REGN7075) plotted against days after tumor challenge in NSG mice either prophylactically (FIG. 7A) or therapeutically (FIG. 7B) treated. Two-way ANONA, Tukey comparison: **** P<0.0001.
Figure 7B:
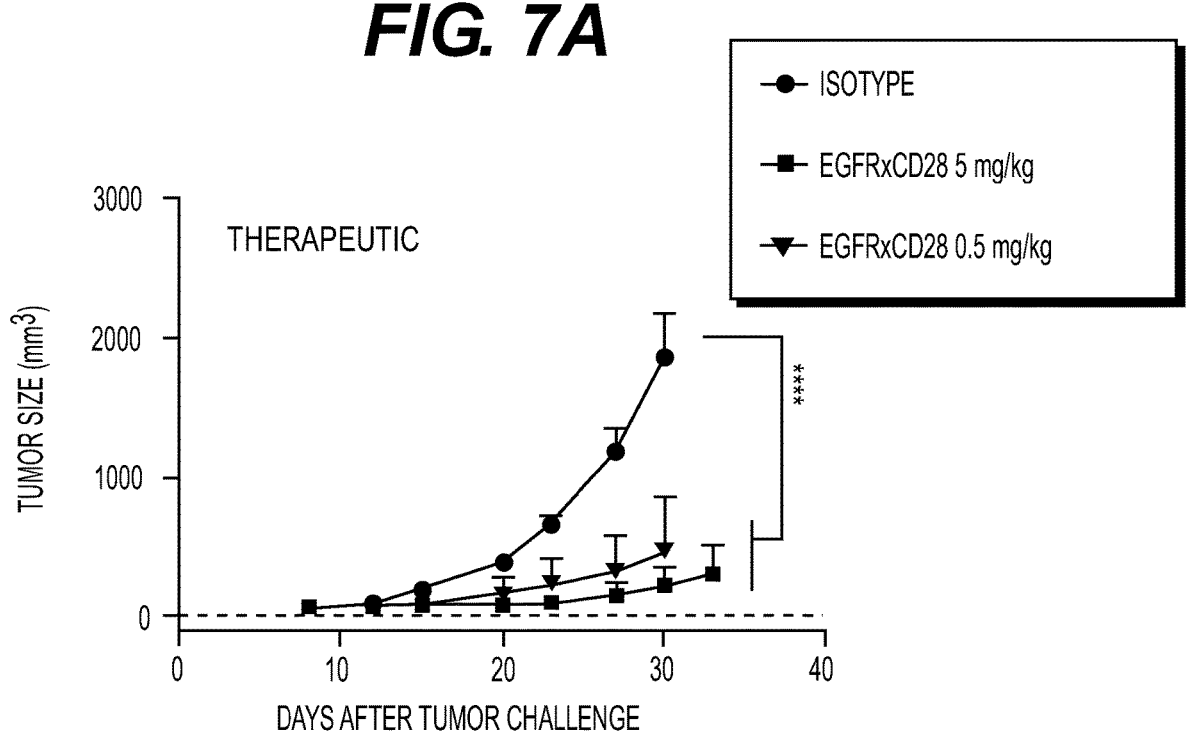

The average tumor size in mice treated in each treatment group are summarized in FIGS. 7A and 7B. These data demonstrated that in a prophylactic setting, a strong anti-tumor response is observed at all three doses tested whereas the response was less than complete in a therapeutic setting.

Example 5: Administration of EGFR×CD28 Antibodies as Monotherapy Controls and Eradicates Human A549 Tumor Xenografts in NSG Mice Engrafted with Human PBMC Cells A549 lung adenocarcinoma tumor cells (obtained from ATCC) were implanted subcutaneously in NSG mice (NOD/SCID/$\gamma_c^{null}$) on day 0. Human PBMC was engrafted on day 3 intra-peritoneally. Mice were segregated into 4 treatment groups. Each group was treated intra-peritoneally (IP) with:
(1) 10 mg/kg control Ab EGRvIII×CD3 (bs17664D)
(2) 1 mg/kg EGFR×CD28 (REGN7075)
(3) 10 mg/kg EGFR×CD28 (REGN7075).

Ab treatment was administered on day 15, 22 and 29. Tumors were measured two dimensionally (length×width) and tumor volume was calculated (length×width$^2$×0.5). Mice were euthanized when the tumor reached a designated tumor end-point (tumor volume>2000 mm$^3$ or tumor ulceration).

Figure 8:
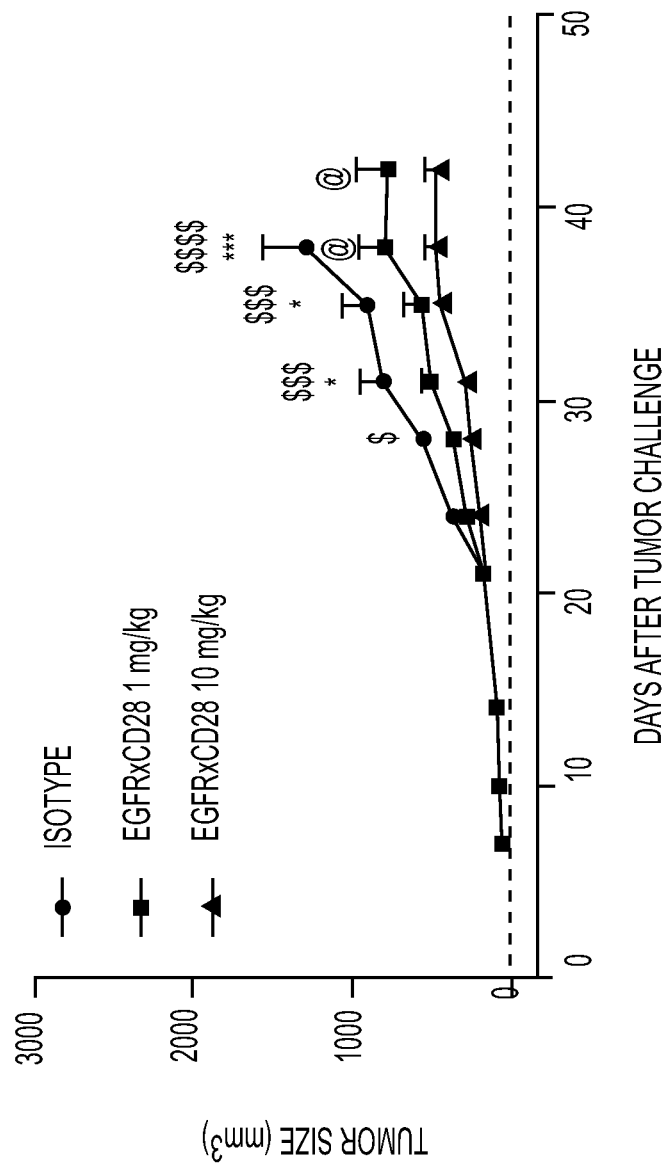
FIG. 8. Average A549 tumor volumes for each treatment group ($mm^3$±SEM) (isotype or EGFR×CD28 (REGN7075) @1 mg/kg or 10 mg/kg) plotted against days after tumor challenge in NSG mice. Two-way ANOVA, Tukey comparison: * isotype vs EGFR×CD28 1 mg/kg (P<0.05), ****: P<0.0001; $ isotype vs EGFR×CD28 10 mg/kg (P<0.05), $$$: P<0.001, $$$$: P<0.0001; @EGFR×CD28 1 mg/kg vs 10 mg/kg (P<0.05).

The average tumor sizes in mice treated in each treatment group are summarized in FIG. 8. A significant dose-dependent anti-tumor response was observed under a therapeutic setting with an established tumor.

Example 6: EGFR×CD28 Co-Stimulatory Bispecific Antibody Binds to CD28+ and EGFR+ Cells Flow cytometry analysis was utilized to determine binding of EGFR×CD28 (REGN6323) to Jurkat cells (CD28+ cells) and to PEO1 cells (EGFR+ cells). Binding of the antibody to each cell type was observed. See FIGS. 1A and 1B.

Cell lines endogenously expressing EGFR (PEO1, EGFR+) were labeled with 1 µM of Violet Cell Tracker and plated overnight at 37° C. Separately, human PBMCs (New York Blood Center) or cynomolgus monkey PBMCs (Covance, Cranford NJ) were plated in supplemented RPMI media at 1×10$^6$ cells/mL and incubated overnight at 37° C. in order to enrich for lymphocytes by depleting adherent macrophages, dendritic cells, and some monocytes. The next day, the target cells were co-incubated with adherent cell-depleted naïve human PBMC (Effector/Target cell 4:1 ratio) and a serial dilution of either TSA×CD3 or non-targeting CD3-based bispecific, alone or in combination with a fixed concentration (2.5 µg/ml) of a TSA×CD28 bispecific for 96 hours at 37° C. Post incubation, the cells were removed from the cell culture plates using an enzyme-free cell dissociation buffer and analyzed by Flow Cytometry (FACS).

For FACS analysis, cells were stained with a viability far red cell tracker (Invitrogen) and directly conjugated antibodies to CD2, CD4, CD8 and CD25 (BD). Samples were run with calibration beads for cell counting. For the assessment of specificity of killing, target cells were gated as Violet cell tracker positive populations. Percent of live target cells was calculated as follows: % viable cells=(R1/R2) *100, where R1=% live target cells in the presence of antibody, and R2=% live target cells in the absence of test antibody. T cell activation was measured by the percent of activated (CD25$^+$) T cells out of CD2$^+$/CD4$^+$ or CD2$^+$/CD8$^+$ T cells. T cell count was measured by calculating the number of live CD4$^+$ or CD8$^+$ cells per calibration bead.

The levels of cytokines accumulated in the media were analyzed using the BD cytometric Bead Array (CBA) human Th1/Th2/Th17 Cytokine kit, following the manufacturer's protocol.

Example 7: Intra-Tumoral T-Cell Cluster Analysis

To examine whether treatment has significant impact on human T-cells' activation in the A431 tumor xenograft model, intra-tumoral T-cells were profiled. CITRUS (cluster identification, characterization, and regression), a method that independently stratifies statistically significant different T cell clusters, was used to identify responding human CD8+/CD4+ T-cell clusters upon single and combination treatment.

For flow cytometry analysis of in vivo experiments, tumors were harvested, single cell suspensions were prepared, and red blood cells were lysed using ACK Lysis buffer (ThermoFisher Scientific). Live/dead cell discrimination was performed using Live/dead fixable blue dead cell staining kit (ThermoFisher Scientific). Samples were acquired on Symphony (BD Bioscience) and analyzed using Cytobank software (Cytobank, Santa Clara, CA). Analysis were performed with equal numbers of events per sample. The range in events was determined by the sample with the fewest events acquired. To cluster T cells automatically based on specific markers, CITRUS analysis from Cytobank was used.

Figure 9A:
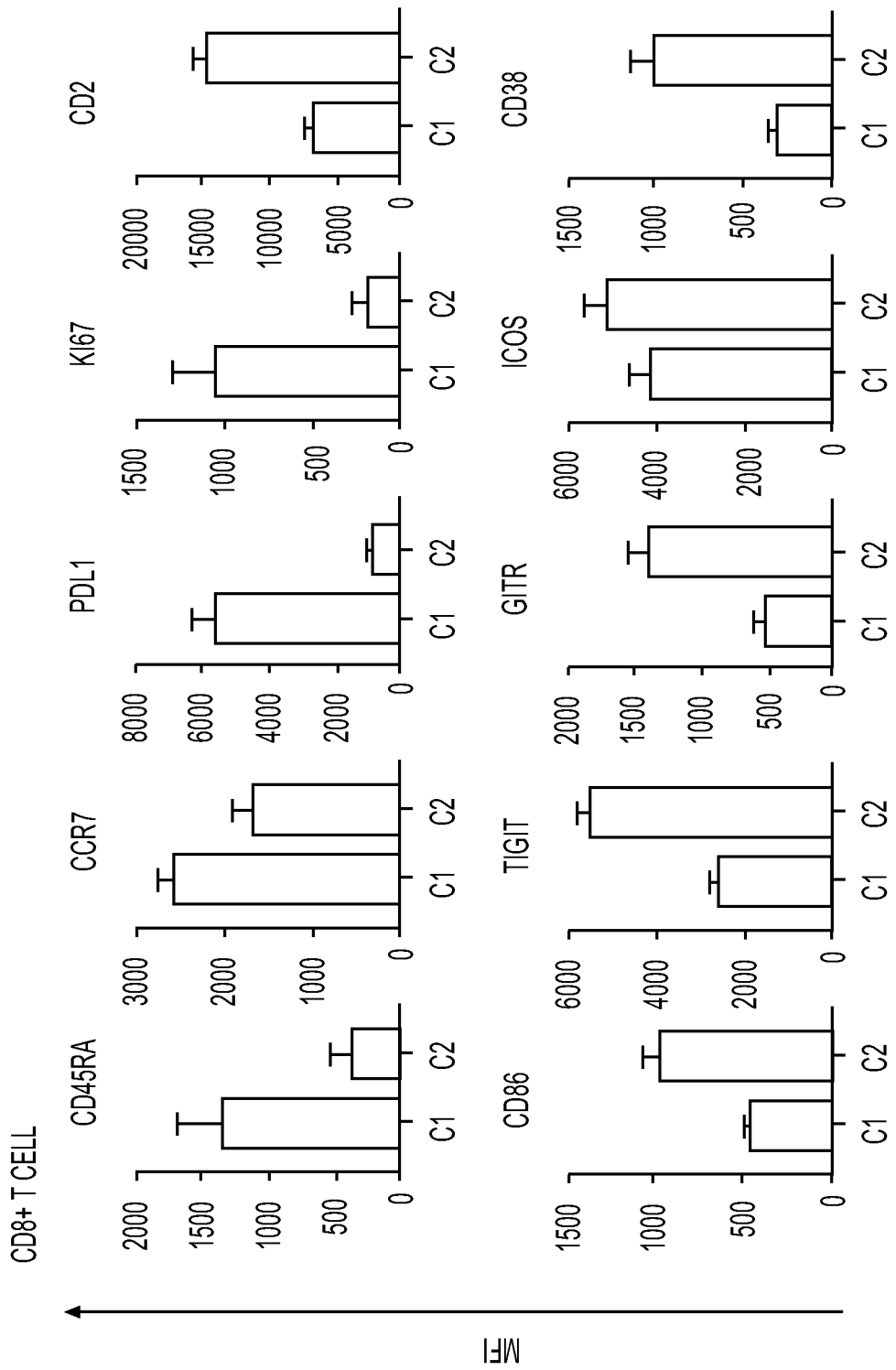
FIGS. 9A, 9B, 9C, and 9D. EGFR×CD28 (REGN7075) synergizes with anti-PD1 (cemiplimab) treatment to induce anti-tumor immunity in VH mice engrafted with human fetal liver CD34+ cells.
Figure 9B:
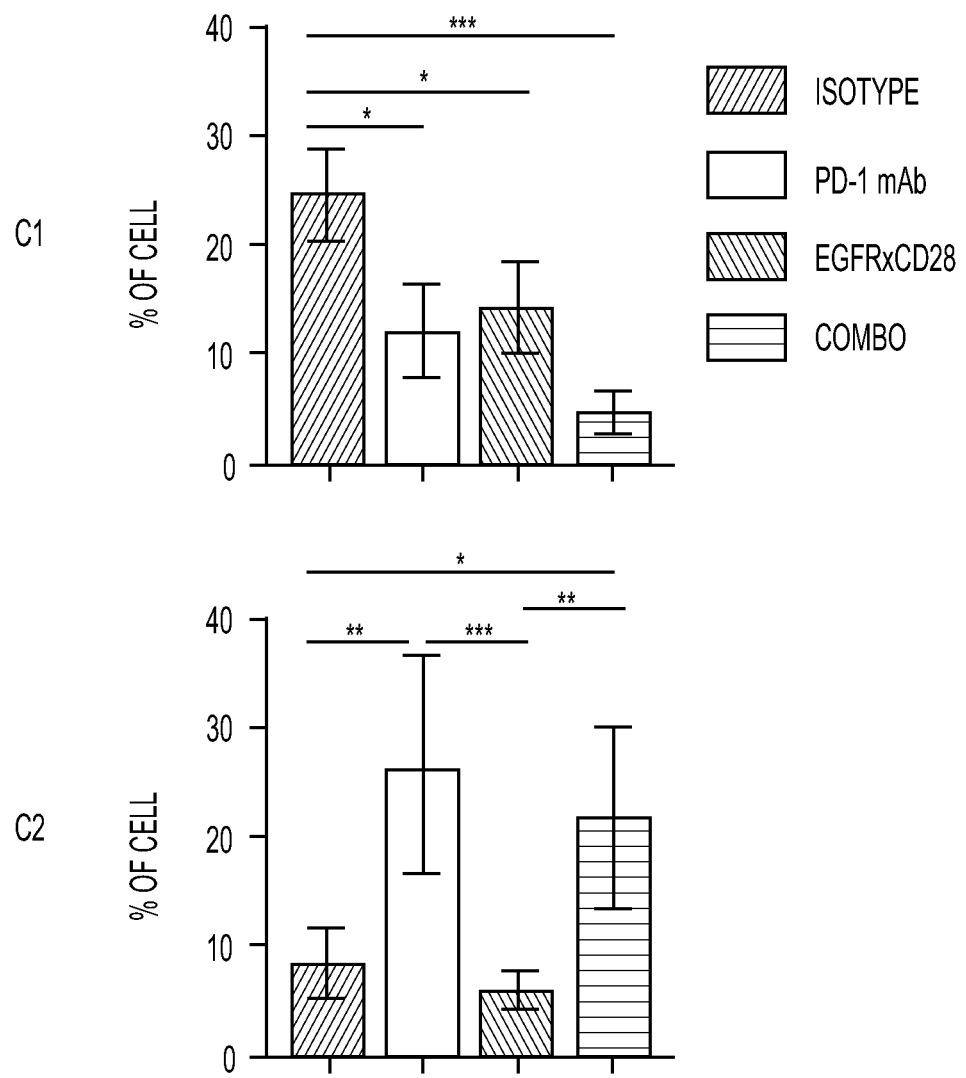
Figure 9C:
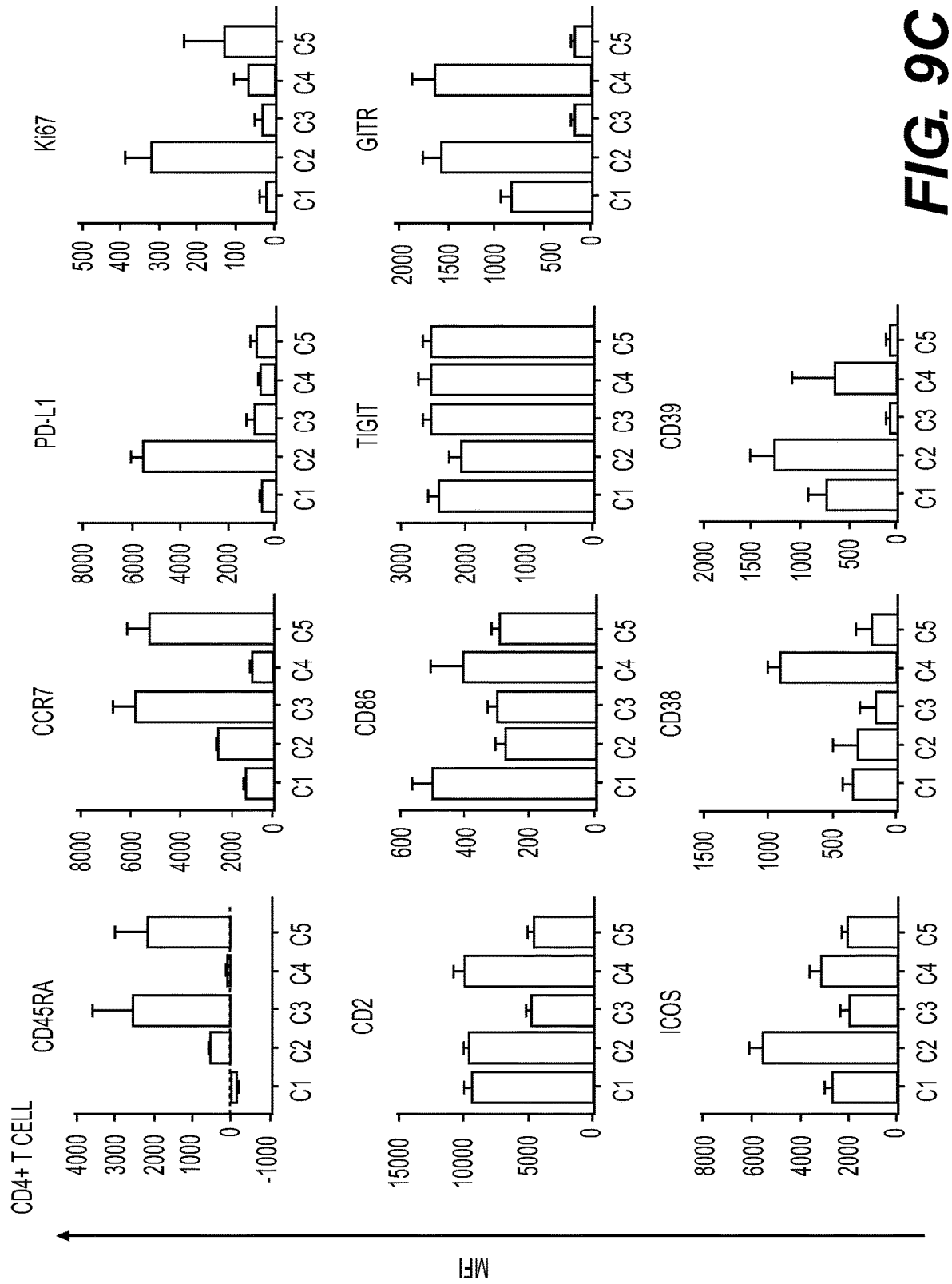
Figure 9D:
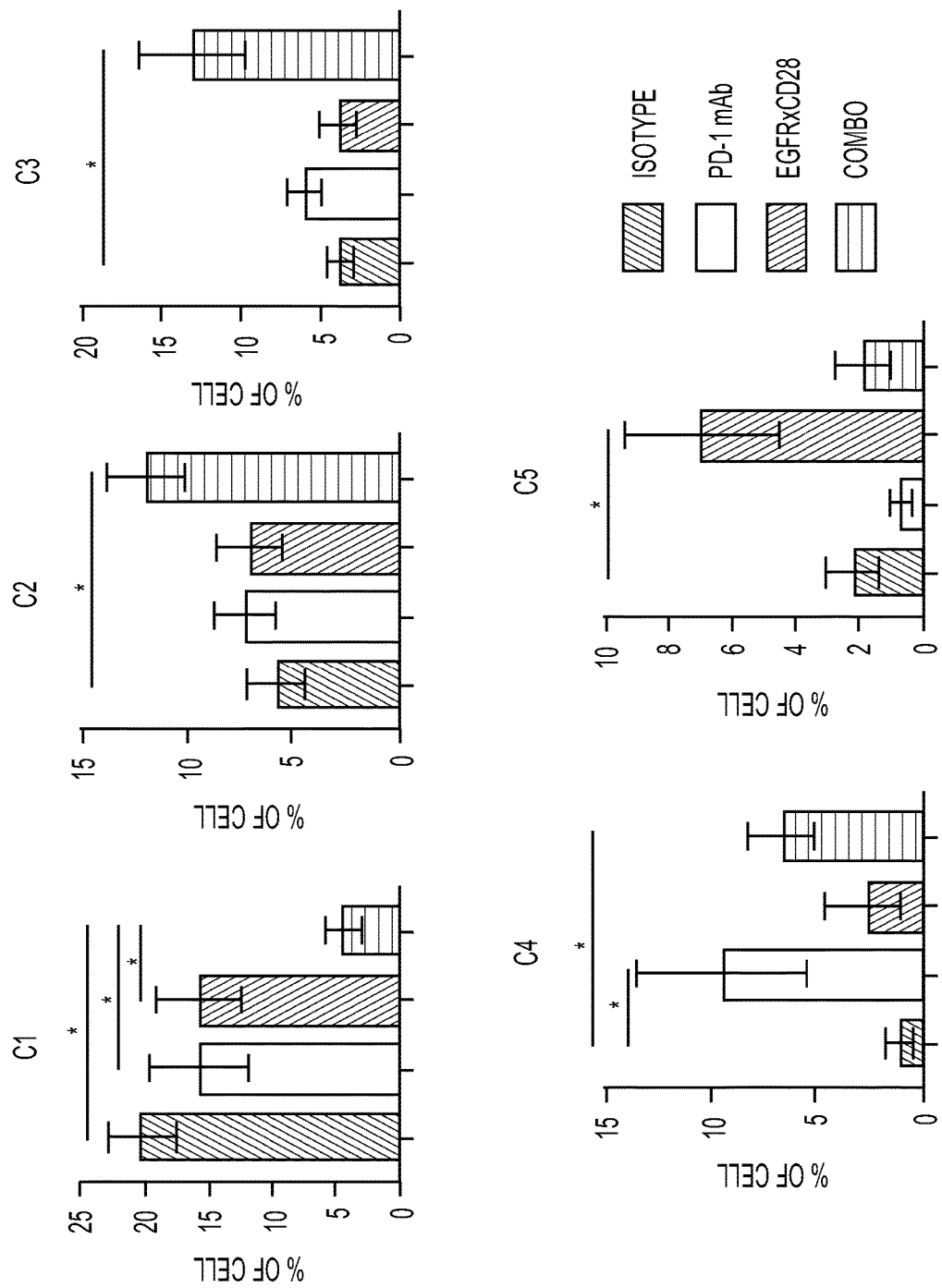

Both EGFR×CD28 (REGN7075) and anti-PD-1 Ab (cemiplimab) single agent treatment reduced CD8+ T-cell cluster C1, which expresses a high level of PD-L1 and ICOS (see FIGS. 9A and 9B). PD-1 blockade alone robustly drove the expansion of a CD8+ T-cell cluster C2 with a highly activated phenotype (High level of CD2, CD86, GITR, TIGIT and ICOS). Interestingly, more diverse CD4+ T cell clusters that responded to single or combination treatment (FIGS. 9C and 9D) were observed. Only combination treatment significantly expanded cluster C2 with proliferating effector memory like phenotype (High Ki67, low CD45RA and CCR7) and less exhausted effector memory like cluster C3 (Low CD38, CD45RA and CCR7). Similar to CD8+ T-cells, combination treatment significantly reduced the cluster C1 with higher PDL1 expression level. PD-1 blockade monotherapy drove the expansion of effector memory cells with higher CD38 expression level (C4), resembling a more activated phenotype. EGFR×CD28 monotherapy maintained the small pool of naïve like CD4+ T-cells in the tumor (C5), which may be further primed/activated upon anti-PD1 Ab treatment.

These data showed that a human xenograft tumor model in humanized mice provided a powerful platform to test EGFR×CD28 bi-specific antibody as monotherapy and in combination with a PD-1 blockade reagent. Using high-dimensional FACS analysis and a fully automated clustering identification method made it possible to further dissect the underlining immune mechanism in human immune system reconstituted mice. Although PD1 blockade alone was able to drive potent expansion of CD8+ and CD4+ T-cells with an activated phenotype, it was not sufficient to promote memory development and drive significant tumor inhibition. When combined with EGFR×CD28 treatment, a balanced T-cell activation state can be achieved and drive potent anti-tumor response.

Example 8: EGFR×CD28 Alone or in Combination with Anti-PD1 Therapy does not Induce Systemic T-Cell Activation in Comparison to CD28 Superagonist in Cynomolgus Monkeys To evaluate the tolerability of EGFR×CD28 bispecifics (REGN7075) alone, or the potential for synergistic pharmacology in combination with anti-PD1 antibody, studies in cynomolgus monkeys were conducted. Three monkeys per treatment group received a single dose (10 mg/kg) of EGFR×CD28 alone or in combination with REGN2810 (cemiplimab) (10 mg/kg) via intravenous infusion (combination groups received sequential infusions).

The cynomolgus monkey study was conducted in accordance with IACUC guidelines. For studies with EGFR× CD28, female cynomolgus monkeys (*Macaca fascicularis*) studies were carried out at SNBL USA (accredited by the Association for Assessment and Accreditation of Laboratory Animal Care, AAALAC; Animal Welfare Assurance issued by Office of Laboratory Animal Welfare, OLAW; registered with the United States Department of Agriculture, USDA and institutional animal care and use committee, IACUC). For flow cytometry, blood was collected from peripheral vein of restrained, conscious animals into potassium EDTA tubes. 100 µl of whole blood was stained with the indicated antibodies. Flow cytometric data acquisition was conducted using FACS Canto II. The absolute counts of the individual populations were calculated from their relative percentages as derived from the parent/grandparent population gate and the total parent/grandparent population counts from a validated hematology analyzer according to the formula: Absolute population count $(\times 10^3/\mu L)$=(population relative %×total parent/grandparent population count)/100. For serum cytokines, blood was collected into serum separator tubes with anticoagulant. Serum separated via centrifugation in centrifuge set to 4° C. Analyzed using the MSD U-Plex platform (IL-2, 4, 6, 8, 10, TNFα and IFNγ).

Figure 10A:
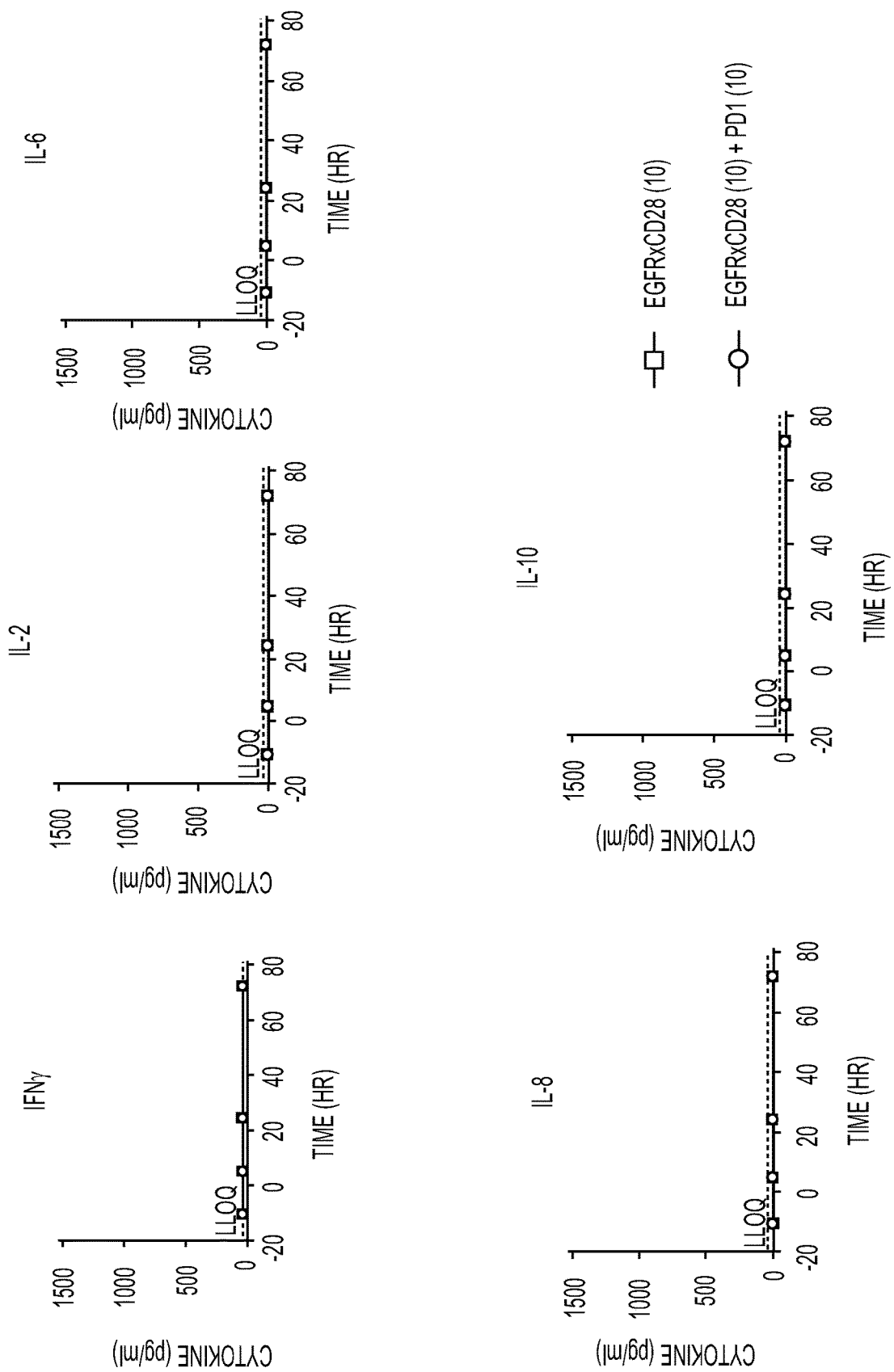

Assessment of toxicity was based on clinical observations, qualitative food consumption, body weight, and vital signs (body temperature, heart rate, pulse oximetry, and respiration rate), and clinical and anatomic pathology upon completion of the experiment. Blood samples were collected for cytokine and FACS immunophenotyping analysis. EGFR×CD28 alone or in combination with cemiplimab were well tolerated and all the animals survived to the time of scheduled necropsy. There was no test article related clinical-observations observed (data not shown). No changes in organ weights were found, nor were any macroscopic changes noted at the terminal necropsy (data not shown). Furthermore, no significant cytokine release, T-cell marginalization or activation were observed (FIGS. 10A-10C). In contrast, significant cytokine release, lymphocyte marginalization and T-cell activation was seen in monkeys administered a CD28 "superagonist" (data not shown). No significant treatment-related histological changes were observed in animals that were administered EGFR×CD28 alone or in combination with cemiplimab.

Example 9: Dose Dependent Anti-Tumor Response Mediated by EGFR× CD28 Bispecific Antibody (REGN7075) and Anti-PD-1 Antibody (REGN2810) Combination Therapy Materials and Methods

NCI-H292

The NCI-H292 cell line is a human mucoepidermoid pulmonary carcinoma cell line isolated from a 32-year old female patient (ATCC CRL-1848). The cell line was maintained in RPMI-1640 with 10% FBS supplemented with PSG (penicillin, streptomycin, and glutamine).

Peripheral Blood Mononuclear Cells (PBMC)

Human PBMC were obtained from ReachBio, Cat. #0500-401, Donor #0190205 was used in this study.

Procedure Used for Tumor Study:

Female NSG mice (age~10 weeks old) were used in the experiments. Mice were implanted subcutaneously with $4\times10^6$ tumor cells, which were mixed with $2\times10^6$ PBMC. Tumor growth was monitored by caliper twice a week throughout the duration of the study. The antibodies indicated in Table 12 were administered as monotherapy or in combination by intraperitoneal injection at stated dosages on indicated days post tumor implantation. Experiment was ended when mice have ulcerated tumor or tumor volume exceeding 1500 cm$^3$ in accordance with IACUC standards. Statistical Analysis is shown in Table 13. The data is summarized in FIGS. 11 and 12.

TABLE 12

Study Design

| Group | Ab 1 | Ab 1 dose (mg/kg) | Ab 2 | Ab 2 dose (mg/kg) | Mice per group |
|---|---|---|---|---|---|
| A | Isotype Control No. 1 | 1 | Isotype Control No. 2 | 0.1 | 8 |
| B | REGN2810 | 1 | Isotype Control No. 2 | 0.1 | 8 |
| C | Isotype Control No. 1 | 1 | REGN7075 | 0.1 | 8 |
| D | Isotype Control No. 1 | 1 | REGN7075 | 0.02 | 8 |

TABLE 12-continued

Study Design

| Group | Ab 1 | Ab 1 dose (mg/kg) | Ab 2 | Ab 2 dose (mg/kg) | Mice per group |
|---|---|---|---|---|---|
| E | REGN2810 | 1 | REGN7075 | 0.1 | 9 |
| F | REGN2810 | 1 | REGN7075 | 0.02 | 9 |

Isotype Control No.1 and Isotype Control No. 2are negative control antibodies that bind Fel d1 REGN7075 is the anti-EGFR X CD28 bispecific antibody also referred to as bsAb7075 REGN2810 is an anti-PD-1 antibody

TABLE 13

Day 32 statistical analysis: Mixed-effects model (REML) analysis

| Tukey's multiple comparisons test | Summary | P value |
|---|---|---|
| Isotype vs REGN2810 (1 mg/kg) + REGN7075 (0.1 mg/kg) | **** | <0.0001 |
| Isotype vs REGN2810 (1 mg/kg) + REGN7075 (0.02 mg/kg) | ** | 0.0073 |
| REGN2810 (1 mg/kg) vs REGN7075 (0.1 mg/kg) | * | 0.0131 |
| REGN2810 (1 mg/kg) vs REGN2810 (1 mg/kg) + REGN7075 (0.1 mg/kg) | **** | <0.0001 |
| REGN2810 (1 mg/kg) vs REGN2810 (1 mg/kg) + REGN7075 (0.02 mg/kg) | **** | <0.0001 |
| REGN7075 (0.1 mg/kg) + REGN2810 (1 mg/kg) + REGN7075 (0.1 mg/kg) | **** | <0.0001 |
| REGN7075 (0.1 mg/kg) + REGN2810 (1 mg/kg) + REGN7075 (0.02 mg/kg) | * | 0.0340 |
| REGN7075 (0.02 mg/kg) + REGN2810 (1 mg/kg) + REGN7075 (0.1 mg/kg) | **** | <0.0001 |
| REGN7075 (0.02 mg/kg) + REGN2810 (1 mg/kg) + REGN7075 (0.02 mg/kg) | **** | <0.0001 |

Summary

Figure 11:
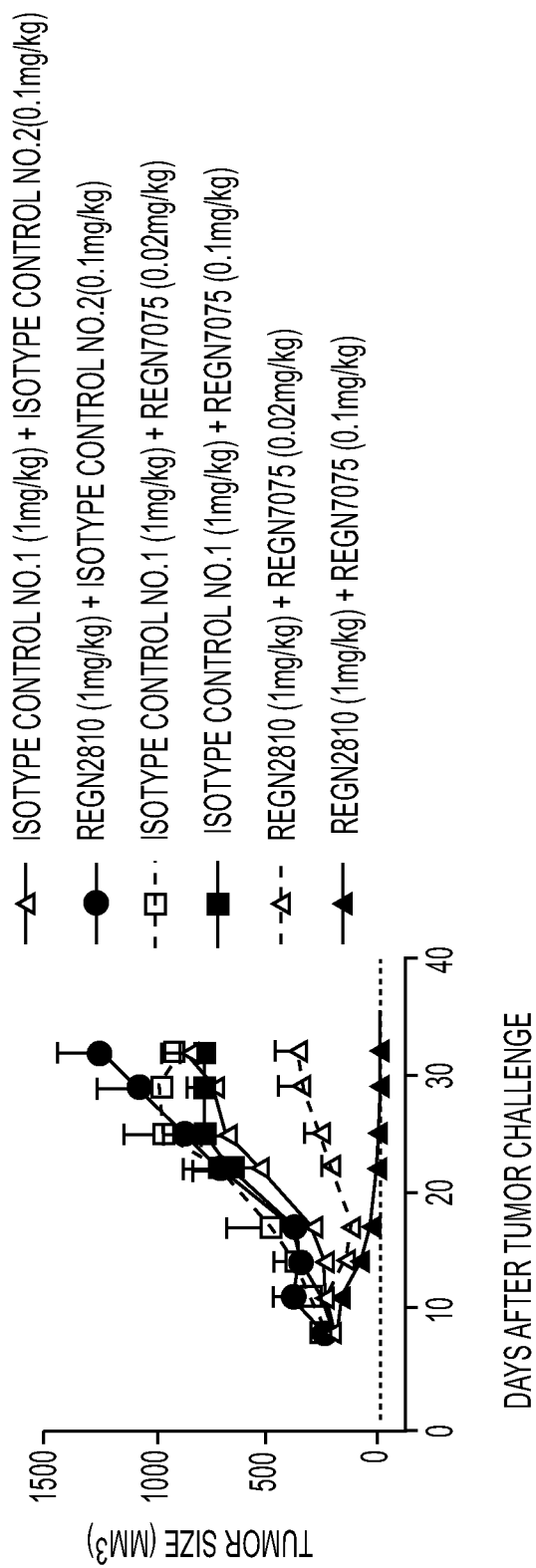
FIG. 11 shows a dose dependent anti-tumor response over time which is mediated by an anti-EGFR×anti-CD28 antibody (REGN7075) when combined with a PD-1 antibody (REGN2810, described as H2M7798N or H4H7798N in US20150203579).
Figure 12:
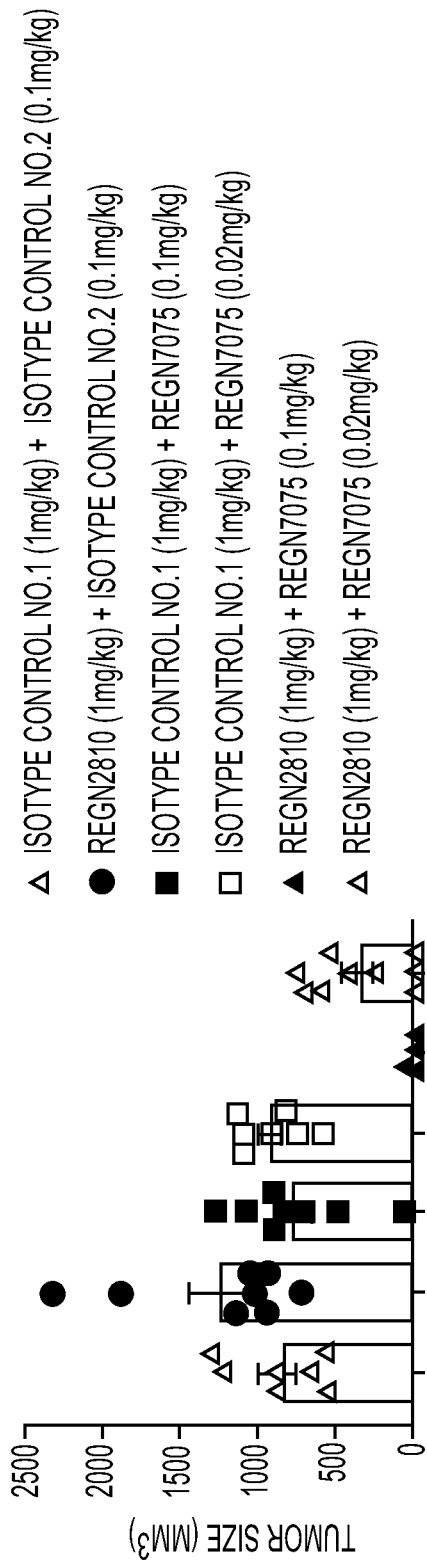
FIG. 12 shows a dose dependent anti-tumor response mediated by an anti-EGFR×anti-CD28 antibody (REGN7075) when combined with a PD-1 antibody (REGN2810).

The data, as shown in FIGS. 11 and 12, demonstrated that when tested in this model, the most robust anti-tumor response is observed when REGN7075 (anti-EGFR× anti-CD28) is combined with an anti-PD-1 antibody (REGN2810), as compared to the results obtained when either antibody is used alone.

Example 10A: Flow Cytometry Binding Titration Using REGN6323

Flow cytometric analysis was utilized to determine binding of anti-EGFR× anti-CD28 bispecific antibodies to several cancer cell lines (A375, 22RV1, PEO1, CAPAN2, SW1990, H292), Human and Cynomolgus T cells and Jurkat cells followed by detection with a labeled anti-human secondary IgG antibody. Briefly, $1 \times 10^5$ cells/well were incubated for 30 minutes at 4° C. with a serial dilution of EGFR×CD28 bispecific antibodies or Control Antibody (a human IgG4 antibody that binds a human antigen with no cross-reactivity to human or cynomolgus CD28), ranging from 100 nM to 1.5 pM for human and cynomolgus T cells, and ranging from 133 nM to 2 pM for EGFR expressing cells. After incubation, the cells were washed twice with cold PBS containing 1% filtered FBS and a Fluorophore-conjugated anti-human secondary antibody was added to the cells and incubated for an additional 30 minutes. Live/dead dye was added to Human and Cynomolgus T cells incubations. Wells containing no antibody or secondary only were used as a control.

After incubation with EGFR expressing cells, cells were washed, re-suspended in 200 μL cold PBS containing 1% filtered FBS and analyzed by flow cytometry on a BD FACS Canto II.

After incubation with Human or Cynomolgus T cells, cells were washed, and stained with a cocktail of anti-CD2, anti-CD16, anti-CD4, and anti-CD8 antibodies in Brilliant Stain Buffer for an extra 20 min incubation at 4° C. After wash, cells were re-suspended in 200 μL cold PBS containing 1% filtered FBS, gated in a Live/CD2+/CD4+/CD16− or Live/CD2+/CD8+/CD16− gate and analyzed by Flow cytometry on a BD FACS LSR-Fortessa-X20.

Results of Flow Cytometry Binding Titration (See Tables 14A and 14B and FIGS. 13A, 13B and 13C)

The binding of an anti-EGFR× anti-CD28 bispecific antibody (REGN6323) to the surface of human T cells and cynomolgus T cells was tested as described above by flow cytometry. The results showed that REGN6323 bound to both human and cynomolgus CD4+ and CD8+ T cells, without reaching saturation within the range of concentrations selected (FIG. 13A).

The binding of an anti-EGFR× anti-CD28 bispecific antibody (REGN6323) to the surface of other cell lines expressing EGFR was also tested by flow cytometry. The cell lines used were Jurkat cells (See FIG. 13C), which are an immortalized line of human T lymphocyte cells; A375 cells, which are an epithelial melanoma cell line; 22RV1 cells, which are an epithelial prostate carcinoma; PEO1 cells, which are an ovarian carcinoma cell line derived from ascites; CAPAN2, which is a pancreatic adenocarcinoma cell line; SW1990, which is a pancreatic adenocarcinoma derived from a metastatic site (spleen); and H292, which is a lung epithelial carcinoma cell line. The results show that REGN6323 bound to A375 cells with an EC50 of 1.48E-09M. REGN6323 bound to 22RV1 cells with an EC50 of 5.54E-10M. REGN6323 bound to PEO1 cells with an EC50 of 6.67E-10. REGN6323 bound to CAPAN2 cells with an EC50 of 1.29E-09M. REGN6323 bound to SW1990 cells with an EC50 of 2.96E-09M and REGN6323 bound to H292 cells with an EC50 of 6.74E-10 (See FIG. 13B).

The isotype control antibody did not exhibit any binding to human or cynomolgus T cells, nor did it bind to cell lines expressing EGFR.

These data suggest that REGN6323 is capable of binding a variety of cancer cell lines expressing EGFR and as such, may be effective for treating multiple cancer indications.

Example 10B: Flow Cytometry Binding Titration Using REGN6321 and REGN6322

An experiment was also done to determine whether other anti-EGFR× anti-CD28 bispecific antibodies could also exhibit bind to multiple cell types. Following the protocol described above, REGN6321 and REGN6322 were tested in a similar manner. REGN6323 was also included in this study.

The results, as shown in FIG. 13C, demonstrate that REGN6321, REGN6322 and REGN6323 exhibit binding to a prostate cell line, 22RV1, as well as a cell line designated PEO1, which is an ovarian cell line. These results demonstrated that these additional anti-EGFR× anti-CD28 antibodies are capable of binding across other cancer cell lines expressing EGFR.

TABLE 14

Summary of Flow Cytometry Binding Studies with Various EGFR X CD28 Bispecific Antibodies

| Anti-EGFR X Anti-CD28 Bispecific Antibody Designation | Binding EC$_{50}$ [M] | | | |
|---|---|---|---|---|
| | CASKI | A375 | 22RV1 | PEO1 |
| REGN6321 | 1.69E−08 | 5.42E−09 | +, NC | +, NC |
| REGN6322 | 2.44E−08 | 4.64E−09 | 9.58E−09 | 5.77E−09 |
| REGN6323 | 2.35E−09 | 8.74E−10 | 1.19E−08 | 5.86E−09 |
| REGN7075 | 2.05E−09 | NT | NT | 1.22E−09 |

NC: EC50 Not Calculated:
NT: Antibody not tested

Example 11: Cytotoxicity as Measured by Flow Cytometry

In order to monitor the killing of cells expressing Tumor Specific Antigens (TSA) of various sizes in the presence of a combination of an anti-TSAxanti-CD3 and an EGFRx CD28 antibody, 22RV1 (PSMA+, STEAP2+) or PEO1 (MUC16+) or CAPAN2 (MUC16+) or SW1990 (MUC16+) or H292 (MUC16+) cells were labeled with 1 uM of the fluorescent tracking dye Violet Cell Tracker. After labeling, cells were plated overnight at 37° C. Separately, human PBMCs were plated in supplemented RPMI media at 1×10$^6$ cells/mL and incubated overnight at 37° C. in order to enrich for lymphocytes by depleting adherent macrophages, dendritic cells, and some monocytes. The next day, target cells were co-incubated with adherent cell-depleted naïve PBMC (Effector/Target cell 4:1 ratio), a serial dilution of a targeting TSAxCD3 bispecific antibodies or a control TSAxCD3 bispecific antibody (concentration range: 66.7 nM to 0.2 pM) and a fixed concentration of an EGFRxCD28 costimulatory molecule REGN6323 at 2.5 ug/ml (16.7 nM) for 96 hours at 37° C. Cells were removed from cell culture plates using Trypsin-EDTA dissociation buffer, and analyzed by Flow Cytometry on a FACS BD LSRFortessa-X20. For Flow Cytometry analysis, cells were stained with a dead/live Near IR Reactive (Invitrogen) dye. 5E05 counting beads were added to each well immediately before Flow Cytometry analysis. 1E05 beads were collected for each sample. For the assessment of specificity of killing, cells were gated on live Violet labeled populations. Percent of live population was recorded and used for the calculation of survival.

T cell activation was assessed by incubating cells with directly conjugated antibodies to CD2, CD4, CD8, CD25, and by reporting the percent of late activated T cells out of total T cells (CD2+) or CD8+ T cells.
Results of Flow Cytometry Based Cytotoxicity Assay (See Table 15 and FIGS. 14 and 15)

The costimulatory EGFRxCD28 bispecific antibody REGN6323 was tested for its ability to enhance the cytotoxic potency of TSAxCD3 antibodies targeting cell surface antigens of various sizes, and across several cancer indications.

REGN6323 successfully enhanced the cytotoxic potency of various TSAxCD3 bispecific antibodies targeting PSMA or MUC16 or STEAP2 in the presence of unstimulated human PBMC. Target cell killing was enhanced in the presence of the an EGFRxCD28+TSAxCD3 bispecific antibodies combination compared to TSAxCD3 single agent treatment, and cells were killed in a dose-dependent manner with pM EC50s.

The observed target-cell lysis enhancement was associated with enhancement of CD25+ expression on T cells, again with pM EC50s.

TABLE 15

| | Kill (TSAxCD3 only) %, EC$_{50}$ [M] | T cell activation (TSAxCD3 only) %, EC$_{50}$ [M] | Kill (TSAxCD3 + EGFRxCD28) %, EC$_{50}$ [M] | T cell activation (TSAxCD3 + EGFRxCD28) %, EC$_{50}$ [M] |
|---|---|---|---|---|
| 22RV1 (with STEAP2xCD3) | 54%, 4.31E−11 | 93%, 3.86E−11 | 50%, 1.11E−11 | 97%, 6.27E−12 |
| 22RV1 (with PSMAxCD3) | 24%, N/C | 58%, 7.28E−10 | 46%, 5.5E−11 | 95%, 2.53E−11 |
| PEO1 (with MUC16xCD3) | 58%, 1.87E−10 | 44%, 1.51E−10 | 79%, 4.75E−11 | 60%, 1.71E−11 |
| CAPAN2 (with MUC16xCD3) | No activity | No activity | 7%, 5.29E−11 | 55%, 5.78E−11 |
| SW1990 (with MUC16xCD3) | 49%, 3.14E−10 | 30%, 1.64E−10 | 60%, 2.31E−11 | 85%, 2.14E−11 |
| H292 (with MUC16xCD3) | No activity | No activity | 32%, 3.96E−10 | 35%, 1.49E−10 |

Example 12: Epitope Mapping on EGFR with REGN7075, REGN6323 and REGN6322 by HDX-MS Hydrogen-Deuterium Exchange Mass Spectrometry (HDX-MS) was performed to determine the amino acid residues of the Epidermal Growth Factor Receptor (recombinant human EGFR, amino acid sequence in appendix) interacting with REGN7075 (mAb12999P2xmAb14226P2), mAb13006P (REGN6323 EGFR arm parental), and mAb35193P (REGN6322 EGFR arm parental). A general description of the HDX-MS method is set forth in e.g., Ehring (1999) *Analytical Biochemistry* 267(2):252-259; and Engen and Smith (2001) *Anal. Chem.* 73:256A-265A. The results are shown in Tables 16, 17 and 18.

The HDX-MS experiments were performed on an integrated HDX-MS platform, consisting of a Leaptec HDX PAL system for the deuterium labeling and quenching, a Waters Acquity M-Class (Auxiliary solvent manager) for the sample digestion and loading, a Waters Acquity M-Class (pBinary solvent manager) for the analytical gradient, and a Thermo Q Exactive HF mass spectrometer for peptide mass measurement.

The labeling solution was prepared as PBS buffer in D$_2$O at pD 7.0 (10 mM phosphate buffer, 140 mM NaCl, and 3 mM KCl, equivalent to pH 7.4 at 25° C.). For deuterium labeling, 11 μL of 52.0 pM hEGFR.mmh (Regeneron in house protein REGN355) or hEGFR.mmh premixed with REGN7075 in 1:1 molar ratio (Ag-Ab complex), 11 μL of 34.3 pM hEGFR.mmH (Regeneron in house protein REGN355) or hEGFR.mmH premixed with mAb13006P2 in 1:0.6 molar ratio (Ag-Ab complex), 11 μL of 31.4 pM hEGFR.mmH (Regeneron in house protein REGN355) or hEGFR.mmH premixed with mAb35193P2 in 1:0.6 molar ratio (Ag-Ab complex) were incubated at 20° C. with 44 μL of D$_2$O labeling solution for various time-points in duplicates (e.g., non-deuterated control=0 second; deuterium-labeled for 5 minutes and 10 minutes). The deuteration reaction was quenched by adding 55 μL of pre-chilled quench buffer (0.5 M TCEP-HCl, 8 M urea and 1% formic acid) to each sample for a 5-minute incubation at 20° C. The quenched samples were then injected into a Waters HDX Manager for online pepsin/protease XIII digestion. The digested peptides were separated by a C8 column (1.0 mm×50 mm, NovaBioassays) at −9.5° C. with a 22-minute gradient from 0%-90% B (mobile phase A: 0.5% formic acid and 4.5% acetonitrile in water, mobile phase B: 0.5% formic acid in acetonitrile). The eluted peptides were analyzed by a Thermo Q Exactive HF mass spectrometry in LC-MS/MS or LC-MS mode.

The LC-MS/MS data of undeuterated EGFR sample were searched against a database including hEGFR.mmH (REGN355) sequence and its reversed sequence using Byonic search engine (Protein Metrics). The search parameters were set as default using non-specific enzymatic digestion and human glycosylation as common variable modification. The list of identified peptides was then imported into the HDX Workbench software (version 3.3) to calculate the deuterium uptake of each peptide detected by LC-MS from all deuterated samples. For a given peptide, the centroid mass (intensity-weighted average mass) at each time point was used to calculate the deuterium uptake (D) and percentage of deuterium uptake (% D).

Deuterium Uptake ($D$−uptake) =

Average Mass (deuterated) − Average Mass (undeuterated)

Percentage of deuterium uptake (% $D$) =

$$\frac{D\text{−uptake for peptide at each time point} \times 100\%}{\text{Maximum } D\text{−uptake of the peptide}}$$

A total of 271 peptides from hEGFR.mmH (REGN355) were identified from both hEGFR.mmH alone and hEGFR.mmH in complex with REGN7075 samples, representing 84.4% sequence coverage of hEGFR.mmH. Any peptide which exhibited a differential percent D-uptake value above 5% was defined as significantly protected. Peptides corresponding to amino acids 345-368 (LHILPVAFRGDSFTHTPPLDPQEL SEQ ID NO: 70) and 399-416 (LEIIRGRTKQHGQFSLAV SEQ ID NO: 71) on hEGFR.mmH were significantly protected by REGN7075 (hEGFR.mmH residues are numbered according to hEGFR.mmH sequences).

A total of 341 peptides from hEGFR.mmH (REGN355) were identified from both hEGFR.mmH alone and hEGFR.mmH in complex with mAb13006P samples, representing 85.8% sequence coverage of hEGFR.mmH. Any peptide which exhibited a differential percent D-uptake value above 5% was defined as significantly protected. Peptides corresponding to amino acids 345-368 (LHILPVAFRGDSFTHTPPLDPQEL SEQ ID NO: 70) and 399-416 (LEIIRGRTKQHGQFSLAV SEQ ID NO: 71) on hEGFR.mmH were significantly protected by mAb13006P (hEGFR.mmH residues are numbered according to hEGFR.mmH sequences in the appendix).

A total of 335 peptides from hEGFR.mmH (REGN355) were identified from both hEGFR.mmH alone and hEGFR.mmH in complex with mAb35193P samples, representing 85.5% sequence coverage of hEGFR.mmH. Any peptide which exhibited a differential percent D-uptake value above 5% was defined as significantly protected. Peptides corresponding to amino acids 133-154 (CNVESIQWRDIVSSDFLSNMSM SEQ ID NO: 72) on hEGFR.mmH were significantly protected by mAb35193P (hEGFR.mmH residues are numbered according to hEGFR.mmH sequences).

TABLE 16 hEGFR.mmH peptides with significant protection upon formation of hEGFR.mmH-REGN7075 complex comparing to hEGFR.mmH alone

| hEGFR Residues | Charge (+) | 5 min | | | | 10 min | | | |
| --- | --- | --- | --- | --- | --- | --- | --- | --- | --- |
| | | hEGFR-REGN7075 Centroid MH$^+$ | hEGFR Centroid MH$^+$ | ΔD | | hEGFR-REGN7075 Centroid MH$^+$ | hEGFR Centroid MH$^+$ | ΔD | Δ % D |
| 345-352 | 2 | 455.74 | 456.12 | −0.38 | | 455.78 | 456.19 | −0.42 | −19.3 |
| 346-351 | 1 | 650.00 | 650.39 | −0.38 | | 650.06 | 650.50 | −0.45 | −16.9 |
| 346-352 | 1 | 797.35 | 797.97 | −0.62 | | 797.43 | 798.14 | −0.71 | −20.3 |
| 346-352 | 2 | 399.07 | 399.28 | −0.21 | | 399.08 | 399.32 | −0.24 | −14.1 |
| 346-355 | 2 | 563.57 | 564.01 | −0.44 | | 563.64 | 564.17 | −0.53 | −16.1 |
| 346-356 | 2 | 607.27 | 607.74 | −0.47 | | 607.35 | 607.91 | −0.56 | −15.9 |
| 346-367 | 3 | 826.78 | 827.17 | −0.39 | | 826.87 | 827.38 | −0.51 | −10.3 |
| 346-368 | 3 | 864.65 | 865.06 | −0.41 | | 864.81 | 865.31 | −0.50 | −10.0 |
| 399-412 | 2 | 843.25 | 843.57 | −0.32 | | 843.38 | 843.77 | −0.39 | −7.3 |
| 400-412 | 2 | 786.85 | 787.12 | −0.27 | | 786.97 | 787.33 | −0.36 | −7.0 |
| 400-412 | 3 | 524.89 | 525.07 | −0.18 | | 524.96 | 525.19 | −0.23 | −6.9 |
| 400-416 | 2 | 972.10 | 972.37 | −0.26 | | 972.15 | 972.62 | −0.47 | −6.0 |
| 401-412 | 2 | 722.21 | 722.47 | −0.26 | | 722.34 | 722.71 | −0.37 | −7.7 |
| 401-412 | 3 | 481.82 | 482.02 | −0.20 | | 481.90 | 482.16 | −0.26 | −8.5 |

TABLE 17 hEGFR.mmH peptides with significant protection upon formation of hEGFR.mmH-mAb13006P complex comparing to hEGFR.mmH alone

| | | 5 min | | | 10 min | | | |
|---|---|---|---|---|---|---|---|---|
| hEGFR Residues | Charge (+) | hEGFR-mAb13006P Centroid MH+ | hEGFR Centroid MH+ | ΔD | hEGFR-mAb13006P Centroid MH+ | hEGFR Centroid MH+ | ΔD | Δ % D |
| 345-352 | 2 | 455.74 | 456.16 | −0.41 | 455.82 | 456.18 | −0.36 | −18.7 |
| 346-351 | 1 | 650.01 | 650.40 | −0.40 | 650.08 | 650.50 | −0.42 | −16.4 |
| 346-352 | 1 | 797.35 | 797.99 | −0.64 | 797.47 | 798.12 | −0.65 | −19.6 |
| 346-354 | 2 | 505.90 | 506.44 | −0.54 | 505.99 | 506.57 | −0.58 | −22.8 |
| 346-355 | 2 | 563.51 | 564.07 | −0.56 | 563.62 | 564.18 | −0.56 | −19.6 |
| 346-356 | 2 | 607.23 | 607.78 | −0.55 | 607.34 | 607.92 | −0.57 | −17.3 |
| 346-367 | 3 | 826.80 | 827.22 | −0.42 | 826.93 | 827.37 | −0.44 | −10.0 |
| 346-368 | 2 | 1296.50 | 1297.08 | −0.58 | 1296.77 | 1297.40 | −0.63 | −8.9 |
| 346-368 | 3 | 864.63 | 865.06 | −0.43 | 864.80 | 865.29 | −0.48 | −10.0 |
| 399-412 | 2 | 843.24 | 843.64 | −0.41 | 843.32 | 843.76 | −0.44 | −8.7 |
| 400-412 | 2 | 786.75 | 787.15 | −0.40 | 786.84 | 787.29 | −0.45 | −9.6 |
| 400-412 | 3 | 524.83 | 525.10 | −0.28 | 524.88 | 525.18 | −0.30 | −9.6 |
| 400-415 | 2 | 922.54 | 922.99 | −0.45 | 922.65 | 923.09 | −0.44 | −7.9 |
| 400-416 | 2 | 972.04 | 972.46 | −0.42 | 972.11 | 972.57 | −0.46 | −7.3 |
| 401-412 | 2 | 722.13 | 722.56 | −0.43 | 722.23 | 722.67 | −0.44 | −10.8 |
| 401-412 | 3 | 481.79 | 482.09 | −0.31 | 481.86 | 482.17 | −0.32 | −11.5 |

TABLE 18 hEGFR.mmH peptides with significant protection upon formation of hEGFR.mmH-mAb35193P complex comparing to hEGFR.mmH alone

| | | 5 min | | | 10 min | | | |
|---|---|---|---|---|---|---|---|---|
| hEGFR Residues | Charge (+) | hEGFR-mAb35193P Centroid MH+ | hEGFR Centroid MH+ | ΔD | hEGFR-mAb35193P Centroid MH+ | hEGFR Centroid MH+ | ΔD | Δ % D |
| 133-139 | 1 | 793.31 | 793.75 | −0.45 | 793.33 | 793.96 | −0.64 | −13.3 |
| 133-142 | 2 | 626.18 | 626.65 | −0.47 | 626.23 | 626.80 | −0.57 | −15.8 |
| 133-147 | 2 | 877.53 | 878.02 | −0.49 | 877.56 | 878.27 | −0.71 | −11.4 |
| 137-141 | 1 | 690.43 | 690.70 | −0.28 | 690.48 | 690.86 | −0.38 | −13.2 |
| 137-147 | 2 | 654.56 | 654.79 | −0.22 | 654.63 | 654.91 | −0.28 | −6.9 |
| 138-147 | 2 | 610.96 | 611.19 | −0.23 | 611.06 | 611.31 | −0.25 | −7.4 |
| 140-142 | 1 | 476.68 | 476.72 | −0.03 | 476.70 | 476.81 | −0.11 | −8.4 |
| 143-148 | 1 | 668.39 | 668.72 | −0.33 | 668.47 | 668.88 | −0.41 | −11.3 |
| 148-152 | 1 | 612.31 | 612.48 | −0.17 | 612.38 | 612.59 | −0.21 | −7.5 |
| 148-154 | 2 | 1220.00 | 1220.45 | −0.45 | 1220.17 | 1220.51 | −0.34 | −18.6 |

Amino Acid Sequence of hEGFR.Mmh hEGFR(ECD).CPGG.MMH6 (REGN355): human EGFR (amino acids L25-A647, Accession #NM_005228.4), with a C-terminal CPGG.myc epitope(E1-L10).GlyGly.myc epitope(E1-L10).SerGly.6×His.SSG tag (mmh tag is underlined)

(SEQ ID NO: 69)
LEEKKVCQGTSNKLTQLGTFEDHFLSLQRMFNNCEVVLGNLEITYVQRNY

DLSFLKTIQEVAGYVLIALNTVERIPLENLQIIRGNMYYENSYALAVLSN

YDANKTGLKELPMRNLQEILHGAVRFSNNPALCNVESIQWRDIVSSDFLS

NMSMDFQNHLGSCQKCDPSCPNGSCWGAGEENCQKLTKIICAQQCSGRCR

GKSPSDCCHNQCAAGCTGPRESDCLVCRKFRDEATCKDTCPPLMLYNPTT

YQMDVNPEGKYSFGATCVKKCPRNYVVTDHGSCVRACGADSYEMEEDGVR

KCKKCEGPCRKVCNGIGIGEFKDSLSINATNIKHFKNCTSISGDLHILPV

AFRGDSFTHTPPLDPQELDILKTVKEITGFLLIQAWPENRTDLHAFENLE

IIRGRTKQHGQFSLAVVSLNITSLGLRSLKEISDGDVIISGNKNLCYANT

INWKKLFGTSGQKTKIISNRGENSCKATGQVCHALCSPEGCWGPEPRDCV

SCRNVSRGRECVDKCNLLEGEPREFVENSECIQCHPECLPQAMNITCTGR

GPDNCIQCAHYIDGPHCVKTCPAGVMGENNTLVWKYADAGHVCHLCHPNC

TYGCTGPGLEGCPTNGPKIPSIA<u>CPGGEQKLISEEDLGGEQKLISEEDLS</u>

<u>GHHHHHHSSG</u>

Example 13: Surface Plasmon Resonance Derived Binding Affinities and Kinetic Constants of EGFR×CD28 Bispecific and Associated Parental Antibodies to EGFR and CD28

EGFR Experimental Procedure

Equilibrium dissociation constants ($K_D$ values) for hEGFR.mmH (REGN355) binding to captured anti-EGFR×CD28 bispecific Abs were determined using a real-time surface plasmon resonance biosensor using a Biacore 4000 instrument. The CM5 Biacore sensor surface was derivatized by amine coupling with a monoclonal mouse anti-human Fc antibody (REGN2567, Lot #REGN2567-L1) to capture purified anti-EGFR×CD28 bispecific Abs. This Biacore binding study was performed in a buffer composed of 0.01 M HEPES pH 7.4, 0.15M NaCl, 3 mM EDTA, 0.05% v/v Surfactant P20 (HBS-EP running buffer). Different concentrations of hEGFR.mmH with a C-terminal myc-myc-hexahistidine tag (REGN355) prepared in HBS-EP running buffer (ranging from 30 nM to 120 pM, 3-fold serial dilutions) were injected over the Ab captured surface at a flow rate of 30 µL/minute. Association was monitored for 5 minutes, and the dissociation of hEGFR.mmH in HBS-EP running buffer was monitored for 10 minutes. All of the binding kinetics experiments were performed at 25° C. Kinetic association ($k_a$) and dissociation ($k_d$) rate constants were determined by fitting the real-time sensorgrams to a 1:1 binding model using Scrubber 2.0c curve fitting software. Binding dissociation equilibrium constants ($K_D$) and dissociative half-lives (t½) were calculated from the kinetic rate constants as:

$$K_D(M) = k_d/k_a, \text{ and } t½(\min) = 0.693/k_d/60$$

Binding kinetic parameters for hEGFR.mmH binding to purified EGFR×CD28 Abs at 25° C. are shown below in Table 19.

CD28 Experimental Procedure

Equilibrium dissociation constants ($K_D$ values) for purified bispecific Abs binding to captured hCD28.mFc (REGN2012) were determined using a real-time surface plasmon resonance biosensor using a Biacore T-200 instrument. The CM5 Biacore sensor surface was derivatized by amine coupling with a polyclonal rabbit anti-moue Fc antibody (GE Healthcare, Cat #BR100838) to capture purified hCD28 with a C-terminal mouse Fc tag (hCD28.mFc, REGN2012). This Biacore binding study was performed in a buffer composed of 0.01 M HEPES pH 7.4, 0.15M NaCl, 3 mM EDTA, 0.05% v/v Surfactant P20 (HBS-EP running buffer). Different concentrations of bispecific Abs prepared in HBS-EP (ranging from 90 nM to 1.1 nM, 3-fold serial dilutions) were injected over the hCD28.mFc captured surface at a flow rate of 50 µL/minute. Association was monitored for 4 minutes, and the dissociation of bispecific Abs in HBS-EP was monitored for 10 minutes. All of the binding kinetics experiments were performed at 25° C. Kinetic association ($k_a$) and dissociation ($k_d$) rate constants were determined by fitting the real-time sensorgrams to a 1:1 binding model using Scrubber 2.0 c curve fitting software. Binding dissociation equilibrium constants ($K_D$) and dissociative half-lives (t½) were calculated from the kinetic rate constants as:

$$K_D(M) = k_d/k_a, \text{ and } t½(\min) = 0.693/k_d/60$$

Binding kinetic parameters for EGFR×CD28 Abs binding to hCD28.mFc at 25° C. are shown below in Table 20.

Tabulated Data Summary:

TABLE 19 hEGFR.mmH Binding Kinetics to anti-EGFR × CD28 bispecific mAb at 25° C.

| REGN #/ Ab PID# | Lot # | EGFR Arm | CD28 Arm | Common Name | ka (1/Ms) | kd (1/s) | KD (M) | t½ (min) |
|---|---|---|---|---|---|---|---|---|
| REGN6321 | REGN6321-L4 | 13008P5 | 14226P5 | EGFR × CD28 | 7.30E+04 | 4.63E−05 | 6.34E−10 | 249.4 |
| REGN6322 | REGN6322-L3 | 35193P2 | 14226P2 | EGFR × CD28 | 1.56E+05 | 1.46E−03 | 9.38E−09 | 7.9 |
| REGN6323 | REGN6323-L2 | 13006P2 | 14226P2 | EGFR × CD28 | 2.06E+05 | 7.74E−04 | 3.75E−09 | 14.9 |

TABLE 20 hCD28.mFc Binding Kinetics to anti-EGFR × CD28 bispecific mAb at 25° C.

| REGN #/ Ab PID # | Lot # | EGFR Arm | CD28 Arm | Common Name | ka (1/Ms) | kd (1/s) | KD (M) | t½ (min) |
|---|---|---|---|---|---|---|---|---|
| REGN6321 | REGN6321-L4 | 13008P5 | 14226P5 | EGFR × CD28 | 2.59E+05 | 2.81E−03 | 1.08E−08 | 4.1 |
| REGN6322 | REGN6322-L3 | 35193P2 | 14226P2 | EGFR × CD28 | 2.61E+05 | 2.68E−03 | 1.03E−08 | 4.3 |
| REGN6323 | REGN6323-L2 | 13006P2 | 14226P2 | EGFR × CD28 | 2.65E+05 | 2.65E−03 | 1.00E−08 | 4.4 |

Example 14: Characterization of EGFR×CD28 Bispecific Antibodies in Ligand-Mediated Cell Growth Assay Using Engineered BaF3 Cells Overexpressing Human EGFR The EGFR (ErbB1, HER1) receptor is a member of the receptor tyrosine kinase (RTK) family, which regulate cell proliferation, survival, differentiation and migration of multicellular organisms. The activation of the receptor occurs via binding of its soluble ligands, e.g. EGF or TGFβ, which drive the homo-dimerization and autophosphorylation of EGFR, leading eventually to the activation of a plethora of intracellular signaling cascades such as Ras/MAPK, PLCγ1/PKC, PI3-kinase/Akt, and STAT pathways (Wieduwilt et al. 2008; Cell Mol Life Sci. May; 65(10): 1566-1584).

To study the blocking effects of anti-EGFR×CD28 antibodies on EGFR signaling, a proliferation assay was deployed using an engineered IL-3-dependent Ba/F3 murine hematopoietic cell line genetically modified to stably overexpress human epidermal growth factor receptor (EGFR—amino acids M1 to A1210 of Genbank accession #NP_005219.2) (Kong et al. 2017; Oncotarget, Vol. 8, (No. 22), pp: 35488-35489). Engineered BaF3/hEGFR cells were stimulated with ligands (human EGF or TGFβ) in the presence of titrated antibodies and cell growth was measured by tritium incorporation as a function of proliferating cells.

Experimental Procedures:

Engineered BaF3/hEGFR cells were grown in culture medium (RPM11640+10% FBS+Penicilin/Streptomycine/L-Glutamine+10 µg/mL mouse IL-3+0.5 µg/mL puromycine), were starved in media (RPM11640+1% FBS) without IL-3, for 24 h before using them in cell-proliferation assays. Briefly, in 96-well round-bottom tissue culture plates 12.5× 10^5 cells/well were added to 1:3 serially diluted antibodies, ranging from 15.2 pM to 100 nM including a no antibody containing control, in the presence of constant ligands, hEGF (0.5 nM) or hTGFβ (0.5 nM). Plates were incubated for 72 h at 37° C./5% $CO_2$, and 0.3 µCi/well tritiated thymidine was added to cells and plates were incubated for another 16 hours. Thymidine, and therefore tritium, will be incorporated at higher amounts into newly synthesized DNA of the dividing cells. After the incubation, cells were harvested onto 96-well UniFilter plates and 30 µL of scintillation fluid was added to each well. Tritium incorporation was measured as counts per minute (CPM) using the Microplate Scintillation & Luminescence Counter TopCount NXT instrument. Cells, antibodies and ligands were prepared in assay media (Opti-MEM+0.1% Bovine Serum Albumine) and all serial dilutions were tested in duplicate.

The $IC_{50}/EC_{50}$ values of the antibodies were determined from a 4-parameter logistic equation over a 10-point dose-response curve using GraphPad Prism™ software. Maximum inhibition of proliferation was determined by the following equation:

$$\text{Inhibition} (\%) = 100\% - \frac{100\% \times \left(\begin{array}{c}\text{Mean } CPM \text{ at 0.5 nM Ligand} + \\ 100 \text{ nM mAb} - \text{Background } CPM\end{array}\right)}{\begin{array}{c}(\text{Mean } CPM \text{ at 05 nM Ligand} + \\ 0 \text{ nM mAb} - \text{Background } CPM)\end{array}}$$

Summary of Results:

EGFR×CD28 bispecifics (REGN6322; REGN6323 and REGN7075) and their corresponding parental EGFR antibodies (mAb35193P2; mAb13006P2 and mAb12999P2) were tested alongside in-house generated comparator antibody (Erbitux) and isotype matched negative controls in the presence of 0.5 nM hEGF or hTGF3 (see Table 21).

In the Presence of 0.5 nM EGF:

None of the bispecific antibodies (REGN6322; REGN6323 and REGN7075) showed a dose-dependent inhibition of proliferation. Their maximal inhibition values ranged from 30.5 to −6.8% (negative values mean an increase of proliferation). Whereas mAb35193P2, mAb12999P2 and in-house Erbitux inhibited the proliferation of BaF3/hEGFR cells with $IC_{50}$ and maximal inhibition values of 2.55 nM/29.6%, 19.8 nM/91.8% and 6.69 nM/97.6%, respectively. mAb13006P2 displayed maximal inhibition of 93.2%, an $IC_{50}$ value could not be calculated. The negative isotype control antibodies showed no inhibition as expected.

In the Presence of 0.5 nM hTGF3:

REGN6322 showed a 40.6% increase in proliferation with an $EC_{50}$ of 3.67 nM, whereas REGN6323 and REGN7075 showed no response similar to the negative isotype control antibodies. In contrast, mAb13006P2, mAb12999P2 and in-house Erbitux inhibited the proliferation with $IC_{50}$ and maximal inhibition values of 6.55 nM/97.2%, 7.79 nM/95.9% and 1.38 nM/99.8%, respectively. mAb35193P2 displayed an increase of proliferation by 32.7% with an $EC_{50}$ value of 914 pM.

TABLE 21

Maximum Inhibition and Potency values of Antibodies

| Antibodies | In presence of 0.5 nM hEGF | | | In presence of 0.5 nM hTGFβ | | |
| --- | --- | --- | --- | --- | --- | --- |
| | Inhibition [%] | $IC_{50}$ [M] | $EC_{50}$ [M] | Inhibition [%] | $IC_{50}$ [M] | $EC_{50}$ [M] |
| REGN6322 | 30.5 | ND | | −40.6 | | 3.67E−09 |
| REGN6323 | 28.5 | ND | | −7.3 | ND | |
| REGN7075 | −6.8 | ND | | 11.2 | ND | |
| mAb35193P2 | 29.6 | 2.55E−09 | | −32.7 | | 9.14E−10 |
| mAb13006P2 | 93.2 | NC | | 97.2 | 6.55E−09 | |
| mAb12999P2 | 91.8 | 1.98E−08 | | 95.9 | 7.79E−09 | |
| In-house Erbitux | 97.6 | 6.69E−09 | | 99.8 | 1.38E−09 | |
| Isotype Control I | 7.8 | ND | | 18.9 | ND | |
| Isotype Control II | 14.1 | ND | | −1.4 | ND | |

Abbreviations: ND: Not Determined;
NC: Not Calculable;
a potency value could not be determined by PRISM.

Example 15: Characterization of EGFRxCD28 Bispecific Antibodies in Allogeneic T-Cell Activation Assays Using NCI-H292 and Human Primary T-Cells

TABLE 22

Reagent/Antibody Information/Materials:

| AbPID/REGN# | Description |
|---|---|
| REGN6322 | EGFRxCD28 |
| REGN6323 | EGFRxCD28 |
| REGN7075 | EGFRxCD28 |
| Non-TAA x CD28 | REGN6157 = non-TAA (tumor-associated antigen) x CD28 |
| Cemiplimab | REGN2810 (PD-1 antibody) |
| IsoC-1 | Isotype control for Cemiplimab |
| IsoC-2 | Isotype control CD28 bispecific |

Background

Two signals, "signal 1" & "signal 2," are required for proper T cell activation. "Signal 1" is induced by binding of the T cell receptor (TCR) on T cells to peptide-bound major histocompatibility complex (MHC) molecules on antigen presenting cells (APCs). Whereas, "signal 2" is provided by engaging the co-stimulatory CD28 receptor on T cells with its ligands cluster of differentiation 80 or 86 (CD80/CD86) present on APCs (Martin et al. 1986; June et al. 1987; Harding et al. 1992). Therefore, activation of CD28 signaling provides a targeted approach to enhance existing TCR signaling.

EGFRxCD28 bispecific antibodies are designed to mimic the natural ligands of CD28, by bridging EGFR+ target cells with CD28+ T cells, to provide "signal 2" in order to enhance the activation of T cells in presence of an existing "signal 1" in an allogeneic T cell activation assay. However, T cell activation can be inhibited by the ligation of programmed cell death protein 1 receptor (PD-1) on T cells to its ligand PD-L1 on APCs. Ligated PD-1 leads to the recruitment of phosphatases to CD28 and the TCR complex (Zou et al. 2008, Francisco et al. 2010, Hui et al. 2017), which in turn counteract TCR signaling and CD28 stimulation. Thus, blockade of the PD-1/PD-L1 interaction with cemiplimab in combination with EGFRxCD28 bispecific antibodies may potentiate T cell function and promote killing of target cells such as in cancer.

Experimental Procedures:

The ability of EGFRxCD28 bispecific antibodies to activate human primary T-cells by engaging EGFR and CD28 to deliver "signal 2", as determined by IL-2 release and T-cell proliferation, was evaluated in the presence of the EGFR+/PD-L1+ human lung cancer cell line (NCI-H292) that provides an allogeneic TCR response sufficient to serve as "signal 1".

Isolation of Human Primary CD3+ T Cells:

Human peripheral blood mononuclear cells (PBMCs) were isolated from a healthy donor leukocyte pack from Precision for Medicine (Donor 555015) using the EasySep™ Direct Human PBMC Isolation Kit, following the manufacturers recommended protocol and frozen down. CD3+ T-cells were isolated by thawing vials of frozen PBMCs. Donor PBMCs were enriched for CD3+ T-cells using an EasySep™ Human CD3+ T Cell Isolation Kit from StemCell Technologies and following the manufacturer's recommended instructions.

IL-2 Release Assay:

Enriched CD3+ T-cells, resuspended in stimulation media, were added into 96-well round bottom plates at a concentration of $1 \times 10^5$ cells/well. Growth-arrested NCI-H292 cells, which endogenously express EGFR and PD-L1, were added to CD3+ T-cells at a final concentration of $5 \times 10^4$ cells/well. Subsequently, REGN6322, REGN6323, REGN7075, Non-TAAxCD28, and their matched isotype control (IsoC-2) were titrated from 0.76 pM to 50 nM in a 1:4 dilution and added to wells. The final point of the 10-point dilution contained no titrated antibody. Following addition of titrated antibody, a constant 20 nM of either cemiplimab or its matched isotype control (IsoC-1) was added to wells. Plates were incubated for 96 hours at 37° C., 5% $CO_2$ and 50 □L total supernatant was removed and 5 □L from collected supernatant was used for measuring IL-2. The amount of IL-2 in assay supernatant was determined using AlphaLisa kit from PerkinElmer following the manufacturer's protocol. The IL-2 measurements were acquired on Perkin Elmer's multilabel plate reader Envision and values were reported as pg/mL. All serial dilutions were tested in triplicate.

The $EC_{50}$ values of the antibodies were determined from a four-parameter logistic equation over a 10-point dose-response curve using GraphPad Prism™ software. Maximal IL-2 is given as the mean max response detected within the tested dose range.

T-Cell Proliferation Assay:

After incubation of 96 hours at 37° C., 5% $CO_2$ and supernatant removal (see IL-2 release assay), 0.25 mCi/well tritiated thymidine was added to cells and plates were incubated for another 6-8 hours. Thymidine, and therefore tritium, will be incorporated at higher amounts into newly synthesized DNA of the dividing cells. After the incubation, cells were harvested onto 96-well UniFilter plates and 30 μL of scintillation fluid was added to each well. Tritium incorporation was measured as counts per minute (CPM) using the Microplate Scintillation & Luminescence Counter TopCount NXT instrument. All serial dilutions were tested in triplicate.

The $EC_{50}$ values of the antibodies were determined from a four-parameter logistic equation over a 10-point dose-response curve using GraphPad Prism™ software. Maximal CPM is given as the mean max response detected within the tested dose range.

Summary of Results (Table 23)

In the presence of cemiplimab EGFRxCD28 antibody treatment (REGN6322, REGN6323, and REGN7075) lead to higher IL-2 and proliferative response compared to Non-TAAxCD28 and IsoC-2, the respective matched isotype control for CD28 bispecifics. Whereas, in the absence of cemiplimab, EGFRxCD28 antibody treatment leads to higher IL-2 and proliferative response compared to Non-TAAxCD28 and IsoC-1, however the max values are lower.

TABLE 23

Maximum IL-2 release & Proliferation and Potency values of Antibodies

| | IL-2 Release | | Proliferation | |
|---|---|---|---|---|
| Antibodies | MAX (pg/mL) | $EC_{50}$ [M] | MAX (CPM) | $EC_{50}$ [M] |
| REGN6322 + cemiplimab | 21.8 | NC | 2382 | NC |
| REGN6323 + cemiplimab | 36.7 | NC | 2345 | 3.13E−11 |
| REGN7075 + cemiplimab | 27.2 | NC | 3250 | 2.16E−11 |

TABLE 23-continued

Maximum IL-2 release & Proliferation and Potency values of Antibodies

| Antibodies | IL-2 Release MAX (pg/mL) | IL-2 Release EC$_{50}$ [M] | Proliferation MAX (CPM) | Proliferation EC$_{50}$ [M] |
|---|---|---|---|---|
| Non-TAAxCD28 + cemiplimab | 10.5 | NC | 1215 | ND |
| IsoC-2 + cemiplimab | 8.99 | ND | 1106 | ND |
| REGN6322 + IsoC-1 | 8.02 | ND | 1863 | NC |
| REGN6323 + IsoC-1 | 13.2 | ND | 1665 | 2.29E−11 |
| REGN7075 + IsoC-1 | 12.7 | NC | 1880 | 3.92E−11 |
| Non-TAAxCD28 + IsoC-1 | 6.10 | ND | 632 | ND |
| IsoC-2 + IsoC-1 | 5.96 | ND | 875 | ND |

Abbreviations: ND: Not Determined; NC: Not Calculable; a potency value could not be determined by PRISM.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

We claim:

1. A bispecific antigen-binding molecule comprising a first antigen-binding domain that specifically binds human CD28, and a second antigen-binding domain that specifically binds human EGFR, (a) wherein the first antigen-binding domain that specifically binds human CD28 comprises three heavy chain complementarity determining regions (HCDR1, HCDR2 and HCDR3) and three light chain complementarity determining regions (LCDR1, LCDR2 and LCDR3), wherein the HCDR1 of the first antigen-binding domain comprises an amino acid sequence of SEQ ID NO: 12; the HCDR2 of the first antigen-binding domain comprises an amino acid sequence of SEQ ID NO: 6; the HCDR3 of the first antigen-binding domain comprises an amino acid sequence of SEQ ID NO: 14, the LCDR1 of the first antigen-binding domain comprises an amino acid sequence SEQ ID NO: 18, the LCDR2 of the first antigen-binding domain comprises the amino acid sequence GAS, and the LCDR3 of the first antigen-binding domain comprises an amino acid sequence SEQ ID NO: 22; and (b) wherein the second antigen-binding domain that specifically binds human EGFR comprises three heavy chain complementarity determining regions (HCDR1, HCDR2 and HCDR3) and three light chain complementarity determining regions (LCDR1, LCDR2 and LCDR3), wherein the HCDR1 of the second antigen-binding domain comprises an amino acid sequence of SEQ ID NO: 52, the HCDR2 of the second antigen-binding domain comprises an amino acid sequence of SEQ ID NO: 54, the HCDR3 of the second antigen-binding domain comprises an amino acid sequence of SEQ ID NO: 56, the LCDR1 of the second antigen-binding domain comprises an amino acid sequence of SEQ ID NO: 18, the LCDR2 of the second antigen-binding domain comprises the amino acid sequence GAS, and the LCDR3 of the second antigen-binding domain comprises an amino acid sequence of SEQ ID NO: 22.

2. The bispecific antigen-binding molecule of claim 1,
wherein the first antigen-binding domain comprises a heavy chain variable region (HCVR) comprising SEQ ID NO: 10, and a light chain variable region (LCVR) comprising SEQ ID NO: 16; and
wherein the second antigen-binding domain comprises a HCVR comprising SEQ ID NO: 50, and a LCVR comprising SEQ ID NO: 16.

3. The bispecific antigen-binding molecule of claim 1, wherein the antigen-binding molecule binds human cells expressing human CD28 and cynomolgus monkey cells expressing cynomolgus CD28.

4. The bispecific antigen-binding molecule of claim 1, wherein the antigen-binding molecule induces T-cell mediated cytotoxicity of human cancer cells.

5. The bispecific antigen-binding molecule of claim 4, wherein the cancer cells express EGFR.

6. The bispecific antigen-binding molecule of claim 4, wherein the cancer is selected from the group consisting of esophageal carcinoma, lung squamous cell carcinoma, lung adenocarcinoma, cervical squamous cell carcinoma, endometrial adenocarcinoma, bladder urothelial carcinoma, lung cancer, non-small cell lung cancer, colorectal cancer, rectal cancer, endometrial cancer, skin cancer, head & neck squamous cell carcinoma, brain cancer, glioblastoma multiforme, breast cancer, gastroesophageal cancer, gastroesophageal adenocarcinoma, prostate cancer and ovarian cancer.

7. The bispecific antigen-binding molecule of claim 1, that is a bispecific antibody, wherein:
(a) the first antigen-binding domain that specifically binds human CD28 comprises a heavy chain comprising the sequence of SEQ ID NO: 26, and a light chain comprising the sequence of SEQ ID NO: 28; and
(b) the second antigen-binding domain that specifically binds human EGFR comprises a heavy chain comprising the sequence of SEQ ID NO: 58, and a light chain comprising the sequence of SEQ ID NO: 28.

8. The bispecific antigen-binding molecule of claim 1 that is a bispecific antibody comprising a heavy chain of IgG1 isotype.

9. The bispecific antigen-binding molecule of claim 1 that is a bispecific antibody comprising a heavy chain of IgG4 isotype.

10. A pharmaceutical composition comprising the bispecific antigen-binding molecule of claim 1 and a pharmaceutically acceptable carrier or diluent.

* * * * *

UNITED STATES PATENT AND TRADEMARK OFFICE
CERTIFICATE OF CORRECTION

PATENT NO. : 12,415,856 B2  
APPLICATION NO. : 18/165515  
DATED : September 16, 2025  
INVENTOR(S) : Dimitris Skokos et al.

Page 1 of 1

It is certified that error appears in the above-identified patent and that said Letters Patent is hereby corrected as shown below:

In the Claims

At Column 112, Claim number 7, Line number 5, delete ","

Signed and Sealed this  
Ninth Day of December, 2025

John A. Squires  
*Director of the United States Patent and Trademark Office*